US011214620B2

(12) United States Patent
Campbell et al.

(10) Patent No.: US 11,214,620 B2
(45) Date of Patent: Jan. 4, 2022

(54) BINDING MOLECULES BINDING PD-L1 AND LAG-3

(71) Applicant: F-STAR DELTA LIMITED, Cambridge (GB)

(72) Inventors: Jamie Campbell, Cambridge (GB); Nikole Sandy, Cambridge (GB); Mihriban Tuna, Cambridge (GB); Francisca Wollerton Van Horck, Cambridge (GB); Katy Louise Everett, Cambridge (GB); Miguel Gaspar, Cambridge (GB); Matthew Kraman, Cambridge (GB); Katarzyna Kmiecik, Cambridge (GB); Mustapha Faroudi, Cambridge (GB); Natalie Fosh, Cambridge (GB); Barbara Hebeis, Cambridge (GB)

(73) Assignee: F-star Therapeutics Limited, Cambridge (GB)

( * ) Notice: Subject to any disclaimer, the term of this patent is extended or adjusted under 35 U.S.C. 154(b) by 434 days.

(21) Appl. No.: 16/311,604

(22) PCT Filed: Jun. 20, 2017

(86) PCT No.: PCT/EP2017/065073
§ 371 (c)(1),
(2) Date: Dec. 19, 2018

(87) PCT Pub. No.: WO2017/220569
PCT Pub. Date: Dec. 28, 2017

(65) Prior Publication Data
US 2019/0256602 A1 Aug. 22, 2019

Related U.S. Application Data

(60) Provisional application No. 62/352,482, filed on Jun. 20, 2016.

(51) Int. Cl.
*C07K 16/28* (2006.01)
*A61P 35/00* (2006.01)
*A61K 39/00* (2006.01)
*A61K 39/395* (2006.01)
*A61K 45/06* (2006.01)
*C07K 16/44* (2006.01)

(52) U.S. Cl.
CPC ...... *C07K 16/2827* (2013.01); *A61K 39/0011* (2013.01); *A61K 39/39541* (2013.01); *A61K 45/06* (2013.01); *A61P 35/00* (2018.01); *C07K 16/2803* (2013.01); *C07K 16/44* (2013.01); *A61K 2039/505* (2013.01); *A61K 2039/507* (2013.01); *C07K 2317/31* (2013.01); *C07K 2317/33* (2013.01); *C07K 2317/524* (2013.01); *C07K 2317/526* (2013.01); *C07K 2317/53* (2013.01); *C07K 2317/71* (2013.01); *C07K 2317/732* (2013.01); *C07K 2317/734* (2013.01); *C07K 2317/74* (2013.01); *C07K 2317/76* (2013.01); *C07K 2317/92* (2013.01); *C07K 2318/20* (2013.01)

(58) Field of Classification Search
None
See application file for complete search history.

(56) References Cited

U.S. PATENT DOCUMENTS

| | | | |
|---|---|---|---|
| 3,909,459 A | 9/1975 | Friese et al. | |
| 3,967,230 A | 6/1976 | Kamigaito et al. | |
| 4,004,183 A | 1/1977 | Oki et al. | |
| 6,380,664 B1 | 4/2002 | Pollner | |
| 9,567,399 B1 | 2/2017 | Campbell et al. | |
| 9,617,338 B1 | 4/2017 | Campbell et al. | |
| 10,090,646 B2 | 10/2018 | Takaoka et al. | |
| 10,205,305 B2 | 2/2019 | Uegaki et al. | |
| 2003/0030355 A1 | 2/2003 | Honda | |
| 2009/0055944 A1* | 2/2009 | Korman | A61P 35/00 800/18 |
| 2012/0276104 A1 | 11/2012 | Woisetschlager | |
| 2015/0214697 A1 | 7/2015 | Yoshida et al. | |
| 2015/0259420 A1* | 9/2015 | Triebel | A61P 35/00 424/136.1 |
| 2016/0043531 A1 | 2/2016 | Firstenberg et al. | |

(Continued)

FOREIGN PATENT DOCUMENTS

| | | |
|---|---|---|
| EP | 2 407 487 A1 | 1/2012 |
| EP | 2546268 A1 | 1/2013 |

(Continued)

OTHER PUBLICATIONS

"F-star Alpha: A new asset centric company." Retrieved from http://www.onenucleus.com/media/Events/LSLS/11%20feb%202014/Jane%20Dancer.pdf on Jan. 8, 2015, 15 p. (document marked Feb. 11, 2014).

(Continued)

*Primary Examiner* — Nelson B Moseley, II
(74) *Attorney, Agent, or Firm* — Wolf, Greenfield & Sacks, P.C.

(57) ABSTRACT

The present invention relates to antibody molecules which bind to programmed death-ligand 1 (PD-L1) and lymphocyte-activation gene 3 (LAG-3). The antibody molecules preferably comprise a CDR-based antigen binding site for PD-L1, and a LAG-3 antigen binding site which may be located in two or more structural loops of a CH3 domain of the antibody molecule. The antibody molecules of the invention find application, for example, in cancer therapy.

20 Claims, 18 Drawing Sheets
Specification includes a Sequence Listing.

(56) References Cited

U.S. PATENT DOCUMENTS

| | | |
|---|---|---|
| 2018/0175592 A1 | 6/2018 | Uegaki et al. |
| 2019/0202920 A1 | 7/2019 | Tuna et al. |
| 2019/0330344 A1 | 10/2019 | Tuna et al. |
| 2019/0338049 A1 | 11/2019 | Tuna et al. |
| 2021/0139590 A1 | 5/2021 | Tuna et al. |
| 2021/0238299 A1 | 8/2021 | Pechouckova et al. |

FOREIGN PATENT DOCUMENTS

| | | | |
|---|---|---|---|
| EP | 2 905 030 A1 | 8/2015 | |
| JP | S51-046628 A | 4/1976 | |
| JP | 2003-022886 A | 1/2003 | |
| JP | 2012-500006 A | 1/2012 | |
| JP | 2017-010741 A | 1/2017 | |
| WO | WO 2006/072620 A1 | 7/2006 | |
| WO | WO 2009/000006 A1 | 12/2008 | |
| WO | WO 2009/132876 A1 | 11/2009 | |
| WO | WO 2010/019570 A2 | 2/2010 | |
| WO | WO 2014/008218 A1 | 1/2014 | |
| WO | WO 2014/140180 A1 | 9/2014 | |
| WO | WO 2015/048312 A1 | 4/2015 | |
| WO | WO 2015/138920 A1 | 9/2015 | |
| WO | WO 2015/198312 A1 | 12/2015 | |
| WO | WO 2015/200119 A1 | 12/2015 | |
| WO | WO 2016/028672 A1 | 2/2016 | |
| WO | WO 2016/177802 A1 | 11/2016 | |
| WO | WO 2016/185016 A1 | 11/2016 | |
| WO | WO 2016/200782 A1 | 12/2016 | |
| WO | WO 2017/009456 A1 | 1/2017 | |
| WO | WO 2017/015560 A2 | 1/2017 | |
| WO | WO 2017/025498 A1 | 2/2017 | |
| WO | WO 2017/052241 A1 | 3/2017 | |
| WO | WO 2017/062888 A1 | 4/2017 | |
| WO | WO 2017/077085 A2 | 5/2017 | |
| WO | WO 2017/087589 A2 | 5/2017 | |
| WO | WO 2017/087901 A2 | 5/2017 | |
| WO | WO 2017/123650 A2 | 7/2017 | |
| WO | WO 2017/182672 A1 | 10/2017 | |
| WO | WO 2017/220569 A1 | 12/2017 | |
| WO | WO 2017/220990 A9 | 12/2017 | |
| WO | WO 2018/017673 A1 | 1/2018 | |
| WO | WO 2018/056821 A1 | 3/2018 | |
| WO | WO 2019/025545 A1 | 2/2019 | |

OTHER PUBLICATIONS

Jing et al., "Combined immune checkpoint protein blockade and low dose whole body irradiation as immunotherapy for myeloma." *Journal for Immunotherapy of Cancer*, DOI: 10.1186/S40425-014-0043-Z, 15 pages (Jan. 20, 2015).

Kraman et al., "A LAG-3/PD-L1 bispecific antibody inhibits tumour growth in two syngeneic colon carcinoma, models." *Journal for Immunotherapy of Cancer*, vol. 4 (Suppl 1), No. 82, p. 74, Abstract P124 (Nov. 16, 2016).

Kraman et al., "A LAG-3/PD-L1 bispecific antibody inhibits tumor growth in two syngeneic colon carcinoma models." Retrieved from http://www.f-star.com/media/73722/A-LAG-3-PD-L1-bispecific-antibody-inhibits-tumour-growth-in-two-syngeneic-colon-carcinoma-models.pdf, 1 p. (document marked Nov. 9-13, 2016).

U.S. Appl. No. 17/259,634, filed Jan. 12, 2021, Munoz-Olaya et al.
U.S. Appl. No. 17/259,677, filed Jan. 12, 2021, Munoz-Olaya et al.
U.S. Appl. No. 17/259,754, filed Jan. 12, 2021, Lakins et al.
U.S. Appl. No. 17/259,642, filed Jan. 12, 2021, Wollerton et al.
U.S. Appl. No. 17/259,714, filed Jan. 12, 2021, Tuna et al.
U.S. Appl. No. 17/259,791, filed Jan. 12, 2021, Lakins et al.
U.S. Appl. No. 17/259,796, filed Jan. 12, 2021, Tuna et al.
PCT/EP2017/065073, Aug. 11, 2017, International Search Report and Written Opinion.
PCT/EP2017/065073, Jan. 3, 2019, International Preliminary Report on Patentability.
International Search Report and Written Opinion for Application No. PCT/EP2017/065073, dated Aug. 11, 2017.
International Preliminary Report on Patentability for Application No. PCT/EP2017/065073, dated Jan. 3, 2019.
[No Author Listed] Abstract for CHI Immuno-Oncology Summit Europe. Mar. 18-22, 2019. 1 page. PDR303.
[No Author Listed] First-in-Class bispecific antibodies for cancer immunotherapy. Presentation at Takeda. Dec. 13, 2016. 24 pages. PDR160.
[No Author Listed] F-Star Modular Bispecific Antibodies. Summary for ATLAS deck. Presented at JP Morgan. Jan. 2017. 1 page. PDR159.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.
Asgarov et al., A new anti-mesothelin antibody targets selectively the membrane-associated form. MAbs. Apr. 2017;9(3):567-577. doi: 10.1080/19420862.2017.1288770.
Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 22, 2018. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG—Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with antihuman PD-1 (REGN2810) shows enhanced anti-tumor activity in PD-1 × LAG-3 dual-humanized mice and favorable pharmacokinetic and safety profiles in cynomolgus monkey. J Immunother Cancer. 2016;4(Suppl 1):P195. 2 pages.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.

(56) References Cited

OTHER PUBLICATIONS

Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate antitumor immune response to enhance antibody targeting of tumors. Curr Opin Immunol. Apr. 2015;33:1-8. doi: 10.1016/j.coi.2014.12.010. Epub Jan. 7, 2015.

Chiu et al., Antibody Structure and Function: The Basis for Engineering Therapeutics. Antibodies (Basel). Dec. 3, 2019;8(4):55. doi: 10.3390/antib8040055.

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.

Davies, Analytical challenges for next generation biologies. Oral Presentation at Waters Biopharma Mini-Seminar. May 24, 2017. 20 pages. PDR191.

Davies, Bispecific Antibodies: New Opportunities for Novel Therapies. Oral Presentation at Bioprocess UK 2016. Nov. 26, 2016. 14 pages. PDR 135.

Davies, Overcoming the Manufacturing Challenges for Bisepcific mAbs. Oral Presentation at 5th Annual Cell Culture and Bioprocessing Congress. Nov. 6, 2016. 16 pages. PDR142.

Davies, Overcoming the Manufacturing Challenges for Bisepcific mAbs. Oral Presentation at Biopronet 3rd Annual Scientific Symposium. Oct. 20, 2016. 16 pages. PDR136.

Daxini et al., Vasculitis associated with immune checkpoint inhibitors-a systematic review. Clin Rheumatol. Sep. 2018;37(9):2579-2584. doi: 10.1007/sl0067-018-4177-0. Epub Jun. 19, 2018.

Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.

Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.

Doody et al., Abstract B091: A LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.

Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.

Doody, In vivo Efficacy of bispecific antibodies targeting two immmune-modulatory receptors. Oral Presentation at PEGS Europe. Nov. 4, 2016. 16 pages. PDR144.

Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.

Everett et al., Abstract PR06: A LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.

Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.

Fiehler, Development of an anti-PD-L1 Fcab. Presentation. European Antibody Congress. Oct. 29, 2018. 26 pages. PDR312.

Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.

F-STAR, First-in-Class Bispecific Antibodies for Cance Immunotherapy. Jul. 2016. Presentation. 14 pages. PDR119.

Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.

Gliddon, Pushing all the buttons: innovating in immuno-oncology with mAb. Oral Presentation at Phacilitate Immunotherapy World 2017. Jan. 18, 2017. 11 pages. PDR165.

Goding et al., Combination of adoptive cell transfer, anti-PD-Ll and anti-LAG-3 antibodies for the treatment of recurrent tumors: better with more. OncoImmunology. Oct. 22, 2013;2(8):e25050-1-e25050-3.

Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.

Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.

Hid Cadena et al., Checks and Balances in Autoimmune Vasculitis. Front Immunol. Feb. 22, 2018;9:315. doi: 10.3389/fimmu.2018.00315.

Horn et al., CD3×PDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.

Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilites. Oct. 17-20, 2015. Orlando, FL. doi: 10.1158/1557-3265.OVCA15-PR03. Published Jan. 2016. 8 pages.

Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.

Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.

Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.

Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.

(56) References Cited

OTHER PUBLICATIONS

Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018. 1466016.
Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.
Kraman et al., A LAG-3/PD-L1 bispecific antibody inhibits tumour growth in two syngeneic coon carcinoma models. Poster 3005. Poster Presentation. Keystome Symposium—Biobetters and Next-Generation Biologies. Jan. 22-26, 2017. 1 page. PDR164.
Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.
La Motte-Mohs et al., Abstract 3217: MGD013, a bispecific PD-1 × LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.
La Motte-Mohs et al., MGD013, a bispecific PD-1 × LAG-3 Dual-Affinity Re-Targeting (DART®) protein with T-cell immunomodulatory activity for cancer treatment. Poster Presentation. 2016. http://ir.macrogenics.com/events.cfm. 1 page.
Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.
Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.
Lee et al., 4-1BB and OX40 dual costimulation synergistically stimulate primary specific CD8 T cells for robust effector function. J Immunol. Sep. 1, 2004;173(5):3002-12. doi: 10.4049/jimmunol. 173.5.3002.
Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.
Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.
Lobner et al., Engineered IgG1-Fc—one fragment to bind them all. Immunol Rev. Mar. 2016;270(1):113-31. doi: 10.1111/imr.12385.
Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862. 2017.1364825. Epub Aug. 17, 2017.
McCourt et al., KY1055; a novel ICOS/PD-L1 bispecific antibody, enhance T cell activation and delivers potent monotherapy antitumour response in vivo. Abstract. CIMT 2018. Feb. 28, 2018. 1 page. PDR245.
McCourt et al., KY1055; a novel ICOS/PD-L1 bispecific antibody, enhance T cell activation and delivers potent monotherapy antitumour response in vivo. Poster Presentation. CIMT Conference. May 9, 2018. 1 page. PDR 264.
McCourt et al., KY1055; a novel ICOS/PD-L1 bispecific antibody, enhance T cell activation and delivers potent monotherapy antitumour response in vivo. Presentation. CIMT Conference. May 9, 2018. 13 pages. PDR265.
Michaelson et al., Anti-tumor activity of stability-engineered IgG-like bispecific antibodies targeting TRAIL,-R2 and LTbetaR. MAbs. Mar.-Apr. 2009;1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20×CD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.
Powles et al., MPDL3280A (anti-PD-L1) treatment leads to clinical activity in metastatic bladder cancer. Nature. Nov. 27, 2014;515(7528):558-62. doi: 10.1038/nature13904.
Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol. 1101244. Epub Aug. 31, 2011.
Ramelet et al., Beneficial outcome of combination therapy with 4-1BB targeting antibody. Eur J Cancer. Nov. 29, 2016;69(Suppl 1):S96-S97.
Sainson et al., KY1055, a novel ICOS/PD-L1 bispecific antibody, efficiently enhances T cell activation and delivers a potent antitumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent antitumour response in vivo. Poster Presentation. AACR 2018. Apr. 4, 2018. 1 page. PDR254.
Sallin et al., The anti-lymphoma activities of anti-CD137 monoclonal antibodies are enhanced in Fc?RIII(−/−) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-IBB activation and PD-1 blockade enhances antitumor efficacy in a mouse model of subcutaneous tumor. Anticancer Res. Jan. 2015;35(1):129-36.
Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.
Tuna, Identification of a PD-L1 binding FCAB: a potent inhibitor of immunosuppressive signals. Abstract. European Antibody Congress. May 3, 2018. 1 page. PDR270.
Tuna, The use of bispecific antibodies to modulate anti-tumour immune responses. Oral Presentation at 10th Annual Proteins and Antibodies Congress. Apr. 24, 2017. 26 pages. PDR183.
Vanamee et al., Structural principles of tumor necrosis factor superfamily signaling. Sci Signal. Jan. 2, 2018;11(511):eaao4910. doi: 10.1126/scisignal.aao4910. 12 pages.

(56) References Cited

OTHER PUBLICATIONS

Vilgelm et al., Combinatorial approach to cancer immunotherapy: strength in numbers. Journal of Leukocyte Biology. 2016;100(2):275-90. Epub Jun. 2, 2016.

Weismann, A LAG-3/PD-L1 Bispecific Antibody Inhibits Tumour Growth In Two Syngeneic Colon Carcinoma Models. International Conference on Human and Translational Immunology. Rhodes, Greece. Sep. 16-21, 2016. Presentation. 6 pages. PDR128.

Wherry, T cell exhaustion. Nat Immunol. Jun. 2011;12(6):492-9. doi: 10.1038/ni.2035.

Wilton, KY1055, a bispecific mAb2 targeting ICOS and PD-L1. Presentation. Feb. 21, 2018. 17 pages. PDR238.

Wolchok et al., Nivolumab plus ipilimumab in advanced melanoma. N Engl J Med. Jul. 11, 2013;369(2): 122-33. doi: 10.1056/NEJMoa1302369. Epub Jun. 2, 2013. Erratum in: N Engl J Med. Nov. 29, 2018;379(22):2185. Author Manuscript.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

Workman et al., Negative regulation of T cell homeostasis by lymphocyte activation gene-3 (CD223). J Immunol. Jan. 15, 2005;174(2):688-95. doi: 10.4049/jimmunol.174.2.688.

Workman et al., The CD4-related molecule, LAG-3 (CD223), regulates the expansion of activated T cells. Eur J Immunol. Apr. 2003;33(4):970-9. doi: 10.1002/eji.200323382.

Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.

Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.

Wydro, Bispecific antibodies: new opportunities for novel therapies. Oral Presentation at 7th Annual Biologies Symposium. Mar. 1, 2017. 24 pages. PDR172.

Wykes et al., Immune checkpoint blockade in infectious diseases. Nat Rev Immunol. Feb. 2018;18(2):91-104. doi: 10.1038/nri.2017.112. Epub Oct. 9, 2017.

Xu et al., In vitro characterization of five humanized OKT3 effector function variant antibodies. Cell Immunol. Feb. 25, 2000;200(1):16-26.

Zhang et al., Structural basis of a novel PD-L1 nanobody for immune checkpoint blockade. Cell Discov. Mar. 7, 2017;3:17004. doi: 10.1038/celldisc.2017.4.

\* cited by examiner

A

CH3 (positions 1.4–80), with regions AB (positions 11–15) and CD (positions 45.1–45.4):

| Position | 1.4 | 1.3 | 1.2 | 1.1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 35 | 36 | 37 | 38 | 39 | 40 | 41 | 42 | 43 | 44 | 45 | 45.1 | 45.2 | 45.3 | 45.4 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| FS18-7-9 | G | Q | P | R | E | P | Q | V | Y | T | L | P | P | S | W | D | E | P | W | G | E | D | V | S | L | T | C | L | V | K | G | F | Y | P | S | D | I | A | V | E | W | E | S | N | G | Q | P | E | N | N | Y | K | T |
| FS18-7-32 | | | | | | | | | | | | | | | | | | | | | | | | | | | | | | | | | | | | E | | | | | | | | | | | | | | | | | |
| FS18-7-33 | | | | | | | | | | | | | | | | | | | | | | | | | | | | | | | | | | | | | | | | | | | | | | Y | | | D | | | | |
| FS18-7-36 | | | | | | | | | | | | | | | | | | | | | | | | | | | | | | | | | | | | | | | | | | | | | | I | | | I | | E | | |
| FS18-7-58 | | | | | | | | | | | | | | | | | | | | | | | | | | | | | | | | | | | | | | | | | | | | | | Y | | | W | | F | | |
| FS18-7-62 | | | | | | | | | | | | | | | | | | | | | | | | | | | | | | | | | | | | | | | | | | | | | | Y | A | | Y | | | | |
| FS18-7-65 | | | | | | | | | | | | | | | | | | | | | | | | | | | | | | | | | | | | | | | | | | | | | | Y | K | | E | | | | |
| FS18-7-78 | | | | | | | | | | | | | | | | | | | | | | | | | | | | | | | | | | | | | | | | | | | | | | V | | | L | | V | | |
| FS18-7-88 | | | | | | | | | | | | | | | | | | | | | | | | | | | | | | | | | | | | | | | | | | | | | | | | | | | | | | |
| FS18-7-95 | | | | | | | | | | | | | | | | | | | | | | | | | | | | | | | | | | | | | | | | | | | | | | Y | Q | | D | | | | |

CH3 (positions 81–129), with region EF (positions 92–101):

| Position | 81 | 82 | 83 | 84 | 84.1 | 84.2 | 84.3 | 84.4 | 85.4 | 85.3 | 85.2 | 85.1 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 112 | 113 | 114 | 115 | 116 | 117 | 118 | 119 | 120 | 121 | 122 | 123 | 124 | 125 | 129 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| FS18-7-9 | T | P | P | V | L | D | S | D | G | S | F | F | L | Y | S | K | L | T | V | P | Y | D | R | W | V | W | P | D | E | F | S | C | S | V | M | H | E | A | L | H | N | H | Y | T | Q | K | S | L | S | L | S | P | G |
| FS18-7-32 | | | | | | | | | | | | | | | | | | | | | | | | | | | | | | | | | | | | | | | | | | | | | | | | | | | | | | |
| FS18-7-33 | | | | | | | | | | | | | | | | | | | | | | | | | | | | | | | | | | | | | | | | | | | | | | | | | | | | | | |
| FS18-7-36 | | | | | | | | | | | | | | | | | | | | | | | | | | | | | | | | | | | | | | | | | | | | | | | | | | | | | | |
| FS18-7-58 | | | | | | | | | | | Y | | | | | | | | | | | | | | | | | | | | | | | | | | | | | | | | | | | | | | | | | | |
| FS18-7-62 | | | | | | | | | | | | | | | | | | | | | | | | | | | | | | | | | | | | | | | | | | | | | | | | | | | | | |
| FS18-7-65 | | | | | | | | | | | | | | | | | | | | | | | | | | | | | | | | | | | | | | | | | | | | | | | | | | | | | |
| FS18-7-78 | | | | | | | | | | | | | | | | | | | | | | | | | | | | | | | | | | | | | | | | | | | | | | | | | | | | | |
| FS18-7-88 | | | | | | | | | | | | | | | | | | | | | | | | | | | | | | | | | | | | | | | | | | | | | | | | | | | | | |
| FS18-7-95 | | | | | | | | | | | | | | | | | | | | | | | | | | | | | | | | | | | | | | | | | | | | | | | | | | | | | |

| Fcab | Identity to FS18-7-9 |
|---|---|
| FS18-7-32 | 99.1% |
| FS18-7-33 | 99.1% |
| FS18-7-36 | 99.1% |
| FS18-7-58 | 96.2% |
| FS18-7-62 | 98.1% |
| FS18-7-65 | 97.2% |
| FS18-7-78 | 97.2% |
| FS18-7-88 | 97.2% |
| FS18-7-95 | 97.2% |

BINDING MOLECULES BINDING PD-L1 AND LAG-3

CROSS REFERENCE TO RELATED APPLICATIONS

This is the U.S. National Stage of International Application No. PCT/EP2017/065073, filed Jun. 20, 2017, which was published in English under PCT Article 21(2), which in turn claims the benefit of U.S. Provisional Application No. 62/352,482 filed on Jun. 20, 2016, the contents of which are hereby incorporated by reference in their entirety.

FIELD OF THE INVENTION

The present invention relates to antibody molecules which bind to programmed death-ligand 1 (PD-L1) and lymphocyte-activation gene 3 (LAG-3). The antibody molecules preferably comprise a CDR-based antigen binding site for PD-L1, and a LAG-3 antigen binding site which may be located in two or more structural loops of a CH3 domain of the antibody molecule. The antibody molecules of the invention find application, for example, in cancer therapy.

BACKGROUND TO THE INVENTION

Lymphocyte Activation Gene-3 (LAG-3; CD223) is a member of the Ig superfamily, and is genetically and structurally related to CD4 (though with only 20% sequence identity). Like CD4, LAG-3 binds to MHC class II molecules but with higher affinity than CD4 ($K_D$=60 nM). LAG-3 is expressed on activated T cells, NK cells, pDCs, B cells, γδ T cells and participates in immune suppression, particularly through persistent strong expression in a percentage of regulatory T cells (Tregs) (Liang et al, 2008).

The LAG-3 gene is located on human chromosome 12, adjacent to the CD4 gene, and spans 8 exons. There are five alternative transcripts, two of which generate protein products: a full length transmembrane protein and an alternatively spliced soluble monomeric form. The full-length transcript encodes a 525 amino acid protein with a molecular weight of 70 kDa and has functional activity, while the soluble form appears not to bind MHC class II molecules and its function is unknown. Human full-length LAG-3 protein has 93% sequence identity to *Macaca fascicularis* (cynomolgus monkey) LAG-3 and 70% sequence identity to *Mus musculus* (house mouse) LAG-3.

LAG-3 is a transmembrane protein with four extracellular Ig-like domains (D1-D4), and a cytoplasmic portion responsible for LAG-3 signalling. The cytoplasmic domain has an EP (glutamic acid/proline) motif that associates with LAG-3-associated protein (LAP) as well as a KIEELE motif thought to be required for LAG-3 modulation of T cell function. Reports on the role of the EP motif suggest that it may be responsible for trafficking of LAG-3 to the T cell surface membrane (Bae et al, 2014), or may be directly responsible for modulating downstream signalling of STAT5 during T cell activation (Durham et al, 2014), or possibly both.

The immuno-suppressive mechanism of LAG-3 on T cells is thought to be driven by cross-linking of LAG-3 on activated T cells resulting in decreased calcium flux and IL-2 release during T cell activation (Huard et al, 1997). On Antigen Presenting Cells (APCs), binding to MHC II molecules by LAG-3 positive regulatory T cells causes decreased IL-12 secretion and down regulation of CD86 (Liang et al, 2008), a "secondary signal" of activation, resulting in T cell anergy from improper activation and/or reduced antigen presentation by the APCs. LAG-3 knock out mouse models are viable, with only mild lympho-hyperproliferation (Workman et al, 2003), indicating that LAG-3 acts as a modest immune "brake".

This suppressive interaction between LAG-3 and MHC class II has also been proposed to occur between Tregs and CD4 positive T cells (Sega et al, 2014). Tregs suppress the immune response either by release of suppressive cytokines (such as IL-10 and TGFβ), manipulation of inflammatory metabolism (such as CD73 catabolised adenosine), regulating APC maturation, or direct interaction between regulatory T cells and effector T cells. There is evidence in humans that MHC class II positive Tregs are more suppressive than MHC class II negative Tregs (Baecher-Allen et al, 2006) and actively suppress the immune response through direct interaction with LAG-3 expressed on effector T cells. While LAG-3 negative Tregs can suppress conventional T cell proliferation, LAG-3 negative CD4 and CD8 T cells are resistant to Treg immune suppression. This process was described to occur between human T cells through a process known as trogocytosis (Sega et al, 2014) whereby Tregs not only prevent APC maturation but also acquire MHC class II to suppress primed LAG-3 positive CD4 T cells.

LAG-3 expression is also a marker of repeated antigen stimulation. In cancer, T cells commonly adopt an "exhausted" phenotype, involving expression of immuno-suppressors such as PD-1, CTLA-4, TIM-3, and LAG-3 (Wherry et al, 2011), where the cells have a general inability to properly proliferate and secrete chemokines in response to antigen. Inhibition of these immune-suppressors lowers the immune threshold and (re-)enables a proper anti-cancer response by the T cells. In preclinical models, this has been borne out using antagonist antibodies against LAG-3, CTLA-4 and PD-1 where a decrease in tumour burden was seen. LAG-3 inhibition by antagonistic antibodies is thought to reactivate the immune response in the tumour microenvironment, where expression of LAG-3 on CD4 positive T cells and CD8 positive T cells is associated with an exhausted phenotype, and LAG-3 expression on Tregs is associated with potent immuno-suppressive capabilities. Antibodies blocking LAG-3 increase T effector cell proliferation, cytokine production, cytotoxicity, and decrease Treg suppressor activity leading to a decrease in tumour growth.

In human tumours, increased expression of LAG-3 was found on tumour-infiltrating lymphocytes (TILs) from human renal cell carcinomas and other tumours, such as melanomas and lymphomas (Demeure et al, 2001; Wolchock et al, 2013). Importantly, LAG-3 is also closely correlated with T cell dysfunction in patients with chronic viral infection (Workman et al, 2005) and cancer (Workman et al, 2003). LAG-3 has also been identified as a surface marker for tumour-infiltrating Tregs in a variety of human cancers (Camisachi et al. 2010; Gandhi et al, 2006).

Monoclonal antibodies to human LAG-3 are in clinical development to abrogate immune suppression and potentially enhance antigen presentation in cancers (solid and haematological malignancies).

LAG-525 and IMP-701 (Novartis AG), are human antibodies against LAG-3 and have advanced to Phase II and I clinical studies, respectively, in kidney cancer (Renal Cell Cancer); Non-Small Cell Lung Cancer (NSCLC); Nasopharyngeal Cancer; Colorectal Cancer; Melanoma; Gastric Cancer and Adenocarcinoma of the Gastroesophageal Junction.

Anti-LAG-3 antibody BMS-986016 (Bristol-Myers Squibb Company), is currently in Phase I clinical testing for Ovarian Cancer; NSCLC; Colorectal Cancer; Cervical Cancer; Melanoma; Gastric Cancer; Bladder Cancer; Head And Neck Cancer Squamous Cell Carcinoma; Renal Cell Carcinoma and in Phase II studies in NSCLC; Relapsed Chronic Lymphocytic Leukemia (CLL); Refractory Chronic Lymphocytic Leukemia (CLL); Melanoma; Non-Hodgkin Lymphoma; Hodgkin Lymphoma; Diffuse Large B-Cell Lymphoma; Indolent Lymphoma; Mantle Cell Lymphoma; Refractory Multiple Myeloma; and Relapsed Multiple Myeloma as either monotherapy or as part of combination therapies.

Further antibodies against LAG-3 are also in preclinical development.

Programmed cell death 1 (PD-1) and its ligands PD-L1 (CD274, B7-H1) and PD-L2 (B7-DC) deliver inhibitory signals that regulate the balance between T cell activation, tolerance, and immunopathology. PD-L1 is transiently expressed on all immune cells and some tumour cells.

PD-L1 is a type I transmembrane protein with two Ig-like domains within the extracellular region, a transmembrane domain and a short cytoplasmic domain. The cytoplasmic domain has no known signal transduction motif suggesting that there is no signalling by PD-L1 on interaction of the ligand with its receptor. Its molecular weight is 40 kDa (290 amino acids) and it is encoded by the CD274 gene on mouse chromosome 19 and human chromosome 9, respectively. PD-L1 is a member of the B7 protein family and shares approximately 20% amino acid sequence identity with B7.1 and B7.2. Human PD-L1 shares 70% and 93% amino acid identity with the murine and cynomolgus orthologs of PD-L1, respectively.

PD-L1 binds to its receptor PD-1 with an affinity ($K_D$) of 770 nM. PD-1 is expressed on activated T cells, B cells, and myeloid cells, and modulates activation or inhibition of cellular immune responses. Binding of PD-L1 to PD-1 delivers an inhibitory signal, reducing cytokine production and proliferation of T cells. Consequently, PD-L1 expression by cells can mediate protection against cytotoxic T lymphocyte (CTL) killing and is a regulatory mechanism that dampens chronic immune responses during viral infections. Cancer, as a chronic and pro-inflammatory disease subverts this immune-protective pathway through up-regulation of PD-L1 expression to evade the host immune response. In the context of an active immune response, IFNγ also upregulates the expression of PD-L1.

PD-L1 also mediates immune suppression through interaction with another protein, B7.1 (also known as CD80), blocking its ability to deliver one of the secondary signals of activation on T cells through CD28. In terms of PD-L1 expression on tumour cells and its engagement with B7.1, the relevance of this specific interaction in tumour immune resistance is still unclear.

PD-L1 expression has been shown in a wide variety of solid tumours. Of 654 samples examined in one study, spanning 19 tumours from different sites, 89 (14%) were PD-L1 positive (≥5% frequency). The highest PD-L1 positive frequencies were seen in head and neck ($17/54$; 31%), cervical ($10/34$; 29%), cancer of unknown primary origin (CUP; $8/29$; 28%), glioblastoma multiforme (GBM; $5/20$; 25%), bladder ($8/37$; 21%), oesophageal ($16/80$; 20%), triple negative (TN) breast ($6/33$; 18%), and hepatocarcinoma ($6/41$; 15%) (Grosso et al, 2013). Tumour-associated expression of PD-L1 has been shown to confer immune resistance and potentially protect tumour cells from T cell mediated apoptosis.

Therapies targeting PD-L1 have shown excellent results in murine in vivo studies. In the B16 murine model of melanoma, treatment with anti-PD-L1 combined with either GVAX or FVAX vaccination strategies resulted in a significant effect both on survival (30 days for control vs 52 days for PD-L1-treated) and percentage of tumour-free (5%) animals upon conclusion of the study (Curran et al, 2010). Anti-PD-L1 therapy has also been used to study the mechanism of immune suppression in the P815 murine mastoma model. P815 cells injected into mice normally trigger a strong immune response, which results in their rejection. When PD-L1 is expressed on P815 cells, these cells escape immune attack, which in turn can be negated through administration of anti-PD-L1 antibodies (Iwai et al, 2002). It is evident that targeting the PD-1/PD-L1 axis in immunogenic human cancers (Herbst et at, 2014) results in a survival advantage through stimulation of an anti-cancer immune response (Wolchock et al, 2013; Larkin et al, 2015).

Atezolizumab (MPDL3280A, RG7466, TECENTRIQ) is a humanized IgG1 antibody which binds PD-L1. It is in clinical trials as a single agent and also in combination with other biologic and/or small molecule therapies for treatment of solid cancers, including colorectal cancer, breast cancer, non-small-cell lung carcinoma, bladder cancer, and renal cell carcinoma. Treatment with atezolizumab resulted in objective response rates (ORR) of 23% in NSCLC, 36% melanoma, 33% bladder, 14% in RCC, and 13% in head and neck cancers (Herbst et al, 2014; Powles et al, 2014).

Avelumab (MSB0010718C) is a fully human IgG1 antibody which binds to PD-L1 and is undergoing clinical testing in a number of cancers including bladder cancer, gastric cancer, head and neck cancer, mesothelioma, non-small-cell lung carcinoma, ovarian cancer, renal cancer and Merkel-cell carcinoma.

Durvalumab (MED14736) is a human IgG1 antibody which binds to PD-L1 and is being tested in clinical trials alone or in combination with tremelimumab in non-small-cell lung cancer, squamous cell carcinoma of the head and neck, bladder cancer, pancreatic cancer and with other biologic and small molecules in trials for additional solid cancers such as gastric cancers, melanoma and unresectable hepatocellular carcinoma.

Further anti-PD-L1 antibodies have been tested in clinical trials, including BMS-936559 and others are in preclinical testing.

However, few anti-LAG-3 therapies are currently in clinical testing and none have been approved for therapy so there remains a need to develop additional molecules which target LAG-3. Whilst there are some anti-PD-L1 therapeutics in development, current data shows that overall treatment with anti-PD-L1 monotherapy results in a response in less than 50% of cancer patients. Thus, there remains a need in the art for additional molecules which can target LAG-3 and/or PD-L1 and which find application in cancer therapy.

STATEMENTS OF INVENTION

Anti-PD-1 and anti-PD-L1 antibodies are predominantly involved in breaking immune tolerance and activating an anti-tumour immune response. LAG-3, expressed on T cells following activation, and constitutively expressed on exhausted T cells, further maintains these cells in a suppressive state. Blockade of LAG-3, when employed in combination with other established immune suppressive molecules (i.e.: PD-1, PD-L1) has also been shown to provide a synergistic improved immune response in murine tumour models (Woo et al, 2012). The present inventors postulated that therapies targeting both of these pathways simultaneously will directly address mechanisms which promote and maintain T cell exhaustion. In addition, the inventors expect that targeting LAG-3 may suppress antigen presentation through the action of LAG-3 expressing regulatory T cells on APCs and the published research documenting down-regulation of CD86 (Grosso et al, 2013). Blocking this interaction is expected to maintain antigen presentation, while blocking PD-L1 signalling is expected to break tolerance, resulting in a significant anti-tumour response when both pathways are inhibited at the same time.

Published data on anti-LAG-3 and anti-PD-L1 antibody combinations is limited though there are some results from preclinical syngeneic mouse tumour and viral load models. In a murine model of myeloma, a combination of anti-PD-L1 and anti-LAG-3 blocking antibodies was administered following low dose whole body irradiation and improved survival rates to greater than 80% (Jing et al, 2015). No evidence of systemic or organ-specific autoimmunity was observed. LAG-3 and PD-1 knock-out mice showed markedly increased survival from and clearance of multiple transplantable tumours (Woo et al, 2012).

The present inventors postulated that bispecific antibodies which bind to both LAG-3 and PD-L1 would confer a number of advantages over the combination of monoclonal antibodies against these antigens, including:

1. Directed Therapy

Activated T cells express LAG-3 in the lymph nodes. One part of the anti-LAG-3/PD-L1 bispecific antibody targets primed LAG-3-positive T cells in the lymph node, which then traffic to the site of the tumour, transporting the bispecific antibody. Once within the tumour microenvironment, T cells carrying the bispecific antibody are able to immediately engage and block PD-L1 on tumour cells via the anti-PD-L1 portion. Consequently, all T cells traveling to the tumour site would be resistant to both LAG-3 and PD-L1/PD-1 signalling.

2. Bridging

Primed CD8 positive T cells encounter tumour antigens within the tumour microenvironment, where they respond by killing the tumour cell in the absence of suppressive signals. Bispecific antibodies are expected to be superior over combinations of individual monoclonal therapies by maintaining or prolonging this contact between T cells and tumour cells. Signal strength in the activation of T cells is essential, which in the case of presented antigen in cancers may be key (Engels et al, 2013) and the presence of a bispecific anti-LAG-3/PD-L1 antibody bound to targets on APC or cancer cells is expected to increase the time in which the T cells can successfully recognise antigen and become activated.

3. Localisation

In areas of inflammation and ongoing immune responses, PD-L1 expression is significantly increased because of localised IFN-γ release. This is true whether on target cancer cells, tumour-associated macrophages (TAM), or repeated stimulation of T cell populations. A bispecific antibody that antagonises PD-L1 and LAG-3 is expected to localise and concentrate to the areas of greatest PD-L1 expression in the tumour whilst allowing the anti-LAG-3 portion to bind and prevent LAG-3-mediated suppression of T cells.

Following an extensive screening and affinity maturation programme, the present inventors were able to identify ten specific binding members comprising a binding site specific for LAG-3 in the CH3 domain of the molecule. These molecules were shown to have a high affinity for both human and cynomolgus LAG-3. The high affinity for human LAG-3 is expected to be advantageous in the treatment of e.g. cancers containing tumour-infiltrating lymphocytes (TILs) expressing LAG-3 in human patients, while the high affinity for cynomolgus LAG-3, which is comparable to the affinity for human LAG-3, is expected to be useful in the evaluation of the properties of the specific binding members in cynomolgus monkey disease models. The reason for this is that the results obtained are more likely to be predictive of the effects of the specific binding member in human patients than when a molecule which has a higher variability in its affinity for human and cynomolgus LAG-3 is tested in cynomolgus monkey models.

The specific binding members were also shown to have high activity in a T cell activation assay, which is expected to be predictive of improved efficacy in human patients through enhanced inhibition of LAG-3.

The present inventors further combined these specific binding members comprising a binding site specific for LAG-3 in the CH3 domain with an antibody Fab domain comprising a CDR-based antigen binding site for PD-L1 to create bispecific antibody molecules comprising binding sites for both LAG-3 and PD-L1, which are expected to have the advantages detailed above. Surrogate murine versions of these antibody molecules which bind to murine LAG-3 and murine PD-L1 were also prepared by the inventors and shown to be capable of significantly inhibiting tumour growth in syngeneic mouse models of cancer. In particular, use of these surrogate murine molecules demonstrated there is a synergistic effect on tumour growth suppression when an antibody molecule comprising binding sites for both LAG-3 and PD-L1 is administered to mice in the mouse models tested. Based on the similar mechanism of action of mouse and human LAG-3 and PD-L1 in the tumour environment, murine studies that show efficacy in diminishing tumour burden are expected to translate into clinical therapeutic benefits in human cancer patients. Based on these results, it is therefore expected that the antibody molecules of the invention will show a superior effect in the treatment of cancer in human patients, in particular in suppressing tumour growth, than, for example, administration of two separate molecules which bind LAG-3 and PD-L1, respectively.

Thus, in a first aspect the present invention provides an antibody molecule which binds to both to PD-L1 and LAG-3. Specifically, these antibodies comprise:

(i) a CDR-based antigen binding site for PD-L1; and
(ii) a LAG-3 antigen binding site located in, or engineered into, two or more structural loops of a CH3 domain of the antibody molecule. The LAG-3 binding site preferably comprises the amino acid sequences WDEPWGED (SEQ ID NO: 1) and PYDRWVWPDE. (SEQ ID NO: 3).

The antibody molecule preferably comprises the amino acid sequence set forth in SEQ ID NO: 1 in the AB loop, and the amino acid sequence set forth in SEQ ID NO: 3 in the EF loop of the CH3 domain.

Thus, in a first aspect, the present invention provides an antibody molecule which binds to programmed death-ligand 1 (PD-L1) and lymphocyte-activation gene 3 (LAG-3). The antibody molecule preferably comprises (i) a CDR-based antigen binding site for PD-L1; and (ii) a LAG-3 antigen binding site located in a CH3 domain of the antibody molecule.

The LAG-3 binding site preferably comprises the amino acid sequences WDEPWGED (SEQ ID NO: 1) and PYDRWVWPDE (SEQ ID NO: 3). The amino acid sequence WDEPWGED is preferably located in a first structural loop of the CH3 domain and the amino acid sequence PYDRWVWPDE is preferably located in a second structural loop of the CH3 domain.

For example, the LAG-3 antigen-binding site may be located in a structural loop region of a CH3 domain of the antibody molecule, wherein the structural loop region preferably comprises two or more structural loops, and wherein the LAG-3 binding site preferably comprises the amino acid sequences WDEPWGED (SEQ ID NO: 1) and PYDRWVWPDE (SEQ ID NO: 3).

As a further example, the LAG-3 antigen-binding site may be engineered into two or more structural loops of a CH3 domain of the antibody molecule, wherein the LAG-3 binding site preferably comprises the amino acid sequences WDEPWGED (SEQ ID NO: 1) and PYDRWVWPDE (SEQ ID NO: 3).

As mentioned above, the sequences of the LAG-3 binding site are preferably located in two or more structural loops of the CH3 domain of the antibody molecule. In a preferred embodiment the LAG-3 antigen-binding site comprises the amino acid sequence set forth in SEQ ID NO: 1 in the AB loop, and the amino acid sequence set forth in SEQ ID NO: 3 in the EF loop of the CH3 domain.

The amino acid sequence set forth in SEQ ID NO: 1 is preferably located at residues 11 to 18 of the CH3 domain; and/or the amino acid sequence set forth in SEQ ID NO: 3 is located at residues 92 to 101 of the CH3 domain; wherein the amino acid residue numbering is according to the ImMunoGeneTics IMGT) numbering scheme.

The LAG-3 antigen-binding site of the antibody molecule may further comprise one of the following sequences, preferably in the CD loop of the CH3 domain of the antibody molecule:

(i)
SNGQPENNY; (SEQ ID NOS 2, 8 and 18)

(ii)
SNGQPEDNY; (SEQ ID NO: 13)

(iii)
SNGYPEIEF; (SEQ ID NO: 23)

(iv)
SNGIPEWNY; (SEQ ID NO: 28)

(v)
SNGYAEYNY; (SEQ ID NO: 33)

(vi)
SNGYKEENY; (SEQ ID NO: 38)

(vii)
SNGVPELNV; (SEQ ID NO: 43)
or (viii)
SNGYQEDNY. (SEQ ID NO: 48)

Preferably, the LAG-3 antigen-binding site of the antibody molecule further comprise one of the following sequences, preferably in the CD loop of the CH3 domain of the antibody molecule: the amino acid sequence set forth in SEQ ID NO: 2, 28, or 38 in the CD loop of the CH3 domain. More preferably, the LAG-3 antigen-binding site of the antibody molecule further comprises the amino acid sequence set forth in SEQ ID NO: 2 in the CD loop of the CH3 domain The amino acid sequence set forth in SEQ ID NO: 2, 8, 13, 18, 23, 28, 33, 38, 43, or 48 is preferably located at residues 43 to 78 of the CH3 domain of the antibody molecule, wherein the residues are numbered according to the IMGT numbering scheme.

The sequence of the CH3 domain of the antibody molecule, other the sequences of the LAG-3 antigen-binding site, is not particularly limited. Preferably, CH3 domain is a human immunoglobulin G domain, such as a human IgG1, IgG2, IgG3, or IgG4 CH3 domain, most preferably a human IgG1 CH3 domain. The sequences of human IgG1, IgG2, IgG3, or IgG4 CH3 domains are known in the art.

In a preferred embodiment, the antibody molecule comprises the CH3 domain set forth in SEQ ID NO: 5, 10, 15, 20, 25, 30, 35, 40, 45, or 50, more preferably the CH3 domain set forth in SEQ ID NO: 5, 30, or 40, most preferably the CH3 domain set forth in SEQ ID NO: 5. Alternatively, the antibody molecule may comprise a CH3 domain with an amino acid sequence which has at least 70%, at least 75%, at least 80%, at least 85%, at least 90%, at least 95%, at least 96%, at least 97%, at least 98%, or at least 99% sequence identity to SEQ ID NO: 5, 10, 15, 20, 25, 30, 35, 40, 45, or 50, preferably SEQ ID NO: 5, 30, or 40, more preferably SEQ ID NO: 5.

The antibody molecule may further comprise a CH2 domain. The CH2 domain is preferably located at the N-terminus of the CH3 domain, as in the case in a human IgG molecule. The CH2 domain of the antibody molecule is preferably the CH2 domain of human IgG1, IgG2, IgG3, or IgG4, more preferably the CH2 domain of human IgG1. The sequences of human IgG domains are known in the art. In a preferred embodiment, the antibody molecule comprises an IgG CH2 domain with the sequence set forth in SEQ ID NO: 53 or SEQ ID NO: 54, or a CH2 domain with an amino acid sequence which has at least 70%, at least 75%, at least 80%, at least 85%, at least 90%, at least 95%, at least 96%, at least 97%, at least 98%, or at least 99% sequence identity to SEQ ID NO: 53 or SEQ ID NO: 54.

In a preferred embodiment, the antibody molecule comprises the sequence set forth in SEQ ID NO: 6, 7, 11, 12, 16, 17, 21, 22, 26, 27, 31, 32, 36, 37, 41, 42, 46, 47, 51, or 52, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 6, 7, 11, 12, 16, 17, 21, 22, 26, 27, 31, 32, 36, 37, 41, 42, 46, 47, 51, or 52. More preferably, the antibody molecule comprises the sequence set forth in SEQ ID NO: 6, 7, 31, 32, 41, or 42, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 6, 7, 31, 32, 41, or 42. Yet more preferably, the antibody molecule comprises the sequence set forth in SEQ ID NO: 6 or 7, or a sequence which has at least 70%, at least 75%, at least 80%, at least 85%, at least 90%, at least 95%, at least 96%, at least 97%, at least 98%, or at least 99% sequence identity to the sequence set forth in SEQ ID NO: 6 or 7.

In a preferred embodiment, the antibody molecule is a human immunoglobulin G molecule, such as a human IgG1, IgG2, IgG3 or IgG4 molecule, more preferably a human IgG1 molecule. The sequences of human immunoglobulin G molecules is known in the art and introducing a CH3 domain or CH3 domain sequence as disclosed here into such a molecule would not present any difficulty to the skilled person.

The antibody molecule preferably comprise the CDRs of the VH and/or VL domains set forth in SEQ ID NOs 92 and 93. Methods for determining CDR sequence in a given VH or VL domain are known in the art and include the Kabat and IMGT numbering systems. More preferably, the antibody molecule preferably comprise one or more, two or more, three or more, four or more, five or more, or all six of the complementarity determining regions set forth in SEQ ID NOs 86 to 91. Preferably, the antibody molecule comprises the VH and/or VL domains set forth in SEQ ID NOs 92 and 93, respectively.

In a preferred embodiment, the antibody molecule comprises the heavy chain sequence set forth in any one of SEQ ID NOs: 94 to 113, or a heavy chain with an amino acid sequence which has at least 70%, at least 75%, at least 80%, at least 85%, at least 90%, at least 95%, at least 96%, at least 97%, at least 98%, or at least 99% sequence identity to any one of SEQ ID NOs: 94 to 113, provided the VH domain of the heavy chain sequence remains unchanged. More preferably, the antibody molecule comprises the heavy chain sequence set forth in any one of SEQ ID NOs: 94, 95, 104, 105, 108, and 109, or a heavy chain with an amino acid sequence which has at least 70%, at least 75%, at least 80%, at least 85%, at least 90%, at least 95%, at least 96%, at least 97%, at least 98%, or at least 99% sequence identity to any one of SEQ ID NOs: 94, 95, 104, 105, 108, and 109, provided the VH domain of the heavy chain sequence remains unchanged. Yet more preferably, the antibody molecule comprises the heavy chain sequence set forth in SEQ ID NO: 94 or 95, or a heavy chain with an amino acid sequence which has at least 70%, at least 75%, at least 80%, at least 85%, at least 90%, at least 95%, at least 96%, at least 97%, at least 98%, or at least 99% sequence identity to SEQ ID NOs: 94 or 95, provided the VH domain of the heavy chain sequence remains unchanged.

In a further preferred embodiment, the antibody molecule may in addition, or alternatively, comprise the light chain sequence set forth in SEQ ID NO: 116, or a light chain with an amino acid sequence which has at least 70%, at least 75%, at least 80%, at least 85%, at least 90%, at least 95%, at least 96%, at least 97%, at least 98%, or at least 99% sequence identity to SEQ ID NO: 116, provided the VL domain of the light chain sequence remains unchanged.

The antibody molecule is preferably capable of simultaneously binding to PD-L1 and LAG-3. The PD-L1 and LAG-3 may, for example, be present on two different cells. Without wishing to be limited by theory, it is thought that this results in cross-linking between cells and internalization of PD-L1 and/or LAG-3 making them unavailable for stimulation.

The present inventors have shown that an antibody molecule comprising (i) a CDR-based antigen binding site for PD-L1; and (ii) a LAG-3 antigen binding site located in a CH3 domain of the antibody molecule, in accordance with the present invention, FS18-7-9/84G09, surprisingly mediated Complement Dependent Cytotoxicity (CDC) of PD-L1 expressing cells but not of LAG-3 expressing cells, even when a mixture of LAG-3 and PD-L1 expressing cells were present in the sample. This property is expected to be useful where, as is the case with FS18-7-9/84G09, the CDR-based antigen binding of the antibody molecule targets a tumour cell and the binding site located in a constant domain of the antibody molecule targets an immune cell, as the immune cell would be protected from CDC mediated by binding to the antibody molecule, while tumour cells would be subject to CDC.

Thus, in a further embodiment, the present invention relates to an antibody molecule which binds to tumour antigen and an immune cell antigen, wherein the antibody molecule comprises:
  (i) a CDR-based antigen binding site for a tumour antigen; and
  (ii) an antigen binding site for an immune cell antigen located in a constant domain, preferably a CH3 or CH2 domain, more preferably a CH3 domain, of the antibody molecule,
  wherein the antibody molecule does not mediate, or does not mediate significant, complement dependent cytotoxicity of an immune cell comprising said immune cell antigen when said immune cell is bound by the antibody molecule.

Preferably, the antibody molecule further mediates complement dependent cytotoxicity of a tumour cell comprising said tumour antigen when said tumour cell is bound by the antibody molecule.

Methods for measuring CDC of an antibody molecule are known in the art and described herein.

The present inventors have further shown that an antibody molecule comprising (i) a CDR-based antigen binding site for PD-L1; and (ii) a LAG-3 antigen binding site located in a CH3 domain of the antibody molecule, in accordance with the present invention, FS18-7-9/84G09, surprisingly mediated low Antibody Dependent Cellular Cytotoxicity (ADCC) of LAG-3 expressing cells compared with ADCC of PD-L1 expressing cells. This property is again expected to be useful where, as is the case with FS18-7-9/84G09, the CDR-based antigen binding of the antibody molecule targets a tumour cell and the binding site located in a constant domain of the antibody molecule targets an immune cell, as the immune cell would be subjected to lower ADCC than a tumour cell bound by the antibody.

As explained herein, mutations for reducing or abrogating ADCC activity of antibody molecules are known in the art. One such mutations is the LALA mutation described herein. It was unexpectedly found that FS18-7-9/84G09 has low ADCC activity towards LAG-3-expressing cells. Where it is not necessary to completely abrogate ADCC activity, this may represent an advantage.

Thus, in a further embodiment, the present invention relates to an antibody molecule which binds to tumour antigen and an immune cell antigen, wherein the antibody molecule comprises:
  (i) a CDR-based antigen binding site for a tumour antigen; and
  (ii) an antigen binding site for an immune cell antigen located in a constant domain, preferably a CH3 or CH2 domain, more preferably a CH3 domain, of the antibody molecule, wherein the antibody molecule causes less ADCC with respect to immune cells comprising said immune cell antigen when said immune cells are bound by the antibody molecule than of tumour cells comprising said tumour antigen when said tumour cells are bound by the antibody molecule. Preferably, the antibody molecule does not mediate, or not mediate significant, ADCC of an immune cell comprising said immune cell antigen when said immune cell is bound by the antibody molecule. The antibody molecule may further not mediate, or not mediate significant, complement dependent cytotoxicity of an immune cell comprising said immune cell antigen when said immune cell is bound by the antibody molecule and/or may mediate complement dependent cytotoxicity of a tumour cell comprising said tumour antigen when said tumour cell is bound by the antibody molecule.

Methods for measuring ADCC of an antibody molecule are known in the art and described herein.

Various tumour antigens and immune cell antigens are known in the art. The tumour antigen and immune cell antigen are preferably cell-surface antigens. The immune cell antigen is preferably an antigen present on tumour-infiltrating lymphocytes.

The antigen binding site for the immune cell antigen preferably comprises one or more modifications in one or more structural loops of the constant domain of the antibody molecule, such as the AB, CD, and/or EF loop of the constant domain. For example, the binding site may be a LAG-3 binding site as herein described.

The antibody molecule of the invention may be conjugated to an immune system modulator, cytotoxic molecule, radioisotope, or detectable label. The immune system modulator may be cytotoxic molecule is a cytokine.

The present invention also provides a nucleic acid encoding an antibody molecule of the invention, as well as a vector comprising such a nucleic acid.

A recombinant host cell comprising a nucleic acid or the vector of the invention is also provided. Such a recombinant host cell may be used to produce an antibody molecule. Thus, also provided is a method of producing an antibody molecule of the invention, the method comprising culturing the recombinant host cell under conditions for production of the antibody molecule. The method may further comprise a step of isolating and/or purifying the antibody molecule.

The antibody molecules of the present invention are expected to find application in therapeutic applications, in particular therapeutic applications in humans, such as cancer treatment. Thus, also provided is a pharmaceutical composition comprising an antibody molecule according to the invention and a pharmaceutically acceptable excipient.

The present invention also provides an antibody molecule of the invention, for use in a method of treating cancer in a patient. Also provided is a method of treating cancer in a patient, wherein the method comprises administering to the patient a therapeutically effective amount of an antibody molecule according to the invention. Further provided is the use of an antibody molecule according to the invention for use in the manufacture of a medicament for the treatment of cancer in a patient. The treatment may further comprise administering an anti-tumour vaccine and/or a chemotherapeutic agent to the patient.

BRIEF DESCRIPTION OF THE FIGURES

FIG. 1: A shows a sequence alignment of the nine Fcabs identified following the second affinity maturation, FS18-7-32; FS18-7-33; FS18-7-36; FS18-7-58; FS18-7-62; FS18-7-65; FS18-7-78; FS18-7-88; and FS18-7-95, against the parental Fcab, FS18-7-9. B shows the percentage sequence identity of each of these Fcabs with the sequence of the parental Fcab, FS18-7-9.

FIG. 2 shows representative plots of IL-2 release, which is indicative of T cell activation, in the panel of cell lines treated with mAb$^2$ FS18-7-9/84G09 (FIG. 2A-C), or FS18-7-62/84G09 or FS18-7-78/84G09 (FIGS. 2D-F), and control antibodies. FIG. 2A: The assay with LAG-3 and PD-L1 required inhibition of both targets (FS18-7-9/84G09LALA, FS18-7-9/4420LALA+84G09, 25F7+84G09LALA or 25F7+S1LALA) to have activation. FIG. 2B: The assay with LAG-3 only required inhibition of LAG-3 for activation (FS18-7-9/84G09LALA, FS18-7-9/4420LALA+84G09, 25F7+84G09LALA, 25F7+S1LALA, 25F7, FS18-7-9/4420 LALA). FIG. 2C: The assay with PD-L1 only required the inhibition of PD-L1 for activation (FS18-7-9/84G09LALA, FS18-7-9/4420LALA+84G09, 25F7+84G09LALA, 25F7+S1LALA, 84G09LALA). FIG. 2D: The assay with LAG-3 and PD-L1 required inhibition of both targets (FS18-7-62/84G09LALA, FS18-7-78/84G09LALA, FS18-7-62/4420LALA+84G09, FS18-7-78/4420LALA+84G09, 25F7+84G09LALA or 25F7+S1LALA) to have activation. Figure E: The assay with only LAG-3 required inhibition of LAG-3 for activation (FS18-7-62/84G09LALA, FS18-7-62/4420LALA, FS18-7-78/84G09LALA, FS18-7-78/4420LALA, FS18-7-62/4420LALA+84G09, FS18-7-78/4420LALA+84G09, 25F7+84G09LALA or 25F7+S1LALA). FIG. 2F: The assay with only PD-L1 required the inhibition of PD-L1 for activation (FS18-7-62/84G09LALA, FS18-7-78/84G09LALA, FS18-7-62/4420LALA+84G09, FS18-7-78/4420LALA+84G09, 25F7+84G09LALA or 25F7+S1LALA).

DETAILED DESCRIPTION

Figure 2:
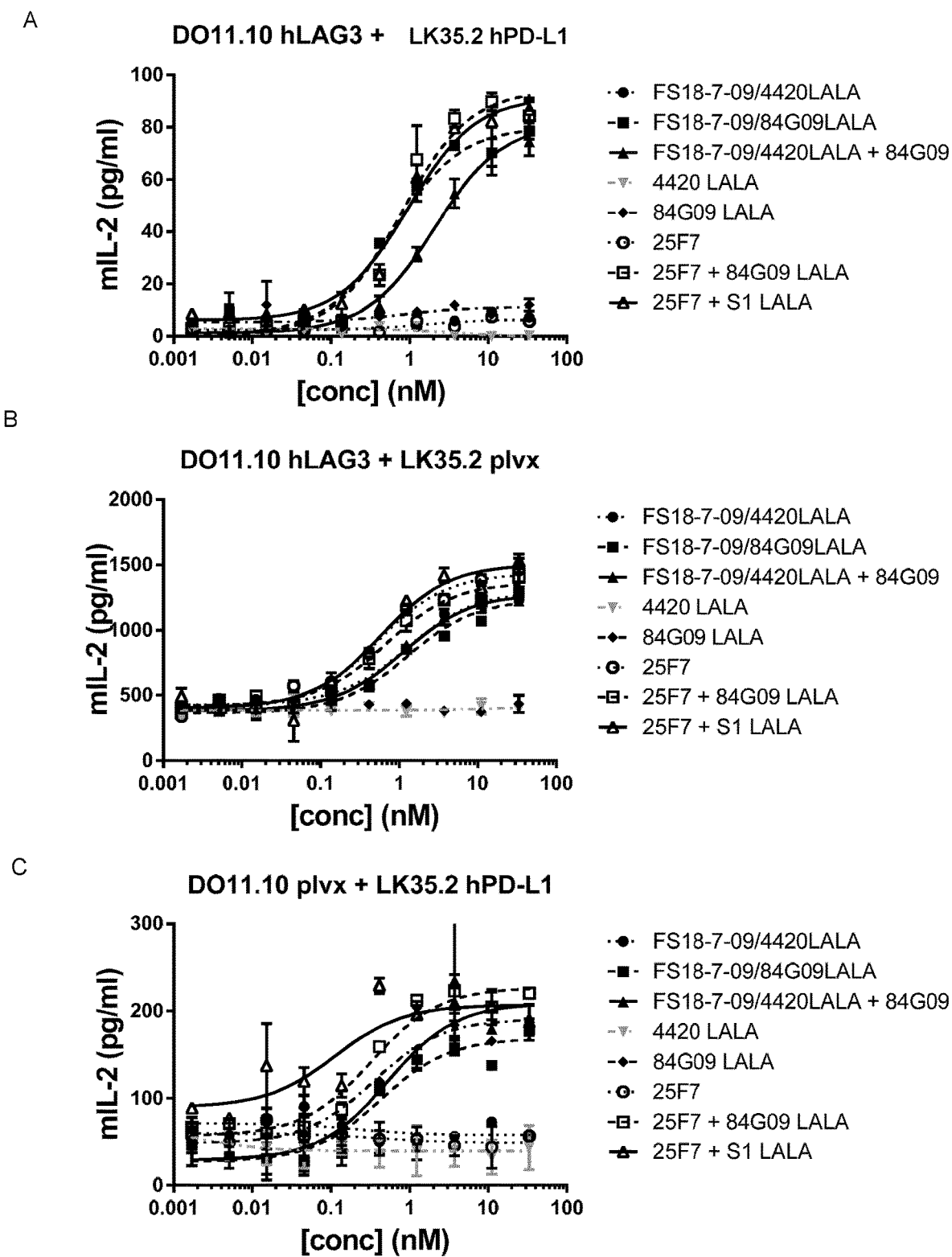
FIG. 2 shows the results of a T cell activation assay. Specifically.
Figure 2:
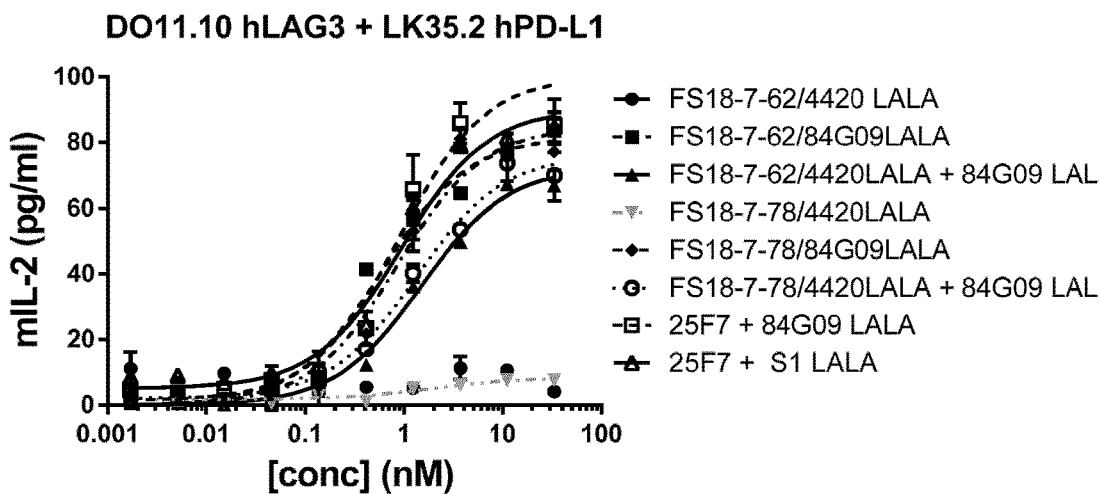
Figure 2:
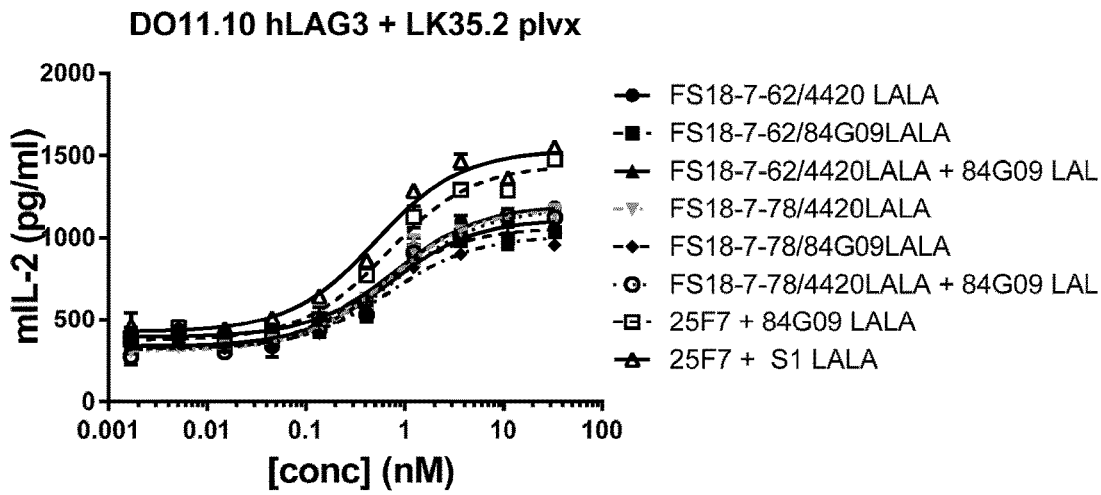
Figure 2:
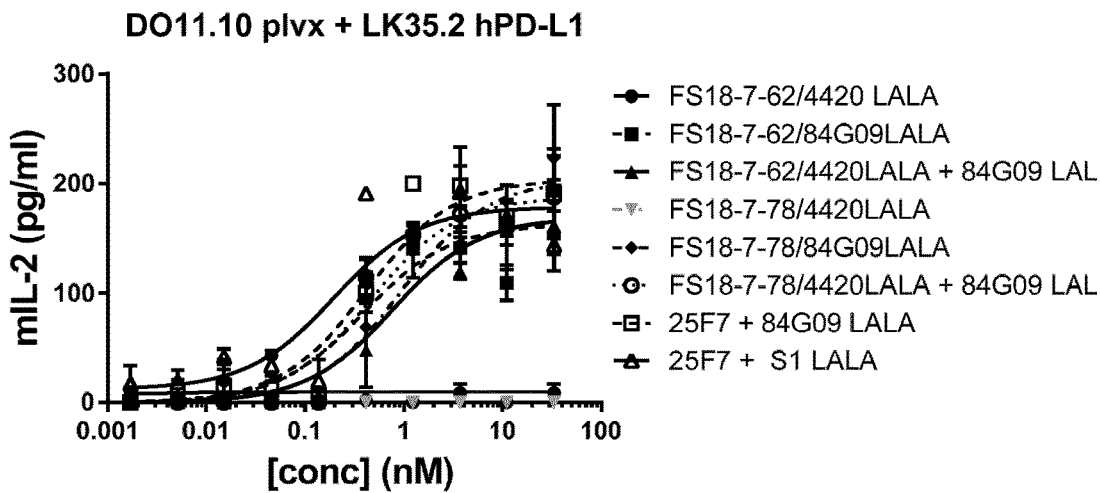

The present invention relates to antibody molecules which bind both to PD-L1 and LAG-3. Specifically, the antibody molecules of the present invention comprise a CDR-based antigen binding site for PD-L1 and a LAG-3 antigen binding site located in a constant domain of the antibody molecule. The terms "PD-L1" and "LAG-3" may refer to human PD-L1 and human LAG-3, murine PD-L1 and murine LAG-3, and/or cynomologus monkey PD-L1 and cynomologus monkey LAG-3, unless the context requires otherwise. Preferably the terms "PD-L1" and "LAG-3" refer to human PD-L1 and human LAG-3, unless the context requires otherwise.

The term "antibody molecule" describes an immunoglobulin whether natural or partly or wholly synthetically produced. The antibody molecule may be human or humanised. The antibody molecule is preferably a monoclonal antibody molecule. Examples of antibodies are the immunoglobulin isotypes, such as immunoglobulin G, and their isotypic subclasses, such as IgG1, IgG2, IgG3 and IgG4, as well as fragments thereof.

The term "antibody molecule", as used herein, thus includes antibody fragments, provided said fragments comprise a CDR-based antigen binding site for PD-L1 and a LAG-3 antigen binding site located in a constant domain, such as a CH1, CH2, or CH3 domain, preferably a CH3 domain, of the antibody molecule. Unless the context requires otherwise, the term "antibody molecule", as used herein, is thus equivalent to "antibody molecule or fragment thereof".

It is possible to take monoclonal and other antibodies and use techniques of recombinant DNA technology to produce other antibodies or chimeric molecules which retain the specificity of the original antibody. Such techniques may involve introducing the CDRs, or variable regions, and/or the constant domain sequences providing the LAG-3 antigen binding site, into a different immunoglobulin. Introduction of the CDRs of one immunoglobulin into another immunoglobulin is described for example in EP-A-184187, GB 2188638A or EP-A-239400. Similar techniques could be employed for the relevant constant domain sequences. Alternatively, a hybridoma or other cell producing an antibody molecule may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

An example of an antibody fragment comprising both CDR sequences and CH3 domain is a minibody, which comprises an scFv joined to a CH3 domain (Hu et al. (1996), Cancer Res., 56(13):3055-61).

The antibody molecule of the present invention binds to PD-L1 and LAG-3. Binding in this context may refer to specific binding. The term "specific" may refer to the situation in which the antibody molecule will not show any significant binding to molecules other than its specific binding partner(s), here PD-L1 and LAG-3. The term "specific" is also applicable where the antibody molecule is specific for particular epitopes, such as epitopes on PD-L1 and LAG-3, that are carried by a number of antigens in which case the antibody molecule will be able to bind to the various antigens carrying the epitope.

LAG-3 shares 40% sequence identity with CD4, its most closely related protein. The present inventors tested the FS18-7-9 Fcab, which comprises the amino acid sequences set forth in SEQ ID NOs 1 to 3, for binding to CD4. The FS18-7-9 Fcab showed no binding to CD4, demonstrating that this molecule binds LAG-3 specifically. Thus, in a preferred embodiment, the LAG-3 binding site of an antibody molecule of the present invention does not bind, or does not show any significant binding, to CD4.

An antibody molecule of the invention preferably comprises a LAG-3 antigen binding site. The LAG-3 antigen binding site is located in a constant domain of the antibody molecule, such as a CH1, CH2, CH3 or CH4 domain. Preferably, the LAG-3 antigen binding site is located in the CH3 domain of the antibody molecule. The LAG-3 binding site preferably comprises the amino acid sequences WDEPWGED (SEQ ID NO: 1) and PYDRWVWPDE. (SEQ ID NO: 3). These sequences were present in all of the lead anti-LAG-3 Fcab clones identified by the present inventors following an extensive screening and characterisation program as described in the examples.

The amino acid sequences set forth in SEQ ID NOs 1 and 2 are preferably located in structural loops of the constant domain of the antibody molecule. The introduction of sequences into the structural loop regions of antibody constant domains to create new antigen-binding sites is described, for example, in WO2006/072620 and WO2009/132876.

The structural loops of antibody constant domains include the AB, CD and EF loops. In the CH3 domain, the AB, CD, and EF loops are located at residues 11-18, 43-78 and 92-101 of the CH3 domain, where the amino acid residue numbering is according to the ImMunoGeneTics (IMGT) numbering scheme. The amino acid sequence set forth in SEQ ID NO: 1 is preferably located in the AB loop of the constant domain. The amino acid sequence set forth in SEQ ID NO: 3 is preferably located in the EF loop of the constant domain. More preferably, the amino acid sequence set forth in SEQ ID NO: 1 is located at residues 11 to 18 of the CH3 domain; and/or the amino acid sequence set forth in SEQ ID NO: 3 is located at residues 92 to 101 of the CH3 domain, wherein the amino acid residue numbering is according to the IMGT numbering scheme.

In addition, the antibody molecule preferably comprises the amino acid sequence set forth in SEQ ID NO: 2, 8, 13, 18, 23, 28, 33, 38, 43, or 48, more preferably SEQ ID NO: 2, 28, or 38, yet more preferably SEQ ID NO: 2, in a structural loop of a constant domain of the antibody molecule. The structural loop is preferably the CD loop and the constant domain is preferably the CH3 domain. The amino acid sequence set forth in SEQ ID NO: 2, 8, 13, 18, 23, 28, 33, 38, 43, or 48 is preferably located at residues 43 to 78 of the CH3 domain, wherein the amino acid residue numbering is according to the IMGT numbering scheme.

An antibody molecule of the invention may further comprise a glutamic acid residue (E) at position 36 and/or a tyrosine residue (Y) at position 85.2 of the CH3 domain (as shown in FIG. 1A), wherein the amino acid residue numbering is according to the IMGT numbering scheme. In particular, an antibody molecule which comprises the CD structural loop region set forth in SEQ ID NO: 8 preferably further comprises a glutamic acid residue (E) at position 36 of the CH3 domain. Similarly, an antibody molecule which comprises the CD structural loop region set forth in SEQ ID NO: 18 preferably further comprises a tyrosine residue (Y) at position 85.2 of the CH3 domain.

In a preferred embodiment, the antibody molecule of the invention comprises a CH3 domain which comprises, has, or consists of the sequence set forth in SEQ ID NO: 5, 10, 15, 20, 25, 30, 35, 40, 45, or 50, preferably a CH3 domain with the sequence set forth in SEQ ID NO: 5, 30, or 40, more preferably, a CH3 domain with the sequence set forth in SEQ ID NO: 5.

The antibody molecule of the invention may comprise a CH3 domain which comprises, has, or consists of the sequence set forth in SEQ ID NO: 5, 10, 15, 20, 25, 30, 35, 40, 45, or 50, wherein the CH3 domain sequence further comprises a lysine residue (K) at the immediate C-terminus of the sequence shown in SEQ ID NO: 5, 10, 15, 20, 25, 30, 35, 40, 45, or 50. Thus, for example, the antibody molecule of the invention may comprise a CH3 domain which comprises, has, or consists of the sequence set forth in SEQ ID NO: 5 with a lysine residue at the C-terminus of the sequence shown in SEQ ID NO: 5. The sequence of such a CH3 domain would then be as follows:

(SEQ ID NO: 135)
GQPREPQVYTLPPSWDEPWGEDVSLTCLVKGFYPSDIAVEWESNGQPEN

NYKTTPPVLDSDGSFFLYSKLTVPYDRWVWPDEFSCSVMHEALHNHYTQ

KSLSLSPGK

In addition, the antibody molecule of the invention may comprise a CH2 domain of an immunoglobulin G molecule, such as a CH2 domain of an IgG1, IgG2, IgG3, or IgG4 molecule. Preferably the antibody molecule of the invention comprises a CH2 domain of an IgG1 molecule. The CH2 domain may have the sequence set forth in SEQ ID NO: 53.

The CH2 domain of the antibody molecule may comprise a mutation to reduce or abrogate binding of the CH2 domain to one or more Fc γ receptors, such as FcγRI, FcγRIIa, FcγRIIb, FcγRIII and/or to complement. CH2 domains of human IgG domains normally bind to Fc γ receptors and complement and the inventors postulate that reduced binding to Fc γ receptors will reduce the antibody-dependent cell-mediated cytotoxicity (ADCC) and reduced binding to complement will reduce the complement-dependent cytotoxicity (CDC) activity of the antibody molecule. Mutations for reduce or abrogate binding of the CH2 domain to one or more Fc γ receptors and complement are known and include the "LALA mutation" described in Bruhns, et al. (2009) and Xu et al. (2000). Thus, the antibody molecule may comprise a CH2 domain, wherein the CH2 domain comprises alanine residues at positions 4 and 5 of the CH2 domain, wherein the numbering is according to the IMGT numbering scheme. For example, the antibody molecule comprises an IgG1 CH2 domain which comprises, has, or consists of the sequence set forth in SEQ ID NO: 54.

The antibody molecule of the present invention comprises a CDR-based antigen binding site for PD-L1. The term "CDR-based antigen binding site" refers to the antigen-binding site of an antibody molecule variable region which is composed of six CDRs. The preparation of antibody molecules against PD-L1, and determination of the CDR sequences of such antibody molecules, is well within the capabilities of the skilled person and many suitable techniques are known in the art.

Preferably, the antibody molecule of the invention comprises the HCDR3 of antibody 84G09. The HCDR3 is known to play a role in determining the specificity of an antibody molecule (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

The antibody molecule may further comprise the HCDR1, HCDR2, LCDR1, LCDR2 and/or LCDR3 of antibody 84G09. The skilled person would have no difficulty in determining the sequences of the CDRs from the VH and VL domain sequences of antibody 84G09 shown in SEQ ID NOs 92 and 93, respectively. The CDR sequences may, for example, be determined according to Kabat (Kabat, E. A. et al., (1991)) or the IMGT numbering scheme.

The sequences of the HCDR1, HCDR2, HCDR3, LCDR1, LCDR2 and LCDR3 of antibody 84G09, according to the IMGT numbering scheme, are set out in SEQ ID NOs 86, 87, 88, 89, 90, and 91, respectively.

The sequences of the HCDR1, HCDR2, HCDR3, LCDR1, LCDR2 and LCDR3 of antibody 84G09, according to Kabat, are set out in SEQ ID NOs 136, 137, 138, 139, 140, and 141, respectively.

The antibody may also comprise the VH and/or VL domain of antibody 84G09. The VH and VL domain sequences of antibody 84G09 shown in SEQ ID NOs 92 and 93, respectively.

In a preferred embodiment, the antibody molecule of the invention comprises (i) a CDR-based antigen binding site for PD-L1 comprising the HCDR1, HCDR2, HCDR3, LCDR1, LCDR2 and LCDR3 sequences of antibody 84G09, and (ii) a LAG-3 antigen binding site located in a CH3 domain of the antibody molecule, wherein the LAG-3 binding site comprises the amino acid sequences set forth in SEQ ID NOs 1 and 3, and an amino acid sequence selected from the group consisting of: SEQ ID NOs 2, 8, 13, 18, 23, 28, 33, 38, 43, and 48.

More preferably, the antibody molecule of the invention comprises (i) a CDR-based antigen binding site for PD-L1 comprising the HCDR1, HCDR2, HCDR3, LCDR1, LCDR2 and LCDR3 sequences of antibody 84G09, and (ii) a LAG-3 antigen binding site located in a CH3 domain of the antibody molecule, wherein the LAG-3 binding site comprises the amino acid sequences set forth in SEQ ID NOs 1 and 3, and an amino acid sequence selected from the group consisting of: SEQ ID NOs 2, 28, and 38.

Yet more preferably, the antibody molecule of the invention comprises (i) a CDR-based antigen binding site for PD-L1 comprising the HCDR1, HCDR2, HCDR3, LCDR1, LCDR2 and LCDR3 sequences of antibody 84G09, and (ii) a LAG-3 antigen binding site located in a CH3 domain of the antibody molecule, wherein the LAG-3 binding site comprises the amino acid sequences set forth in SEQ ID NOs 1, 2 and 3.

In a preferred embodiment, the antibody molecule of the invention comprises a VH domain and a VL domain which comprises, has, or consists of the sequence set forth in SEQ ID NOs 92 and 93, respectively, and a CH3 domain which comprises, has, or consists of the sequence set forth in SEQ ID NO: 5, 10, 15, 20, 25, 30, 35, 40, 45, or 50, preferably a CH3 which comprises, has, or consists of the sequence set forth in SEQ ID NO: 5, 30, or 40, more preferably, a CH3 domain which comprises, has, or consists of the sequence set forth in SEQ ID NO: 5.

In a further preferred embodiment, the antibody molecule comprises a heavy chain which comprises, has, or consists of the sequence set forth in SEQ ID NOs: 94 to 113 and a light chain which comprises, has, or consists of the sequence set forth in SEQ ID NO: 116. More preferably, the antibody molecule comprises a heavy chain which comprises, has, or consists of the sequence set forth in SEQ ID NOs: 94, 95, 104, 105, 108, and 109 and a light chain which comprises, has, or consists of the sequence set forth in SEQ ID NO: 116. Most preferably, the antibody molecule comprises a heavy chain which comprises, has, or consists of the sequence set forth in SEQ ID NO: 94 or 95 and a light chain which comprises, has, or consists of the sequence set forth in SEQ ID NO: 116.

The antibody molecules of the present invention may also comprise variants of the structural loop, CH3 domain, CH2 domain, CH2 and CH3 domain, light chain or heavy chain sequences disclosed herein, provided the VL and VH domains of the light and heavy chain sequences, respectively, remain unchanged. Suitable variants can be obtained by means of methods of sequence alteration, or mutation, and screening. In a preferred embodiment, an antibody molecule comprising one or more variant sequences retains one or more of the functional characteristics of the parent antibody molecule, such as binding specificity and/or binding affinity for LAG-3 and PD-L1. For example, an antibody molecule comprising one or more variant sequences preferably binds to LAG-3 and/or PD-L1 with the same affinity, or a higher affinity, than the (parent) antibody molecule. The parent antibody molecule is an antibody molecule which does not comprise the amino acid substitution(s), deletion(s), and/or insertion(s) which have been incorporated into the variant antibody molecule.

For example, an antibody molecule of the invention may comprise a structural loop, CH3 domain, CH2 domain, CH2 and CH3 domain, light chain or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a structural loop, CH3 domain, CH2 domain, CH2 and CH3 domain, light chain or heavy chain sequence disclosed herein, provided the VL and VH domains of the light and heavy chain sequences, respectively, remain unchanged.

In a preferred embodiment, the antibody molecule of the invention comprises a CH3 domain sequence which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH3 domain sequence set forth in SEQ ID NO: 4, 5, or 135.

In a further preferred embodiment, the antibody molecule of the invention comprises a CH3 and CH2 domain sequence, which has at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 and CH3 domain sequence set forth in SEQ ID NO: 6 or 7.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

An antibody molecule of the invention may also comprise a structural loop, CH3 domain, CH2 domain, CH2 and CH3 domain, light chain or heavy chain sequence which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a structural loop, CH3 domain, CH2 domain, CH2 and CH3 domain, light chain or heavy chain sequence disclosed herein, provided the VL and VH domains of the light and heavy chain sequences, respectively, remain unchanged. In particular, alterations may be made in one or more framework regions of the antibody molecule outside the VH and VL domain sequences.

In a preferred embodiment, the antibody molecule of the invention may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 4, 5, or 135.

In a further preferred embodiment, the antibody molecule of the invention comprises a CH3 and CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 and CH3 domain sequence set forth in SEQ ID NO: 6 or 7.

Also contemplated is an antibody molecule which competes with an antibody molecule of the invention for binding to LAG-3 and/or PD-L1, or which binds to the same epitope on LAG-3 and/or PD-L1 as an antibody molecule of the invention, wherein the antibody molecule comprises both a CDR-based antigen binding site for PD-L1 and a LAG-3 antigen binding site located in a CH3 domain of the antibody molecule. Methods for determining competition for an antigen by two antibodies are known in the art. For example, competition of binding to an antigen by two antibodies can be determined using BIAcore. Methods for mapping the epitope bound by an antibody are similarly known in the art.

The antibody molecule of the invention preferably binds to LAG-3 with an affinity (Kc) of $1 \times 10^{-9}$ M or an affinity which is greater. For example, the antibody molecule of the invention may bind to LAG-3 with an affinity ($K_D$) of $8 \times 10^{-10}$ M, or an affinity which is greater.

Fcabs have a smaller binding interface than monoclonal antibodies as the binding sites of Fcabs form a relatively compact antibody fragment with two binding sites situated in close proximity. In contrast, the Fab arms of a typical mAb are separated by a flexible hinge region. The two antigen binding sites of an Fcab are also spatially close to each other, as compared with those of a typical mAb. Based on this smaller binding interface and reduced flexibility of the two binding sites it was surprising that the anti-LAG-3 Fcabs were able to bind to and inhibit LAG-3 with similar affinity and potency as a monoclonal antibody benchmark.

The antibody molecule of the invention preferably binds to PD-L1 with an affinity ($K_D$) of $1 \times 10^{-9}$ M or an affinity which is greater.

The binding affinity of an antibody molecule to a cognate antigen, such as LAG-3 or PD-L1 can be determined by surface plasmon resonance (SPR), for example. The binding affinity of an antibody molecule to a cognate antigen, such as LAG-3 or PD-L1, expressed on a cell surface can be determined by flow cytometry.

The antibody molecule of the present invention is preferably capable of binding to LAG-3 and PD-L1 expressed on the surface of a cell. The cell is preferably a cancer cell.

The antibody molecule of the present invention is preferably capable of simultaneously binding to LAG-3 and PD-L1. In a preferred embodiment, the antibody molecule of the present invention is capable of simultaneously binding to LAG-3 and PD-L1, wherein the LAG-3 and PD-L1 are expressed on the surface of a single cell, or on the surface of two separate cells.

The antibody molecule of the invention may bind to human LAG-3, murine LAG-3, and/or cynomolgus monkey LAG-3. Preferably, the antibody molecule of the invention binds to human LAG-3. Most preferably, the antibody molecule of the invention binds to human LAG-3 and human PD-L1.

The antibody molecule of the invention comprises (i) a CDR-based antigen binding site for PD-L1; and (ii) a LAG-3 antigen binding site located in a constant domain of the antibody molecule. Antibody molecules which do not comprise a LAG-3 antigen binding site located in a constant domain, such as a CH3 domain, of the antibody molecule thus do not form part of the present invention. Similarly, a molecule which does not comprise a CDR-based antigen binding site for PD-L1 does not form part of the present invention.

The antibody molecule of the present invention may be conjugated to a therapeutic agent or detectable label. In this case, the antibody molecule may be referred to as a conjugate. For example, the antibody molecule may be conjugated to an immune system modulator, cytotoxic molecule, radioisotope, or detectable label. The immune system modulator or cytotoxic molecule may be a cytokine. The detectable label may be a radioisotope, e.g. a non-therapeutic radioisotope.

The antibody molecule may be conjugated to the therapeutic agent or detectable label, by means of a peptide bond or linker, i.e. within a fusion polypeptide comprising said therapeutic agent or detectable label and the antibody molecule or a polypeptide chain component thereof. Other means for conjugation include chemical conjugation, especially cross-linking using a bifunctional reagent (e.g. employing DOUBLE-REAGENTS™ Cross-linking Reagents Selection Guide, Pierce).

The antibody molecule and the therapeutic agent or detectable label may thus be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the antibody molecule and therapeutic or diagnostic agent may be covalently linked. For example by peptide bonds (amide bonds). Thus, the antibody molecule and therapeutic or diagnostic agent may be produced (secreted) as a single chain polypeptide.

The invention also provides isolated nucleic acids encoding the antibodies molecules of the invention. The skilled person would have no difficulty in preparing such nucleic acids using methods well-known in the art. An isolated nucleic acid may be used to express the antibody molecule of the invention, for example, by expression in a bacterial, yeast, insect or mammalian host cell. A preferred host cell is a mammalian cell such as a CHO, HEK or NS0 cell. The nucleic acid will generally be provided in the form of a recombinant vector for expression.

The isolated nucleic acid may, for example, comprise the sequence set forth in SEQ ID NO: 142, 4, 9, 14, 19, 24, 29, 34, 39, 44, or 49, which encode the CH3 domains of FS18-7-9 (CHO codon optimised nucleotide sequence), FS18-7-9 (HEK293-expressed nucleotide sequence), FS18-7-32, FS18-7-33, FS18-7-36, FS18-7-58, FS18-7-62, FS18-7-65, FS18-7-78, FS18-7-88, and FS18-7-95, respectively.

In vitro host cells comprising such nucleic acids and vectors are part of the invention, as is their use for expressing the antibody molecules of the invention, which may subsequently be purified from cell culture and optionally formulated into a pharmaceutical composition. The present invention thus further provides a method of producing the antibody molecule of the invention, comprising culturing the recombinant host cell of the invention under conditions for production of the antibody molecule. Methods for culturing suitable host cells as mentioned above are well-known in the art. The method may further comprise isolating and/or purifying the antibody molecule. The method may also comprise formulating the antibody molecule into a pharmaceutical composition, optionally with a pharmaceutically acceptable excipient or other substance as described below.

PD-L1 is known to be expressed on many cancer cells, while expression of LAG-3 on cancer cells is more limited. Both are expressed on cells of the immune system. In particular, LAG-3 is known to be expressed on exhausted T cells within the tumour environment. In addition, the present inventors have shown that the use of an antibody molecule which binds to both LAG-3 and PD-L1 is effective in suppressing tumour growth in syngeneic mouse models of cancer, and that such antibody molecules are more effective than the administration of two binding molecules which bind LAG-3 and PD-L1, respectively.

Thus, an antibody molecule of the invention may be used in a method of treating cancer in a patient. The patient is preferably a human patient.

Cells of the cancer to be treated using the antibody molecule of the invention may express LAG-3, e.g. on their cell surface. In one embodiment, cells of the cancer to be treated may have been determined to express LAG-3, e.g. on their cell surface. For example, B cell lymphomas have been shown to express LAG-3 on their cell surface. Methods for determining the expression of an antigen on a cell surface are known in the art and include, for example, flow cytometry.

Example 4 below shows that the antibody molecules of the present invention can be used to treat tumours with high levels of LAG-3-expressing immune cells, such as LAG-3-expressing TILs, in mice. Thus, in addition, or alternatively, tumours of the cancer to be treated using the antibody molecule of the invention may comprise LAG-3 expressing immune cells. LAG-3 expressing immune cells, such as LAG-3 expressing TILs, are present between tumour cells in many cancers. In one embodiment, tumours of the cancer to be treated using the antibody molecule of the invention have been determined to contain LAG-3 expressing immune cells. Methods for determining the presence of LAG-3 expressing immune cells in a tumour or in the periphery of the tumour are known in the art.

Example 4 below also shows that the antibody molecules of the present invention can be used to treat tumours which express PD-L1 on their cell surface. Thus, in addition, or alternatively, cells of the cancer to be treated using the antibody molecule of the invention may express PD-L1, e.g. on their cell surface. In addition, or alternatively, tumours of the cancer to be treated may comprise immune cells, such as TILs, that express PD-L1. Cells of the cancer to be treated may have been determined to express PD-L1, e.g. on their cell surface. In addition, or alternatively, tumours of the cancer to be treated may have been determined to contain immune cells, such as TILs, that express PD-L1.

Cell surface expression of LAG-3 and PD-L1 is expected to allow the antibody molecule to bind to LAG-3 and PD-L1 expressed on the surface of the immune cell and/or the cancer cell. This is thought to result in directed therapy, bridging, and localisation of cancer cells and immune cells.

A cancer to be treated using an antibody molecule of the invention may be selected from the group consisting of Hodgkin's lymphoma, non-Hodgkin's lymphoma (such as diffuse large B-cell lymphoma, indolent non-Hodgkin's lymphoma, mantle cell lymphoma, ovarian cancer, prostate cancer, colorectal cancer, fibrosarcoma, renal cell carcinoma, melanoma, pancreatic cancer, breast cancer, glioblastoma multiforme, lung cancer (such as non-small cell lung cancer), head and neck cancer (such as head and neck squamous cell carcinoma), stomach cancer (gastric cancer), bladder cancer, cervical cancer, uterine cancer, vulvar cancer, testicular cancer, penile cancer, leukemia (such as chronic lymphocytic leukemia, myeloid leukemia, acute lymphoblastoid leukaemia, or chronic lymphoblastoid leukaemia), multiple myeloma, squamous cell cancer, testicular cancer, esophageal cancer (such as adenocarcinoma of the gastroesophageal junction), Kaposi's sarcoma, and central nervous system (CNS) lymphoma, hepatocellular carcinoma, nasopharyngeal cancer, Merkel cell carcinoma, and mesothelioma. Tumours of these cancers are known, or expected, to express PD-L1 on their cell surface and/or contain immune cells, such as TILs, expressing PD-L1 and/or LAG-3.

Treatment of renal cell carcinoma, lung cancer (such as non-small cell lung cancer), nasopharyngeal cancer, colorectal cancer, melanoma, stomach cancer (gastric cancer), esophageal cancer (such as adenocarcinoma of the gastroesophageal junction), ovarian cancer, cervical cancer, bladder cancer, head and neck cancer (such as head and neck squamous cell carcinoma), leukemia (such as chronic lymphocytic leukemia, Hodgkin's lymphoma, non-Hodgkin's lymphoma (such as diffuse large B-cell lymphoma, indolent non-Hodgkin's lymphoma, mantle cell lymphoma), and multiple myeloma using anti-LAG-3 antibodies has been investigated in clinical trials and shown promising results. Thus, the cancer to be treated using the antibody molecules of the present invention may be a renal cell carcinoma, lung cancer (such as non-small cell lung cancer), nasopharyngeal cancer, colorectal cancer, melanoma, stomach cancer (gastric cancer), esophageal cancer (such as adenocarcinoma of the gastroesophageal junction), ovarian cancer, cervical cancer, bladder cancer, head and neck cancer (such as head and neck squamous cell carcinoma), leukemia (such as chronic lymphocytic leukemia, Hodgkin's lymphoma, non-Hodgkin's lymphoma (such as diffuse large B-cell lymphoma, indolent non-Hodgkin's lymphoma, mantle cell lymphoma), or multiple myeloma.

Treatment of melanoma, colorectal cancer, breast cancer, bladder cancer, renal cell carcinoma, bladder cancer, gastric cancer, head and neck cancer (such as squamous cell carcinoma of the head and neck), mesothelioma, lung cancer (such as non-small-cell lung cancer), ovarian cancer, Merkel-cell carcinoma, pancreatic cancer, melanoma and hepatocellular carcinoma using anti-PD-L1 antibodies has also been investigated in clinical trials and shown promising results. Thus, the cancer to be treated using the antibody molecules of the present invention may be a melanoma, colorectal cancer, breast cancer, bladder cancer, renal cell carcinoma, bladder cancer, gastric cancer, head and neck cancer (such as squamous cell carcinoma of the head and neck), mesothelioma, lung cancer (such as non-small-cell lung cancer), ovarian cancer, Merkel-cell carcinoma, pancreatic cancer, melanoma, or hepatocellular carcinoma.

Preferred cancers for treatment using the antibody molecules of the present invention are lung cancer (such as non-small-cell lung cancer), bladder cancer, head and neck cancer (squamous cell carcinoma of the head and neck), diffuse large B cell lymphoma, gastric cancer, pancreatic cancer and hepatocellular carcinoma. Tumours of these cancers are known to comprise LAG-3 expressing immune cells and to express PD-L1 either on their cell surface or to comprise immune cells expressing PD-L1.

Where the application refers to a particular type of cancer, such as breast cancer, this refers to a malignant transformation of the relevant tissue, in this case a breast tissue. A cancer which originates from malignant transformation of a different tissue, e.g. ovarian tissue, may result in metastatic lesions in another location in the body, such as the breast, but is not thereby a breast cancer as referred to herein but an ovarian cancer.

The cancer may be a primary or secondary cancer. Thus, the antibody molecule of the present invention may be for use in a method of treating cancer in a patient, wherein the cancer is a primary tumour and/or a tumour metastasis.

The antibody molecules of the invention are designed to be used in methods of treatment of patients, preferably human patients. Antibody molecules will usually be administered in the form of a pharmaceutical composition, which may comprise at least one component in addition to the antibody molecule, such as a pharmaceutically acceptable excipient. For example, a pharmaceutical composition of the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be by injection, e.g. intravenous or subcutaneous. The antibody molecule may be administered intravenously, or subcutaneously.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the antibody molecule, or pharmaceutical composition comprising the antibody molecule, is preferably in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition comprising an antibody molecules according to the present invention may be administered alone or in combination with other treatments, concurrently or sequentially or as a combined preparation with another therapeutic agent or agents, dependent upon the condition to be treated. For example, an antibody molecule of the invention may be administered in combination with an existing therapeutic agent for the disease to be treated, e.g. a cancer as mentioned above. For example, an antibody molecule of the present invention may be administered to the patient in combination with a second anti-cancer therapy, such as chemotherapy, anti-tumour vaccination (also referred to as a cancer vaccination), radiotherapy, immunotherapy, an oncolytic virus, chimeric antigen receptor (CAR) T-cell therapy, or hormone therapy.

It is expected that the antibody molecule of the invention may act as an adjuvant in anti-cancer therapy, such as chemotherapy, anti-tumour vaccination, or radiotherapy. Without wishing to be bound by theory, it is thought that administration of the antibody molecule to the patient as part of chemotherapy, anti-tumour vaccination, or radiotherapy will trigger a greater immune response against the cancer associated antigens LAG-3 and PD-L1, than is achieved with chemotherapy, anti-tumour vaccination, or radiotherapy alone. For example, anti-LAG-3 therapies have shown good efficacy in treating viral based pathologies in mice (Blackburn S D, et al., 2009).

A method of treating cancer in a patient may thus comprise administering to the patient a therapeutically effective amount of an antibody molecule according to the present invention in combination with a chemotherapeutic agent, anti-tumour vaccine, radionuclide, immunotherapeutic agent, oncolytic viruses, CAR-T cells, or agent for hormone therapy. The chemotherapeutic agent, anti-tumour vaccine, radionuclide, immunotherapeutic agent, oncolytic viruses, CAR-T cells, or agent for hormone therapy is preferably a chemotherapeutic agent, anti-tumour vaccine, radionuclide, immunotherapeutic agent, oncolytic viruses, CAR-T cells, or agent for hormone therapy for the cancer in question, i.e. a chemotherapeutic agent, anti-tumour vaccine, radionuclide, immunotherapeutic agent, oncolytic viruses, CAR-T cells, or agent for hormone therapy which has been shown to be effective in the treatment of the cancer in question. The selection of a suitable chemotherapeutic agent, anti-tumour vaccine, radionuclide, immunotherapeutic agent, oncolytic viruses, CAR-T cells, or agent for hormone therapy which have been shown to be effective for the cancer in question is well within the capabilities of the skilled practitioner.

For example, where the method comprises administering to the patient a therapeutically effective amount of an antibody molecule according to the present invention in combination with a chemotherapeutic agent, the chemotherapeutic agent from the group consisting of: taxanes, cyctotoxic antibiotics, tyrosine kinase inhibitors, PARP inhibitors, B_RAF enzyme inhibitors, alkylating agents, platinum analogs, nucleoside analogs, thalidomide derivatives, antineoplastic chemotherapeutic agents and others. Taxanes include docetaxel, paclitaxel and nab-paclitaxel; cytotoxic antibiotics include actinomycin, bleomycin, anthracyclines, doxorubicin and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide, temozolomide; platinum analogs include carboplatin, cisplatin and oxaliplatin; nucleoside analogs include gemcitabine and azacitidine; antineoplastics include fludarabine. Other chemotherapeutic agents suitable for use in the present invention include methotrexate, defactinib, entinostat, pemetrexed, capecitabine, eribulin, irinotecan, fluorouracil, and vinblastine.

Vaccination strategies for the treatment of cancers has been both implemented in the clinic and discussed in detail within scientific literature (such as Rosenberg, S. 2000 Development of Cancer Vaccines). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of antibody molecule, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody molecules are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for an antibody molecule being administered, may be used. A therapeutically effective amount or suitable dose of an antibody molecule can be determined by comparing it's in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule. Treatments may be repeated at daily, twice-weekly, weekly or monthly intervals, at the discretion of the physician. Treatment may be given before, and/or after surgery, and may be administered or applied directly at the anatomical site of surgical treatment.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Selection and Characterisation of Fcab Molecules 1.1 Naïve Selection and Affinity Maturation of Anti-Human LAG-3 Fcabs 1.1.1 Naïve Selection Naïve phage libraries displaying the CH3 domain of human IgG1 (IMGT numbering 1.4-130) with randomisation within the AB (residues 14-18) and EF (residues 92-101) loops were used for selection with recombinant Fc-tagged human LAG-3 (LAG-3 Fc) antigen (R&D systems, 2319-L3-050). The libraries were selected in three rounds using antigen captured on Protein A (Life Technologies, 10002D) or Protein G (Life Technologies, 10004D) beads. The outputs were screened by ELISA and positive binders sub-cloned and expressed as soluble Fcabs (containing a truncated hinge) in *Pichia pastoris* using EasySelect *Pichia* Expression Kit (Life Technologies, K1740-01). The Fcabs were then screened for binding to recombinant human LAG-3 Fc on the Biacore 3000 (GE Healthcare). Briefly, LAG-3 Fc (R&D systems, 2319-L3-050) was coupled at a density of 7200 RU to a CM5 chip (GE Healthcare, BR-100012) using amine coupling (GE Healthcare, BR-1000-50). Fcabs were diluted in HBS-P (GE Healthcare, BR100368) buffer and injected at 250 nM, 500 nM and 1000 nM for 3 min and then allowed to dissociate in buffer for 5 min. Reference subtracted data (LAG-3 Fc flow cell 2—blank flow cell) was analyzed using BIAevaluation 3.2 software to identify binding. Fcabs were then tested for binding to HEK cell-expressed human LAG-3 (LAG-3 cloned into pcDNA5FRT vector [Life Technologies, V6010-20] [See section 1.4.5 for methodology]). Briefly, HEK 293 cells overexpressing human LAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates at $2 \times 10^5$ cells/well. Fcabs were incubated with the cells at 5 µM in a 100 µl volume for 1 h at 4° C. The plates were washed the secondary antibody (Anti-human Fc-488, Jackson ImmunoResearch, 109-546-

098) was diluted 1:1000 in PBS and 100 μl was added to the cells and incubated for 30 min at 4° C. The plates were washed and the cells were resuspended in 100 μl PBS containing 1 μg/ml DAPI (Biotium, 40043). The plate was read on a BD FACSCanto II cytometer (BD Biosciences) and the data analysed using FlowJoX. The Fcabs were then expressed in mammalian cells by transformation using lipofectamine (Life Technologies, 11668-019) into Flp-In T-Rex 293 cells (Life Technologies, R780-07). The LAG-3 binding Fcabs were tested for inhibition of binding of human MHC class II on A375 cells (ATCC, CRL-1619) to recombinant LAG-3 Fc (using the methodology in example 1.6). 54 unique Fcab sequences were identified from three rounds of phage selection, and 12 of these Fcabs were determined to bind to LAG-3 Fc by BIAcore analysis and/or bind to LAG-3 expressing HEK cells. Three of the selected Fcabs were also able to inhibit the interaction of LAG-3 with MHC class II and were selected for affinity maturation. The three Fcabs were termed FS18-3, FS18-7 and FS18-21.

1.1.2 Affinity Maturation
First Affinity Maturation

Six phage display affinity maturation libraries were constructed by randomising five residues in the AB loop (residues 14-18) and either five (residues 92-94 and 97-98) or eight (residues 92-94 and 97-101) residues in the EF loop of each of the three Fcabs identified using the naïve selection process described above.

The affinity maturation libraries were selected using recombinant human LAG-3 Fc (R&D systems, 2319-L3-050) and HEK cells expressing human LAG-3 (as described above). The outputs were screened by phage ELISA, the positive binders were subcloned and expressed as soluble Fcabs (containing a truncated hinge) in HEK Expi293 cells (Fcabs cloned into pTT5 vector [National Research Council of Canada] transfected using ExpiFectamine 293 Transfection kit [Life Technologies, A14524] into Expi293F cells [Life technologies, A14527]). The HEK expressed soluble Fcabs were then screened for binding to cell expressed human LAG-3, binding to cell expressed cynomolgus LAG-3 (methodology as example 1.4.3), and the ability to block MHC class II binding to recombinant LAG-3 Fc (methodology as in example 1.6). The blocking Fcabs were further tested to determine whether they were able to reverse LAG-3 induced inhibition of IL-2 secretion in a T cell activation assay (methodology as in example 2.1). 61 unique anti-LAG-3 Fcabs were identified from the six affinity maturation libraries using these screening methods. Affinity matured Fcabs from the FS18-7 lineage were shown to have the highest level of cross-reactivity with cynomolgus monkey LAG-3. The three Fcabs from this lineage with the strongest binding to cynomolgus monkey LAG-3 Fc and the highest activity in the T cell activation assay (termed FS18-7-7, FS18-7-9, and FS18-7-11) were selected for further affinity maturation. These three Fcabs were also shown to block the interaction of LAG-3 Fc with cell expressed MHC class II.

Second Affinity Maturation

A pool of the three Fcabs (FS18-7-7, FS18-7-9, and FS18-7-11) from the first affinity maturation was used to create further affinity maturation libraries. The CD loop was hard randomized using randomized primers from ELLA Biotech. A portion of amino acid positions in the CD loop (residues 45.1-78) was randomized using an equimolar distribution of amino acids excluding cysteine. Error prone PCR was also carried out across the entire CH3 domain sequence to introduce additional mutations that might enhance binding.

The affinity maturation libraries were generated in phage and selections performed against biotinylated recombinant LAG-3 avi-Fc (BPS Bioscience, 71147) and HEK hLAG-3 cells and screened for binding to recombinant LAG-3 Fc (R&D systems, 2319-L3-050) by phage ELISA. 86 unique Fcabs (containing a truncated hinge) were expressed in HEK293F cells. Selected Fcabs were also screened for activity in a T cell activation assay as described above. The nine Fcabs identified during the second affinity maturation with the highest activity in the T cell activation assay (FS18-7-32; FS18-7-33; FS18-7-36; FS18-7-58; FS18-7-62; FS18-7-65; FS18-7-78; FS18-7-88; and FS18-7-95), as well as the parental Fcab clone, FS18-7-9, were then further characterised as described below. A sequence alignment of these nine Fcabs against the parental Fcab clone, FS18-7-9, is shown in FIG. 1A. FIG. 1B details the percentage sequence identity of each of the nine Fcab clones to the parental Fcab clone, FS18-7-9. Fcabs originating from affinity maturation of the two other parental Fcab clones, FS18-7-7 and FS18-7-11, were not as promising candidates as those originating from affinity maturation of FS18-7-9 and were therefore not pursued further.

1.2 Selection of Surrogate Fcab Specific for Mouse LAG-3

Fcab FS18-7, which was selected using the naïve selection protocol described above, was used to generate phage libraries to select against mouse LAG-3. Two rounds of affinity maturation were performed, and Fcab clones FS18-7-108-29 and FS18-7-108-35, which showed high-affinity, specific binding to mouse LAG-3 were selected following affinity maturation. The ability of FS18-7-108-29 and FS18-7-108-35 to inhibit mouse LAG-3 in a T cell activation assay was confirmed. Epitope mapping using the Octet (Forteo Bio) showed that the anti-mouse LAG-3 Fcabs compete with the anti-human LAG-3 Fcabs (selected following the second affinity maturation as described above) for binding to human LAG-3. There are between 4 and 8 residue differences between the anti-human LAG-3 and anti-mouse LAG-3 Fcabs. It is therefore expected that the anti-mouse LAG-3 Fcabs represent suitable surrogates for the binding and function of the anti-human LAG-3 Fcabs in mice.

1.3 Construction and Expression of Mock mAb$^2$

"mock" mAb$^2$ comprising the lead anti-human LAG-3 and anti-mouse LAG-3 Fcabs identified in 1.1 and 1.2 above were prepared in order to allow the characterisation of these Fcabs in mAb$^2$ format. These mock mAb$^2$ were prepared from the anti-LAG-3 Fcabs and the variable regions of anti-FITC antibody 4420 (see SEQ ID NO: 83, SEQ ID NO: 84, and SEQ ID NO: 85 for details) (Bedzyk, W. D., et al. 1989 and Bedzyk, W. D., et al. 1989). The mock mAb$^2$ were prepared both with (SEQ ID NO: 63, 65, 67, 69, 71, 73, 75, 77, 79, and 81) and without (SEQ ID NO: 64, 66, 68, 70, 72, 74, 76, 78, 80, and 82) the LALA mutation in the CH2 domain of the heavy chain (see section 1.5 below for details) and further comprised the light chain of the anti-FITC mAb 4420 (SEQ ID NO: 85). The mock mAb$^2$ were produced by transient expression in HEK293-6E cells and purified using mAb Select SuRe protein A columns.

1.4 Binding Affinity of Fcabs to LAG-3
1.4.1 Binding Affinity of Fcabs to Human LAG-3 as Determined by Surface Plasmon Resonance (SPR)

A BIAcore T200 (GE Healthcare) was used to measure the affinity of the anti-human LAG-3 Fcabs in the mock mAb$^2$ format for human LAG-3. Flow cell 4 of a CM5 sensor chip (GE Healthcare, BR1005-30) was immobilised with human LAG-3-Fc (R&D Systems, 2319-L3-050), and flow cell 3 was immobilised with buffer for reference using the amine coupling kit (GE Healthcare, BR-1000-50). LAG-3-Fc was diluted to 5 µg/ml in sodium acetate pH5 (Forteo-Bio, 18-1069) and injected at a flow rate of 10 µl/min for 12 seconds followed by deactivation of the surface by injection of ethanolamine for 420 sec. The Immobilisation level was 158 RU. The mock mAb$^2$ (or control anti-human LAG-3 mAb, 25F7) were diluted in HBS-P buffer (GE Healthcare, BR-1003-68) in a 2-fold dilution series from 4 µg/ml. The control mAb/mock mAb$^2$ were injected with an association time of 240 seconds at 30 µl/min, and a dissociation time 300 seconds at 30 µl/min. The surface was regenerated using 25 mM NaOH for 30 seconds at 100 µl/min. The data was double reference subtracted and analysed using the BIAevaluation 3.2 software to calculate kinetic constants. The Fcabs in mock mAb$^2$ format had affinities for human LAG-3 in the range of 0.8-1.1 nM (Table 1), which is similar to the affinity of the benchmark anti-human LAG-3 mAb 25F7. This was surprising because Fcabs have a smaller binding interface than monoclonal antibodies as the binding sites of Fcabs form a relatively compact antibody fragment with two binding sites situated in close proximity. In contrast, the Fab arms of a typical mAb are separated by a flexible hinge region. Based on this smaller binding interface and the associated reduced flexibility of the two binding sites in the Fc region, it was unexpected that the anti-LAG-3 Fcabs were able to bind to and inhibit LAG-3 with similar affinity and potency as the benchmark antibody 25F7.

TABLE 1

Binding affinity of LAG-3 specific Fcabs in mock mAb$^2$ format to human LAG-3

| Anti-human LAG-3 Fcab in mock mAb$^2$ format and benchmark anti-human LAG-3 mAb, 25F7 | $K_D$ (M) |
|---|---|
| FS18-7-9 | $8.3 \times 10^{-10}$ |
| FS18-7-62 | $9.5 \times 10^{-10}$ |
| FS18-7-78 | $8.4 \times 10^{-10}$ |
| FS 18-7-32 | $8.6 \times 10^{-10}$ |
| FS 18-7-36 | $8.9 \times 10^{-10}$ |
| FS 18-7-65 | $1.1 \times 10^{-9}$ |
| 25F7 | $3.2 \times 10^{-10}$ |

1.4.2 Binding Affinity of Surrogate Fcab Specific for Mouse LAG-3 to Mouse LAG-3 as Determined by SPR A Biacore 3000 (GE Healthcare) was used to measure the affinity of the surrogate Fcabs specific for mouse LAG-3 to mouse LAG-3. Amine coupling (amine coupling kit, GE Healthcare, BR-1000-50) was used to coat mLAG-3 Fc (R&D Systems, 3328-L3-050) diluted in 10 mM sodium acetate pH 5.0 (ForteBio, 18-1069) directly to a CM5 chip (GE Healthcare, BR-1000-12). Flow cell 1 was coated with Mouse Fc (SinoBiological, 51094-MNAH), and flow cell 2 was coated with mLAG-3 Fc at 950 RU. Fcabs were diluted in HBS-P buffer (GE Healthcare, BR-1003-68) and injected at various concentrations (fourfold dilutions from 100 nM) for 3 min at 20 µl/min and then allowed to dissociate in buffer for 12 min. The chip was regenerated by injection of 10 mM glycine pH 2.5 for 30 s at 30 µl/min. Data was double reference subtracted and analyzed using BIAevaluation 3.2 software to calculate kinetic constants. The tested surrogate Fcabs bound to mouse LAG-3 with single digit nanomolar affinity as set out in Table 2.

TABLE 2

Binding affinity ($K_D$) of surrogate LAG-3 specific Fcabs to mouse LAG-3

| Surrogate Fcabs specific for mouse LAG-3 | Affinity $K_D$ (nM) |
|---|---|
| FS18-7-108-29 | 1.5 |
| FS18-7-108-35 | 2.1 |

1.4.3 Binding Affinity of Fcabs to Human LAG-3 Expressed on Cells as Determined by Flow Cytometry Production of Cell Lines Over-Expressing LAG-3

Lentiviral transduction methodology was used to generate DO11.10 cells (National Jewish Health) over-expressing human, cynomolgus or mouse LAG-3 using the Lenti-X HTX Packaging System (Clontech, Cat. No 631249). Lenti-X expression vector (pLVX) (Clontech, Cat. No 631253), containing the mouse LAG-3 cDNA (SEQ ID NO: 96), human LAG-3 cDNA (SEQ ID NO: 95) or cynomolgus LAG-3 cDNA (SEQ ID NO: 97), was co-transfected with a Lenti-X HTX Packaging Mix into the Lenti-X 293T Cell Line (Clontech, Cat. No 632180) to generate virus. The DO11.10 cell line was transduced using the lentiviral vectors produced with the Lenti-X HTX Packaging System.

The affinity of the anti-human LAG-3 Fcabs in mock mAb$^2$ format to cells expressing human LAG-3 (DO11.10 cell line transfected with human LAG-3) was measured using flow cytometry. mAb$^2$ and control mAb dilutions (2× final concentration) were prepared in triplicate in 1×DPBS (Gibco, 14190-094). DO11.10:LAG-3 cell suspensions were prepared in PBS+2% BSA (Sigma, A7906) and seeded at $4\times10^{-6}$ cell/ml with 50 µl/well in V-bottomed 96-well plates (Costar, 3897). 50 µl of the mAb$^2$ or control mAb (anti human LAG-3 mAb, 25F7) dilutions were added to the wells containing cells (final volume 100 µl) and incubated at 4° C. for 1 hour. The plates were washed and 100 µl/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 µl of PBS containing DAPI (Biotium, 40043) at 1 mg/ml. The plates were read using Canto II flow cytometer (BD Bioscience). Dead cells were excluded and the fluorescence in the FITC channel (488 nm/530/30) was measured. The data was fitted using log (agonist) vs response in GraphPad Prism Software. All tested Fcabs in mock mAb$^2$ format and the benchmark anti-human LAG-3 mAb, 25F7, bound human LAG-3 with similar affinity ($EC_{50}$), in the range of 1.2-2.1 nM as set out in Table 3.

TABLE 3

Binding affinity of anti-human LAG-3 Fcabs in mock mAb$^2$ format to DO11.10 cells expressing human LAG-3 as determined by flow cytometry

| Anti-human LAG-3 Fcab in mock mAb$^2$ format and benchmark anti-human LAG-3 mAb, 25F7 | $EC_{50}$ (nM) |
|---|---|
| FS18-7-9 | 1.2 |
| FS18-7-32 | 1.6 |
| FS18-7-33 | 1.5 |
| FS18-7-36 | 1.5 |
| FS18-7-62 | 2.1 |
| FS18-7-65 | 1.6 |
| FS18-7-78 | 1.7 |
| 25F7 | 2.1 |

1.4.4 Binding Affinity of Fcabs to Cynomolgus LAG-3 Expressed on Cells as Determined by Flow Cytometry The affinity of the anti-human LAG-3 Fcabs in mock mAb$^2$ format to cells expressing cynomolgus LAG-3 (DO11.10 cell line transfected with cynomolgus LAG-3) was measured using flow cytometry. mAb$^2$ and control mAb dilutions (2× final concentration) were prepared in triplicate in 1×DPBS (Gibco, 14190-094). DO11.10:LAG-3 cell suspensions were prepared in PBS+2% BSA (Sigma, A7906) and seeded at 4×10$^{-6}$ cell/ml with 50 µl/well in V-bottomed 96-well plates (Costar, 3897). 50 µl of the mAb$^2$ or control mAb (anti human LAG-3 mAb, 25F7) dilutions were added to the wells containing cells (final volume 100 µl) and incubated at 4° C. for 1 hour. The plates were washed and 100 µl/well of secondary antibody (anti-human Fc-488 antibody, Jackson ImmunoResearch, 109-546-098) diluted 1:1000 in PBS+2% BSA was then added and incubated for 30 mins at 4° C. in the dark. The plates were washed and resuspended in 100 µl of PBS containing DAPI (Biotium, 40043) at 1 mg/ml. The plates were read using Canto II flow cytometer (BD Bioscience). The dead cells were excluded and the fluorescence in the FITC channel (488 nm/530/30) was measured. The data was fit using log (agonist) vs response in GraphPad Prism Software. The tested Fcabs in mock mAb$^2$ format bound to cynomolgus LAG-3 with 0.5-0.6 nM affinity indicating that toxicology studies in cynomolgus monkeys would be expected to be predictive of effects seen in humans (see Table 4). The benchmark anti-human LAG-3 mAb, 25F7, binds cynomolgus LAG-3 with a 15-fold poorer affinity (EC$_{50}$) (Table 4).

TABLE 4

Binding affinity of anti-LAG-3 Fcabs to DO11.10 cells expressing cynomolgus LAG-3 by flow cytometry

| Anti-human LAG-3 Fcab in mock mAb$^2$ format and benchmark anti-human LAG-3 mAb, 25F7 | EC$_{50}$ (nM) |
|---|---|
| FS18-7-9 | 0.6 |
| FS18-7-62 | 0.5 |
| FS18-7-78 | 0.5 |
| 25F7 | 9.0 |

1.4.5 Binding Affinity of Surrogate Anti-Mouse LAG-3 Fcabs and Anti-Human LAG-3 Fcab to Mouse LAG-3 Expressed on Cells as Determined by Flow Cytometry Production of HEK Cells Over-Expressing mLAG-3

The mouse LAG-3 sequence (SEQ ID NO: 96) was subcloned into pcDNA5FRT vector (Life Technologies, V6010-20) using Kpnl (NEB, R0142) and Notl (NEB, R0146) restriction digestion. The vector was then transformed into Flp-In T-REx 293 HEK cell line (Life Technologies, R780-07) using Lipofectamine 2000 (Life Technologies, 11668-019). Transformed Flp-In T-REx 293 cells were grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) for 3-4 weeks until colonies of stably transformed cells were apparent. These colonies were amplified in the presence of 1 µg/ml Doxycyclin (Sigma, D9891) and tested for mouse LAG-3 expression using PE conjugated anti-mouse LAG-3 (clone C9B7W, BD Biosciences, 552380).

The affinity of the surrogate anti-mouse LAG-3 Fcabs (containing the truncated hinge; SEQ ID NO: 58) to cell-expressed mouse LAG-3 was determined using flow cytometry. HEK cells expressing mLAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates (Costar, 3897) at 2×10$^5$ cells/well. The plates were centrifuged at 1500 rpm for 3 min at 4° C. to pellet the cells. A dilution series of the Fcabs (or control mAb) were incubated with the cells in a 100 µl volume for 1 h at 4° C. The plates were washed and secondary antibody (Anti-human Fc-488, Jackson ImmunoResearch, 109-546-098 for Fcabs or Anti-Rat IgG (H+L), Alexa Fluor 488 Conjugate, ThermoFisher, A-11006 for C9B7W) was diluted 1:1000 in PBS and 100 µl was added to the cells for 30 min at 4° C. (plates were kept in the dark). The plates were then washed and the cells resuspended in 100 µl PBS containing 1 µg/ml DAPI (Biotium, 40043). The plates were read using Canto II flow cytometer (BD Bioscience). Dead cells were excluded and the fluorescence in the FITC channel (488 nm/530/30) was measured. The data was fit using log (agonist) vs response in GraphPad Prism Software. The tested Fcabs bound to mouse LAG-3 with similar affinity (see Table 5). The benchmark LAG-3 mAb, C9B7W (2B Scientific, BE0174-50MG), binds mouse LAG-3 with 17-fold poorer affinity (EC$_{50}$) than the Fcabs (Table 5).

TABLE 5

Binding affinity of surrogate anti-mouse LAG-3 Fcabs to HEK cells expressing mouse LAG-3 by flow cytometry

| Anti-mouse LAG-3 Fcabs and benchmark anti-mouse LAG-3 mAb, C9B7W | EC$_{50}$ (nM) |
|---|---|
| FS18-7-108-29 | 4.5 |
| FS18-7-108-35 | 4.5 |
| C9B7W | 79 |

The affinity of the anti-human LAG-3 Fcab FS18-7-9 in mock mAb$^2$ format to cell-expressed mouse LAG-3 was determined using flow cytometry. HEK cells expressing mLAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014). Cells were collected by centrifuged at 1500 rpm for 3 min at 4° C. to pellet the cells and then resuspended in 1×DPBS then seeded in V-bottom 96-well plates (Costar, 3897) at 1.2×10$^5$ cells/well in 30 µl. A 1:1 volume of a dilution series of the mAb$^2$ (or control mAb) was added and incubated with the cells for 1 h at 4° C. The plates were washed and secondary antibody (Anti-human Fc-488, Jackson ImmunoResearch, 109-546-098) was diluted 1:1000 in PBS and 60 µl was added to the cells for 30 min at 4° C. (plates were kept in the dark). The plates were then washed and the cells resuspended in 60 µl PBS containing 1 µg/ml DAPI (Biotium, 40043). The plates were read using Canto II flow cytometer (BD Bioscience). Dead cells were excluded and the fluorescence in the FITC channel (488 nm/530/30) was measured. The data was fitted using log (agonist) vs response in GraphPad Prism Software. The anti-human LAG-3 Fcab FS18-7-9 in mock mAb$^2$ format bound to mouse LAG-3 with an EC$_{50}$ of 19 nM compared to an EC$_{50}$ of 2.6 nM for the surrogate anti-mouse LAG-3 Fcab FS18-7-9-108 (Table 6). The human mAb, 25F7 does not show any detectable binding to mouse LAG-3, indicating that the human LAG-3 Fcab, FS18-7-9, has a different binding epitope on LAG-3 than that of 25F7.

TABLE 6

Binding affinity of human anti-LAG-3 Fcab FS18-7-9 to HEK cells expressing mouse LAG-3 by flow cytometry

| Anti-human LAG-3 Fcab, anti-mouse LAG-3 Fcab and benchmark anti-human LAG-3 mAb, 25F7 | EC$_{50}$ (nM) |
|---|---|
| FS18-7-108-29 | 2.6 |
| FS18-7-9 | 19 |
| 25F7 | No binding |

1.5 Binding Affinity of Fcabs to Fc Receptors

The introduction of the LALA mutation in the CH2 domain of human IgG1 is known to reduce Fc γ receptor binding (Bruhns, P., et al. (2009); and Xu, D. et al. (2000)). BIAcore was used to confirm that the LALA mutation had reduced the binding affinity of the Fcabs (in mock mAb$^2$ format) to Fcγ receptors. The human FcγR binding assay was performed on a Biacore T200 instrument (GE Healthcare) using the Fcabs in the mock mAb$^2$ format. Human FcγRs (R&D Systems, 1257-FC, 1330-CD, 1875-CD, 4325-FC) were immobilized using amine coupling (amine coupling kit, GE Healthcare, BR-1000-50) onto a Series S CM5 chip (GE Healthcare, BR-1005-30) to a surface density of 370 RU for FcγRI, 264 RU for FcγRIII (high affinity human FcγRs) and 500 RU for FcγRIIa and FcγRIIb (low affinity human FcγRs). For each immobilized chip a flow cell was left blank for background subtraction. FcγR were immobilized using a concentration of 5 µg/ml in sodium acetate pH5 (ForteBio, 18-1069) and injected at a flow rate of 10 µl/min in 15 second cycles until the required immobilization level was reached.

For the high affinity FcγRI and FcγRIII, 200 µg/ml of mAbs or mock mAb$^2$ were flowed across the chip for 3 min at a flow rate of 30 µl/min and the dissociation was followed for 5 min. Running buffer was HBS-P (0.01 M HEPES pH 7.4, 0.15 M NaCl, 0.005% v/v Surfactant P20, GE Healthcare, BR-1003-68). For the low affinity FcγRIIa and FcγRIIb the concentration of mock mAb$^2$ was increased to 500 µg/ml.

The positive control was a wild type IgG1 isotype mAb, which was compared to controls LALA IgG1 mAb and monoclonal IgG2 and IgG4 isotype mAbs to irrelevant targets. The flow cells were regenerated by injecting 10 mM sodium hydroxide (VWR, 28244.262) at a flow rate of 100 µl/min for 30 seconds. The data analysis was performed with BiaEvaluation software version 3.2 RC1 by double referencing against the blank flow cell (without immobilized FcγR) and subtracting a buffer cycle from test mAb$^2$. The results are shown in Table 7.

TABLE 7

Binding response of anti-human LAG-3 Fcabs in mock mAb$^2$ format (comprising LALA mutation as detailed above) to human Fcγ receptors by SPR

| | Binding response at end of association (RU) | | | |
|---|---|---|---|---|
| mAb/mock mAb$^2$ | FcγRI | FcγRIII | FcγRIIa | FcγRIIb |
| FS18-7-9 | 1.4 | 6.6 | −9.8 | −8.5 |
| FS18-7-62 | −0.9 | 0.7 | −10 | −8.5 |
| FS18-7-78 | −0.3 | 4.0 | −10.7 | −9.2 |

TABLE 7-continued

Binding response of anti-human LAG-3 Fcabs in mock mAb$^2$ format (comprising LALA mutation as detailed above) to human Fcγ receptors by SPR

| | Binding response at end of association (RU) | | | |
|---|---|---|---|---|
| mAb/mock mAb$^2$ | FcγRI | FcγRIII | FcγRIIa | FcγRIIb |
| mock mAb LALA | 2 | 8.0 | −12.7 | −9.6 |
| IgG2 | 0 | 1.9 | 9.7 | 7.4 |
| IgG4 | 9 | 3.1 | 4.3 | 15.1 |
| mock mAb IgG1 | 26 | 44 | 13 | 17.7 |

All mock mAb$^2$ tested (all comprising the LALA mutation as set out above) showed significantly reduced binding to the tested Fcγ receptors compared to the control antibody (mock mAb IgG1) without the LALA mutation, indicating that the LALA mutation has reduced Fcγ receptor binding by these mock mAb$^2$ and therefore is expected to reduce ADCC activity of the mAb$^2$.

1.6 Blocking of MHC Class II Binding to LAG-3

The ability of the Fcabs (containing the truncated hinge; SEQ ID NO: 58) to block the interaction between recombinant human or mouse LAG-3 Fc and human MHC Class II was studied by measuring binding of LAG-3 Fc to A375 cells, a melanoma cell line that expresses human MHC Class II. A375 (ATCC, CRL-1619) cells grown in DMEM (Life Technologies, 61965-026) containing 10% FBS (Life Technologies, 10270-106) were detached from cell culture flasks using cell dissociation buffer (Life Technologies, 13151-014) and seeded in V-bottom 96-well plates (Costar, 3897) at 2×10$^5$ cells/well. The plates were centrifuged at 1500 rpm for 3 min at 4° C. to pellet the cells. The relevant concentrations of Fcab or control mAb were incubated with 1 µg/ml LAG-3 Fc (human LAG-3-Fc R&D Systems, 2319-L3-050 or mouse LAG-3 Fc R&D Systems, 3328-L3-050) in 100 µl DMEM containing 10% FBS for 1 h at 4° C. LAG-3/Fcab mix was added to the A375 cells and incubated for 1 h at 4° C. Cells were washed. Secondary antibody (Alexa Fluor 488 conjugated goat anti-human Fc F(ab')$_2$, Jackson Immunoresearch, 109-546-098 or Goat anti-mouse IgG (H+L) 488 conjugate, Life Technologies, A-1101) was diluted 1:1000 in PBS and 100 µl was added to the cells for 30 min at 4° C. (plates were kept in the dark). Cells were washed once in PBS and resuspended in 100 µl PBS+1 µg/ml DAPI (Biotium, 40043). The plates were read on a BD FACSCanto II cytometer (BD Biosciences) and the data analysed using FlowJo software.

Both anti-mouse LAG-3 Fcabs were able to inhibit the interaction of human MHC class II with mouse LAG-3, whereas the control anti-mouse LAG-3 mAb (C9B7W, 2B Scientific, BE0174-50MG) was not (see Table 8).

TABLE 8

Surrogate anti-mouse LAG-3 Fcabs inhibit binding of mouse LAG-3 to MHC class II

| Surrogate anti-mouse LAG-3 Fcabs and control anti-mouse LAG-3 mAb C9B7W | IC$_{50}$ (nM) |
|---|---|
| FS18-7-108-29 | 0.6 |
| FS18-7-108-35 | 0.7 |
| C9B7W | No blocking |

The anti-human LAG-3 Fcabs tested were also able to inhibit the interaction of human MHC class II with human LAG-3 with a similar potency as the control anti-human LAG-3 mAb (25F7).

TABLE 9

Anti-human LAG-3 Fcabs inhibit binding
of human LAG-3 to MHC class II

| Anti-human LAG-3 Fcabs and control anti-human LAG-3 mAb 25F7 | IC$_{50}$ (nM) |
|---|---|
| FS18-7-108-33 | 2.6 |
| FS18-7-108-78 | 2.4 |
| 25F7 | 3.6 |

Example 2: Preparation and Characterisation of mAb and mAb$^2$ Molecules 2.1 Preparation of mAb 84G09

2.1.1 DNA Construct Generation

DNA inserts encoding variable heavy and light chain regions of 84G09 were codon optimised for mammalian expression and synthesised by DNA2.0 (Menlo Park, Calif., USA). The inserts supplied in pJ-Amp-high host vector were sub-cloned into expression vectors pFS-hHC2.1-G1m17(z) LALA (IgG heavy chain containing LALA mutation) or pFS-hHC2.1-G1m17(z) (IgG heavy chain without LALA mutation) and pFShK1.0 (IgG kappa light chain) via EcoRI and NheI restriction digest.

Fidelity of cloning was verified by colony PCR and subsequent nucleotide sequencing analysis by a third party (GATC Biotech).

2.1.2 Cell Maintenance

HEK293-6E cells (NRCC), were sub-cultured in pre-warmed F17 medium (Invitrogen, A13835-01) supplemented with 4 mM of GlutaMAX-1 (Invitrogen, 35050-038), 0.1% of Pluronic F-68 (Invitrogen A13835-01) and 25 μg/ml of geneticin (Invitrogen, 10131-027). Cells were incubated at 37° C., 140 rpm, 5% $CO_2$ and subcultured at $0.3 \times 10^6$ cells/ml on a three then four day regime.

2.1.3 Transient Transfection

HEK293-6E cells were transfected transiently using PEIpro at 1 mg/ml (Polyplus, PPLU115). 24 hours prior transfection cells were seeded at $0.8 \times 10^6$ cells/ml in culture medium. For each 200 ml of cell culture, a DNA mixture was prepared by mixing 10 ml of warmed Opti-MEMI (Invitrogen, 11058-021), 100 μg endotoxin-free DNA encoding the heavy chain and 100 μg endotoxin-free DNA encoding the light chain. PEI mixture was prepared by mixing 10 ml of warmed Opti-MEMI and 200 μl of PEIpro and vortexing. The DNA mixture was quickly added to the vortexed PEI mixture, mixed by vortex pulsing 3 times for 1 s, incubated 3 min at room temperature and added drop by drop to the cells. 48 hours after transfection 20 ml of F17 plus supplements with 0.5% Tryptone N1 (TekniScience Inc., 19553) was added to each flask.

6 days after transfection cells were harvested by centrifugation at 4500 rpm for 40 min. Supernatant was then filtered with 0.22 μm polyethersulfone filter unit (Millipore, SCGPU01RE, SCGPU02RE, SCGPU05RE, SCGPU11 RE) and stored at +4° C. until purification.

2.1.4 Protein a Chromatography

Clarified supernatants were purified using pre-packed 5 ml HiTrap MabSelect SuRe columns (GE Healthcare, 11-0034-95) on an ÅKTAexplorer or ÅKTAxpress. Briefly, the columns were equilibrated with 50 mM Tris-HCl, 250 mM NaCl at pH 7.0, unbound material washed with the same buffer at 5 ml/min. The products were eluted with 10 mM sodium formate pH 3.0 at 5 ml/min. Eluted samples were immediately buffer exchange into PBS pH 7.4 using PD-10 columns (GE Healthcare, 17-0851-01) pre-equilibrated with PBS pH 7.4 according to the manufacturer recommendations.

2.1.5 Product Concentration Measurement by Spectrometry

Absorbance at 280 nm of each purified product was measured using LabChip DS (PerkinElmer, 133089) with DropPlate 96 D+ (PerkinElmer, CLS135136). The product concentration was calculated using extinction coefficient (A280 of 1 mg/ml) calculated using VectorNTI Advance v11.5.4 software (Thermofisher Scientific, A13784)

2.1.6 Product Concentration

When necessary, purified fractions were concentrated using Amicon Ultra-4 Centrifugal Filter Unit 30K (Millipore, UFC803024). After equilibration of the Ultracel regenerated cellulose membrane with PBS pH 7.4 by centrifugation 10 min at 3000 rpm, samples were loaded to the 4 ml unit and centrifuged at 3000 rpm until desired protein concentration was reached.

2.1.6 Filter Sterilisation

Final samples were filtered using pre-wet Millex-GV PVDF syringe filters (Millipore, SLGV013SL).

2.2 Preparation of Human LAG-3/PD-L1 mAb$^2$

The heavy chains of the mAb$^2$ molecules FS18-7-9/84G09 (SEQ ID NOs 94 and 95), FS18-7-32/84G09 (SEQ ID NOs 96 and 97), FS18-7-33/84G09 (SEQ ID NOs 98 and 99), FS18-7-36/84G09 (SEQ ID NOs 100 and 101), FS18-7-58/84G09 (SEQ ID NOs 102 and 103), FS18-7-62/84G09 (SEQ ID NOs 104 and 105), FS18-7-65/84G09 (SEQ ID NOs 106 and 107), FS18-7-78/84G09 (SEQ ID NOs 108 and 109), FS18-7-88/84G09 (SEQ ID NOs 110 and 111) and FS18-7-95/84G09 (SEQ ID NOs 112 and 113) were prepared by replacing the CH3 domains of the monoclonal antibodies 84G09 (with and without the LALA mutation) with the CH3 domains of the human LAG-3 specific Fcabs FS18-7-9, FS18-7-32, FS18-7-33, FS18-7-36, FS18-7-58, FS18-7-62, FS18-7-65, FS18-7-78, FS18-7-88 and FS18-7-95 within XhoI and BamHI sites present in the sequence of the unmodified CH3 domain of human IgG1. The heavy chain of the mAb$^2$ were co-transfected with the light chain of 84G09 (SEQ ID NO: 116) as described for mAb 84G09 in section 2.1 above. The mAb$^2$ were then expressed and purified as described for mAb 84G09 in section 2.1 above.

2.3 Preparation of Human LAG-3/Mock mAb$^2$

The anti-FITC mAb (with and without LALA mutation) was prepared as described for mAb 84G09 in section 2.1 above using the heavy chains (SEQ ID NOs 83 and 84; with and without LALA mutation) and light chain (SEQ ID NO: 85) of mAb 4420.

The heavy chains of the mAb$^2$ molecules FS18-7-9/4420 (SEQ ID NOs 63 and 64), FS18-7-32/4420 (SEQ ID NOs 65 and 66), FS18-7-33/4420 (SEQ ID NOs 67 and 68, FS18-7-36/4420 (SEQ ID NOs 69 and 70), FS18-7-58/4420 (SEQ ID NOs 71 and 72), FS18-7-62/4420 (SEQ ID NOs 73 and 74), FS18-7-65/4420 (SEQ ID NOs 75 and 76), FS18-7-78/4420 (SEQ ID NOs 77 and 78), FS18-7-88/4420 (SEQ ID NOs 79 and 80) and FS18-7-95/4420 (SEQ ID NOs 81 and 82) were prepared by replacing the CH3 domains of the monoclonal antibodies 4420 (with and without the LALA mutation) with the CH3 domains of the human LAG-3 specific Fcabs FS18-7-9, FS18-7-32, FS18-7-33, FS18-7-36, FS18-7-58, FS18-7-62, FS18-7-65, FS18-7-78, FS18-7-88 and FS18-7-95 within XhoI and BamHI sites present in the sequence of the unmodified CH3 domain of human IgG1. The heavy chains of the mAb$^2$ were co-transfected with the light chain of mAb 4420 as described for mAb 84G09 in section 2.1 above. The proteins were then expressed and purified as described for mAb 84G09 in section 2.1 above.

2.4 Preparation of Mouse LAG-3/PD-L1 mAb[2]

The mouse anti-PD-L1 mAb (with and without LALA mutation) was prepared as described for mAb 84G09 in section 2.1 above using the heavy chain (SEQ ID NOs 122 and 123) and light chain (SEQ ID NO: 119) of mAb S1.

The heavy chain of the mAb[2] molecules FS18-7-108-29/S1 (SEQ ID NOs 117 and 118) and FS18-7-108-35/S1 (SEQ ID NOs 120 and 121) were prepared by replacing the CH3 domains of the monoclonal antibodies S1 (with and without the LALA mutation) with the CH3 domains of the mouse LAG-3 specific Fcabs FS18-7-108-29 and FS18-7-108-35 within XhoI and BamHI sites present in the sequence of the unmodified CH3 domain of human IgG1. The heavy chain of the mAb[2] were co-transfected with the light chain of S1 as described for mAb 84G09 in section 2.1 above. The proteins were then expressed and purified as described for mAb 84G09 in section 2.1 above.

2.5 Binding Affinity and Kinetics of mAb[2] for Human LAG-3 and Human PD-L1

Protein L (Thermo, 21189) was immobilized on flow cells 1 and 2 of a Series S CM5 chip (GE Healthcare, BR-1005-30) by amine coupling (GE Healthcare, BR-1000-50) to a surface density of 2000 RU by following the manufacturer's instructions for the BIAcore T200 instrument. For LAG-3 binding, the mAb[2] samples (all containing the LALA mutation) were captured on flow cell 2 only and human LAG-3Fc (R&D Systems, 2319-L3) at 4 concentrations in a two-fold dilution series starting at 0.5 nM were flowed across both flow cell 1 and 2 at a flow rate of 30 μl/min. The association time was 3 min and the dissociation time was 6 min. Running buffer was HBS-P (GE Healthcare, BR-1003-68). Both flow cells were regenerated by injecting 10 mM sodium hydroxide (NaOH) at a flow rate of 100 μl/min for 20 seconds. The data were analysed by double referencing against the blank flow cell.

For PD-L1 binding, four concentrations in a two-fold dilution series of PD-L1 Fc (R&D Systems, 156-B7), starting at 40 nM, were flowed across mAb[2] captured on the same Protein L chip. All others conditions were the same as for LAG-3 binding (see above).

The binding kinetics were fit with a 1:1 Langmuir model to generate binding association ($k_a$) and dissociation ($k_d$) rates. Equilibrium binding constants ($K_D$) were calculated by dividing the dissociation rate by the association rate for each sample. Data analysis was performed with BiaEvaluation software version 3.2. The results are shown in Tables 10 and 11.

TABLE 10

Binding affinity and kinetics of mAb[2] to human LAG-3 as determined by SPR

| mAb[2] | $K_D$ (pM) | $k_a$ (1/Ms) × 10$^6$ | $k_d$ (1/s) × 10$^{-4}$ |
|---|---|---|---|
| 84G09LALA | No binding | — | — |
| FS18-7-09/84G09LALA | 56 | 6.3 | 3.5 |
| FS18-7-32/84G09LALA | 49 | 5.6 | 2.8 |
| FS18-7-33/84G09LALA | 43 | 4.2 | 1.8 |
| FS18-7-36/84G09LALA | 38 | 4.4 | 1.7 |
| FS18-7-62/84G09LALA | 36 | 5.4 | 2.0 |
| FS18-7-65/84G09 LALA | 39 | 5.9 | 2.3 |
| FS18-7-78/84G09 LALA | 29 | 4.8 | 1.4 |

TABLE 11

Binding affinity and kinetics of mAb[2] to human PD-L1 as determined by SPR

| mAb[2] | $K_D$ (nM) | $k_a$ (1/Ms) × 10$^5$ | $k_d$ (1/s) × 10$^{-4}$ |
|---|---|---|---|
| 84G09LALA | 1.2 | 3.8 | 4.6 |
| FS18-7-09/84G09LALA | 1.0 | 3.8 | 3.9 |
| FS18-7-32/84G09LALA | 1.0 | 3.4 | 3.2 |
| FS18-7-33/84G09LALA | 1.1 | 3.7 | 4.2 |
| FS18-7-36/84G09LALA | 3.5 | 1.6 | 5.6 |
| FS18-7-62/84G09LALA | 1.3 | 1.7 | 2.2 |
| FS18-7-65/84G09 LALA | 1.1 | 1.3 | 1.4 |
| FS18-7-78/84G09 LALA | 1.0 | 1.0 | 1.0 |

The binding affinities for human PD-L1 and human LAG-3 were comparable for all the mAb[2] tested. The mAb[2] binding affinities for human PD-L1 were comparable to 84G09, indicating that introduction of the LAG-3 binding site into the CH3 domain did not affect PD-L1 binding.

2.6 Simultaneous Binding of mAb[2] to Human LAG-3 and Human PD-L1

The ability of mAb[2] (FS18-7-09/84G09, FS18-7-32/84G09, FS18-7-33/84G09, FS18-7-36/84G09, FS18-7-62/84G09, FS18-7-65/84G09, and FS18-7-78/84G09 all with the LALA mutation) to bind simultaneously to LAG-3 and PD-L1 was tested by SPR. Human PD-L1Fc (R&D Systems, 156-B7) was immobilized on flow cell 2 of a Series S CM5 chip (GE Healthcare, BR-1005-30) to a surface density of 150 RU by following the manufacturer's instructions. Flow cell 1 was activated and deactivated without any protein immobilised for background subtraction. For each sample, 10 μg/ml of mAb[2] was flowed across flow cells 1 and 2, at a flow rate of 10 μl/min for 3 min. Subsequently, 40 nM of LAG-3Fc (R&D Systems, 2319-L3) was flowed across both flow cell 1 and 2 at a flow rate of 10 μl/min for 3 min. For each binding step dissociation was followed for 3 min. Sensor chip was regenerated after each cycle with a 15 s injection of 25 mM NaOH at a flow rate of 100 μl/min.

All mAb[2] tested were capable of simultaneously binding to LAG-3 and PD-L1. The parental anti-PD-L1 mAb, 84G09, only binds to PD-L1.

2.7. Simultaneous Binding of Surrogate mAb[2] to Murine LAG-3 and Murine PD-L1

The ability of the two surrogate mouse mAb[2] (FS18-7-108-29/S1 and FS18-7-108-35/S1, both containing the LALA mutation) to bind simultaneously to murine LAG-3 and murine PD-L1 was tested by SPR on a BIAcore 3000 (GE Healthcare). Murine PD-L1Fc (R&D Systems, 1019-B7-100) was immobilized on flow cell 4 of a CM5 chip to a surface density of 830 RU according to the manufacturer's instructions. Flow cell 3 was immobilised with 820 RU of human-Fc (R&D system, 110-HG) for background subtraction. For each sample, 50 nM of mAb[2] was flowed across flow cells 1 and 2, at a flow rate of 20 μl/min for 150 sec. Subsequently, 50 nM of murine LAG-3Fc (R&D Systems, 3328-L3-050) was flowed across both flow cell 3 and 4 at a flow rate of 20 μl/min for 150 sec. For each binding step dissociation was followed for 3 min. Sensor chip was regenerated after each cycle with 2×10 μl of 50 mM NaOH. Both mAb[2] tested were capable of simultaneously binding to murine LAG-3 and murine PD-L1 and are therefore suitable surrogates for the human LAG-3/PD-L1 mAb[2].

2.8 Binding to Human Fcγ Receptors by mAb[2] Comprising LALA Mutation

Human Fcγ receptors were immobilized on a CM5 chip to a surface density of approximately 200 RU for Fcγ RI (R&D Systems, 1257-FC) and Fcγ RIIIa (R&D Systems, 4325-FC)

and approximately 500 RU for Fcγ RIIa (R&D Systems, 1330-CD) and Fcγ RIIb/c (R&D Systems, 1875-CD), according to the manufacturer's instruction for the BIAcore3000 instrument. For Fcγ RI and Fcγ RIIIa, 100 µg/ml of mAbs or mAb² were flowed across the chip for 3 min at a flow rate of 10 µl/min and the dissociation was followed for 5 min. Running buffer was PBS (Lonza, BE17-516F)+ 0.05% (v/v) P20 surfactant (GE Healthcare, BR-1000-54). The positive control was wild-type IgG1 4420-mAb. Monoclonal IgG2 and IgG4 mAbs to irrelevant targets (20H4 and MOR7490) and mouse IgG1 (Sigma, P5305) were included as reference points. No regeneration was required due to the fast dissociation rates of the binding complexes. For Fcγ RIIa and Fcγ RIIb/c testing the concentration of mAb² was increased to 500 µg/ml to compensate for the weaker binding to these two receptors. The results are shown in Table 12.

TABLE 12

Binding response of anti-LAG-3/PD-L1 mAb² to human Fcγ receptors as determined by SPR

| mAb/mAb² | Binding response at end of association (RU) | | | |
|---|---|---|---|---|
| | FcγRI | FcγRIII | FcγRIIa | FcγRIIb/c |
| FS18-7-9/84G09 LALA | <1 | <5 | <1 | <2 |
| FS18-7-33/84G09 LALA | <1 | <5 | <1 | <2 |
| FS18-7-62/84G09 LALA | <1 | <5 | <1 | <2 |
| FS18-7-78/84G09 LALA | <1 | <5 | <1 | <2 |
| 84G09 mAb LALA | <1 | <5 | <1 | <2 |
| IgG2 | <1 | <5 | 9 | <2 |
| IgG4 | 8 | <5 | 8 | 9 |
| 4420 mAb IgG1 | 30 | 28 | 29 | 18 |
| Mouse IgG1 | <1 | <5 | 7 | <2 |

As expected, the LALA variant introduced into the mAb or mAb² reduces the ability of these molecules to bind human Fcγ receptors.

2.9 Binding of mAb² to Cells Expressing Human and Cynomolgus LAG-3

The human LAG-3 sequence (SEQ ID NO: 126) or cynomolgus LAG-3 sequence (SEQ ID NO: 128) were subcloned into pcDNA5FRT vector (Life Technologies, V6010-20) using KpnI (NEB, R0142) and NotI (NEB, R0146) restriction digestion. The vector was then transformed into Flp-In T-REx 293 HEK cell line (Life Technologies, R780-07) using Lipofectamine 2000 (Life Technologies, 11668-019). Transformed Flp-In T-REx 293 cells were grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) for 3-4 weeks until colonies of stably transformed cells were apparent. These colonies were amplified in the presence of 1 µg/ml Doxycyclin (Sigma, D9891) and tested for LAG-3 expression was confirmed by flow cytometry.

The affinity of the mAb² (all containing the LALA mutation) for cell expressed human or cynomolgus LAG-3 was determined using flow cytometry. HEK cells expressing human or cynomolgus LAG-3 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates (Costar, 3897) at $2 \times 10^5$ cells/well. The plates were centrifuged at 1500 rpm for 3 min at 4° C. to pellet the cells. A dilution series of the mAb² (or control mAb) were incubated with the cells in a 100 µl volume for 1 h at 4° C. The plates were washed and secondary antibody (Anti-human Fc-488, Jackson ImmunoResearch, 109-546-098) was diluted 1:1000 in PBS and 100 µl was added to the cells for 30 min at 4° C. (plates were kept in the dark). The plates were washed and then cells were resuspended in 100 µl PBS containing 1 µg/ml DAPI (Biotium, 40043). The plates were read using Canto II flow cytometer (BD Bioscience). Dead cells were excluded and the fluorescence in the FITC channel (488 nm/530/30) was measured. The data was fit using log (agonist) vs response in GraphPad Prism Software. The plates were read on a BD FACSCanto II cytometer (BD Biosciences) and the data analysed using FlowJo. The results are shown in Table 13.

TABLE 13

Binding affinity of anti-LAG-3/PD-L1 mAb² to HEK cells expressing human or cynomolgus LAG-3 as determined by flow cytometry

| | human LAG-3 | | cyno LAG-3 | |
|---|---|---|---|---|
| | $EC_{50}$ (nM) | 95% Conf. Int. | $EC_{50}$ (nM) | 95% Conf. Int. |
| FS18-7-09/84G09LALA | 3.179 | 2.311 to 4.372 | 29.9 | 22.16 to 40.35 |
| FS18-7-62/84G09LALA | 4.079 | 2.736 to 6.083 | 26.37 | 15.80 to 44.02 |
| FS18-7-78/84G09LALA | 2.526 | 1.474 to 4.329 | 24.75 | 19.31 to 31.73 |
| 25F7 | 4.192 | 2.791 to 6.297 | 156.5 | 107.3 to 228.2 |

The results confirm mAb² binding to human and cynomolgus LAG-3 expressed on HEK cells. Regarding the calculated $EC_{50}$ values, tested mAb² show better or equal binding to the human LAG-3 and at least two times better binding to the cynomologus LAG-3 when compared with control anti-LAG-3 antibody 25F7. No cross-reactivity with other proteins expressed on the surface of the HEK cell line was observed.

2.10 Binding of mAb² to Cells Expressing Human and Cynomolgus PD-L1

The human PD-L1 sequence (SEQ ID NO: 129) or cynomolgus PD-L1 sequence (SEQ ID NO: 131) were subcloned into pcDNA5FRT vector (Life Technologies, V6010-20) using KpnI (NEB, R0142) and NotI (NEB, R0146) restriction digestion. The vector was then transformed into Flp-In T-REx 293 HEK cell line (Life Technologies, R780-07) using Lipofectamine 2000 (Life Technologies, 11668-019). Transformed Flp-In T-REx 293 cells were grown in DMEM (Life Technologies, 61965-026)

containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) for 3-4 weeks until colonies of stably transformed cells were apparent. These colonies were amplified in the presence of 1 µg/ml Doxycyclin (Sigma, D9891) and LAG-3 expression was confirmed by flow cytometry.

The affinity of the $mAb^2$ (all containing the LALA mutation) binding to cell expressed human or cynomolgus PD-L1 or to parental (untransformed cells) was determined using flow cytometry. HEK cells expressing human or cynomolgus PD-L1 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates (Costar, 3897) at $2\times10^5$ cells/well. The plates were centrifuged at 1500 rpm for 3 min at 4° C. to pellet the cells. A dilution series of the $mAb^2$ (or control mAb) was incubated with the cells in a 100 µl volume for 1 h at 4° C. The plates were washed and secondary antibody (Anti-human Fc-488, Jackson ImmunoResearch, 109-546-098) was diluted 1:1000 in PBS and 100 µl was added to the cells for 30 min at 4° C. (plates were kept in the dark). The plates were washed then cells were resuspended in 100 µl PBS containing 1 µg/ml DAPI (Biotium, 40043). The plates were read using Canto II flow cytometer (BD Bioscience). Dead cells were excluded and the fluorescence in the FITC channel (488 nm/530/30) was measured. The data was fit using log (agonist) vs response in GraphPad Prism Software. The plates were read on a BD FACSCanto II cytometer (BD Biosciences) and the data analysed using FlowJo. The results are shown in Table 14.

TABLE 14

Binding affinity of anti-LAG-3/PD-L1 $mAb^2$ to HEK cells expressing human or cynomolgus PD-L1 as measured by flow cytometry

| | human PD-L1 HEK | | cynomolgus PD-L1 | |
| --- | --- | --- | --- | --- |
| | $EC_{50}$ (nM) | 95% Conf. Int. | $EC_{50}$ (nM) | 95% Conf. Int. |
| 84G09 | 3.107 | 2.230 to 4.331 | 1.641 | 1.244 to 2.164 |
| FS18-7-09/84G09 | 3.19 | 2.208 to 4.610 | 1.674 | 1.393 to 2.012 |
| FS18-7-09/84G09 | 3.51 | 2.570 to 4.794 | 1.814 | 1.503 to 2.189 |
| FS18-7-33/84G09 | 3.448 | 2.436 to 4.881 | 1.895 | 1.566 to 2.292 |
| FS18-7-32/84G09 | 3.816 | 2.749 to 5.298 | 1.984 | 1.644 to 2.393 |
| FS18-7-58/84G09 | 3.775 | 2.957 to 4.820 | 1.861 | 1.541 to 2.247 |
| FS18-7-33/84G09 | 3.225 | 2.214 to 4.700 | 1.733 | 1.397 to 2.150 |
| FS18-7-65/84G09 | 3.999 | 2.782 to 5.750 | 1.845 | 1.455 to 2.339 |
| FS18-7-36/84G09 | 3.907 | 2.844 to 5.367 | 1.999 | 1.580 to 2.528 |
| FS18-7-88/84G09 | 3.492 | 2.541 to 4.800 | 1.814 | 1.464 to 2.247 |
| FS18-7-58/84G09 | 3.907 | 2.998 to 5.093 | 2.033 | 1.622 to 2.550 |
| 84G09 (parental) | 3.051 | 2.181 to 4.267 | 1.959 | 1.515 to 2.533 |

All of the tested LAG-3/PD-L1 $mAb^2$ bound to human PD-L1 and cyno PD-L1 with an $EC_{50}$ close to that of the 84G09 mAb, demonstrating that the PD-L1 binding affinity was not affected by the introduction of the LAG-3 binding site into the CH3 domain of the $mAb^2$.

2.11 Binding of Surrogate Mouse $mAb^2$ to Cells Expressing Mouse LAG-3 or Mouse PD-L1

The murine LAG-3 sequence (SEQ ID NO: 127) or murine PD-L1 sequence (SEQ ID NO: 130) were subcloned into pcDNA5FRT vector (Life Technologies, V6010-20) using KpnI (NEB, R0142) and NotI (NEB, R0146) restriction digestion. The vector was then transformed into Flp-In T-REx 293 HEK cell line (Life Technologies, R780-07) using Lipofectamine 2000 (Life Technologies, 11668-019). Transformed Flp-In T-REx 293 cells were grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) for 3-4 weeks until colonies of stably transformed cells were apparent. These colonies were amplified in the presence of 1 µg/ml Doxycyclin (Sigma, D9891) and LAG-3 or PD-L1 expression was confirmed by flow cytometry.

The affinity of the $mAb^2$ (all containing the LALA mutations) binding to cell expressed murine LAG-3 or murine PD-L1 was determined using flow cytometry. HEK cells expressing murine LAG-3 or murine PD-L1 grown in DMEM (Life Technologies, 61965-026) containing 10% FBS (Life Technologies, 10270-1-6), 100 µg/ml Hygromycin B (Melford Laboratories Ltd, Z2475), 15 µg/ml Blasticidin (Melford Laboratories Ltd, B1105) and 1 µg/ml Doxycyclin (Sigma, D9891) were detached from tissue culture flasks using cell dissociation buffer (Life Technologies, 13151-014) and seeded in V-bottom 96-well plates (Costar, 3897) at $2\times10^5$ cells/well. The plates were centrifuged at 1500 rpm for 3 min at 4° C. to pellet the cells. A dilution series of the $mAb^2$ (or control mAb) were incubated with the cells in a 60 µl volume for 1 h at 4° C. The plates were washed and secondary antibody (Anti-human Fc-488, Jackson ImmunoResearch, 109-546-098 for $mAb^2$ or Anti-Rat IgG (H+L), Alexa Fluor 488, ThermoFisher, A-11006 for anti-LAG-3 control, C9B7W) was diluted 1:1000 in PBS and 50 µl was added to the cells for 30 min at 4° C. (plates were kept in the dark). The plates were washed then cells were resuspended in 50 µl FACS Cell Fix (BD Bioscience, 340181) for 15 minutes, then washed and resuspended in 100 µl PBS containing 1 µg/ml DAPI (Biotium, 40043). The plates were read using Canto II flow cytometer (BD Bioscience). Dead cells were excluded and the fluorescence in the FITC channel (488 nm/530/30) was measured. The data was fit using log (agonist) vs response in GraphPad Prism Software. The plates were read on a BD FACSCanto II cytometer (BD Biosciences) and the data analysed using FlowJo. The results are shown in Table 15.

TABLE 15

Binding affinity of surrogate anti-mouse LAG-3/PD-L1 $mAb^2$ to HEK cells expressing murine LAG-3 or murine PD-L1 by flow cytometry

| | murine LAG-3 HEK | | murine PD-L1 HEK | |
| --- | --- | --- | --- | --- |
| | $EC_{50}$ (nM) | 95% Conf. Int. | $EC_{50}$ (nM) | 95% Conf. Int. |
| C9B7W | 27 | 12.27 to 58.04 | N/A | — |
| FS18-7-108-29/S1 | 2.27 | 1.064 to 4.857 | 11.9 | 7.627 to 18.68 |
| FS18-7-108-29/4420 | 2.29 | 1.256 to 4.164 | N/A | — |
| FS18-7-108-35/S1 | 3.84 | 2.126 to 6.926 | 12.3 | 8.873 to 17.16 |
| FS18-7-108-35/4420 | 2.38 | 0.7819 to 7.239 | N/A | — |

The surrogate $mAb^2$ were able to bind to cell-expressed murine LAG-3 and to cell expressed murine PD-L1. The binding affinity of the surrogate $mAb^2$ to cell expressed murine LAG-3 is approximately the same as the affinity of the anti-human LAG-3/PD-L1 $mAb^2$ to human LAG-3 (2.3-3.8 nM compared to 2.5-4.2 nM) and the binding affinity of the surrogate $mAb^2$ to cell-expressed murine PD-L1 is within 3-fold the affinity of the anti-human LAG-3/PD-L1 mAb² to human PD-L1 (11.9-12.3 nM compared to 3.1-4.0 nM), demonstrating that these mAb² are suitable surrogates for the anti-human LAG-3/PD-L1 mAb² for use in vivo studies in mice.

Example 3: Activity of mAb² Molecules in T Cell Activation Assays and an SEB Assay 3.1 T Cell Activation Assay An IL-2 release assay based on the DO11.10 OVA T-lymphocyte and LK35.2 B-lymphocyte hybridoma cell lines was used for functional screening of the mAb². IL-2 release is a marker of T cell activation. T cells, expressing endogenous murine PD-1, were transfected with either empty vector (pLVX) or human LAG-3 construct. B-cells were transfected with empty vector (pLVX) or human PD-L1 construct.

Three combinations of these four cell lines were used side by side for testing T cell activation by the mAb²:
DO11.10 pLVX+LK35.2 hPD-L1 for anti-PD-L1 activity;
DO11.10 hLAG-3+LK35.2 pLVX for anti-LAG-3 activity;
DO11.10 hLAG-3+LK35.2 hPD-L1 for simultaneous anti-LAG-3/anti-PD-L1 activity.

All mAb² (all containing the LALA mutation) were tested twice in this T cell activation assay. Cross-reactivity with cynomolgus LAG-3 and PD-L1 was tested in a functional T cell activation assay using cells which overexpress cynomolgus targets (cPD-L1 and cLAG-3).

Production of T Cell Lines Over-Expressing LAG-3

Lentiviral transduction methodology was used to generate DO11.10 cells (National Jewish Health) overexpressing human, cynomolgus or mouse LAG-3 using the Lenti-X HTX Packaging System (Cat. No 631249). Lenti-X expression vector (pLVX) (Cat. No 631253), containing the mouse LAG-3 cDNA (SEQ ID NO: 127), human LAG-3 cDNA (SEQ ID NO: 126) or cynomolgus LAG-3 cDNA (SEQ ID NO: 128), was co-transfected with a Lenti-X HTX Packaging Mix into the Lenti-X 293T Cell Line (Cat. No 632180) to generate virus. The DO11.10 cell line was transduced using the lentiviral vectors produced with the Lenti-X HTX Packaging System.

Production of Antigen Presenting Cells Over-Expressing PD-L1

Lentiviral transduction methodology was used to generate LK35.2 B cell lymphoma (ATCC, HB-98) overexpressing human, cynomolgus or mouse PD-L1 using the Lenti-X HTX Packaging System (Cat. No 631249). Lenti-X expression vector (pLVX) (Cat. No 631253), containing the mouse PD-L1 cDNA (SEQ ID NO: 130), human PD-L1 cDNA (SEQ ID NO: 129 or cynomolgus PD-L1 cDNA (SEQ ID NO: 131), was co-transfected with a Lenti-X HTX Packaging Mix into the Lenti-X 293T Cell Line (Cat. No 632180) to generate virus. The LK35.2 cell line was transduced using the lentiviral vectors produced with the Lenti-X HTX Packaging System.

Media and Peptide

Cell culture medium: DMEM (Gibco, 61965-026) 10% FBS (Gibco, 10270-106), 1 mM Sodium Pyruvate (Gibco, 11360-070), 1 µg/ml puromycin (Gibco, A11138-03) Experimental medium: complete DO11.10 culture medium without puromycin. OVA peptide (MW=1773.9 Da): H-ISQAVHAAHAEINEAGR-OH (Pepscan)

Cells:
DO11.10 hLAG-3: DO11.10 T cell hybridoma transduced with a lentiviral vector to overexpress human LAG-3;
DO11.10 pLVX: DO11.10 T cell hybridoma transduced with an empty lentiviral vector;
DO11.10 cLAG-3: DO11.10 T cell hybridoma transduced with a lentiviral vector to overexpress cynomolgus LAG-3.
LK 35.2 hPD-L1: B cell hybridoma transduced with a lentiviral vector containing hPD-L1 to overexpress human PD-L1;
LK 35.2 PLVX: B cell hybridoma transduced with an empty lentiviral (pLVX) vector;
LK 35.2 cPD-L1: B cell hybridoma transduced with a lentiviral vector to overexpress cynomolgus PD-L1.

DO11.10 cells (either DO11.10 pLVX cells or DO11.10 hLAG-3 cells) at $0.3\times10^6$ cells/ml were mixed at a 1:1 ratio with antibodies at 3× final concentration. Antibodies and DO11.10 cells were incubated at 37° C., 5% $CO_2$ for 1 hour. LK 35.2 cells (both pLVX and PD-L1-pLVX) were incubated at $3\times10^6$ cells/ml experimental media with the OVA peptide at 1.5 µM for 30 min. LK 35.2 cells+ OVA were added to DO11.10 cells/treatment mix at a 1:2 ratio in the following combinations:

Human Functional Screen
DO11.10 pLVX+LK35.2 hPD-L1,
DO11.10 hLAG-3+LK35.2 pLVX,
DO11.10 hLAG-3+LK35.2 hPD-L1;
Cynomolgus Cross Reactivity Screen
DO11.10 pLVX+LK35.2 cPD-L1,
DO11.10 cLAG-3+LK35.2 pLVX,
DO11.10 cLAG-3+LK35.2 cPD-L1;

Cells were incubated at 37° C., 5% $CO_2$ for 24 hours. Supernatants were collected and assayed with mouse IL-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on four parameter logistic curve fit (Gen5 Software, BioTek). The concentration of mIL-2 was plotted vs the log concentration of Fcab or mAb and the resulting curves were fitted using the log (agonist) vs response equation in GraphPad Prism. Table 16 shows the $EC_{50}$ values and the maximal IL-2 release of the mAb² and control mAbs, calculated as a percentage of the control (84G09+25F7). FIG. 2A-F show representative plots of IL-2 release by the panel of cell lines treated with FS18-7-9/84G09, FS18-7-62/84G09, or FS18-7-78/84G09, and controls. In the T cell activation assay with both targets present (DO11.10 hLAG-3+LK35.2 hPD-L1), IL-2 release was only induced when both LAG-3 and PD-L1 were inhibited, for example when the mAb² or a combination of LAG-3 and PD-L1 antibodies was used. Therefore the mAb² has benefit over a single agent alone. In the assays with just LAG-3 (DO11.10 hLAG-3+LK35.2 pvlx) or PD-L1 (DO11.10 pvlx+LK35.2 PD-L1) the mAb² showed similar activity as the single agents in inhibiting these targets, demonstrating that the mAb² is the only single molecule which was able to lead to T cell activation in the presence of LAG-3, PD-L1 or LAG-3+PD-L1.

TABLE 16

EC$_{50}$ and maximal IL2 release (as calculated by percentage of IL2 release compared to control - 84G09 + 25F7) for nine mAb$^2$

| mAb$^2$/control mAbs | AVERAGE EC$_{50}$ | SD | AVERAGE Maximal IL2 release calculated as % ctrl (84G09 + 25F7) | SD |
|---|---|---|---|---|
| FS18-7-09/84G09LALA | 0.75 | 0.20 | 65.89 | 24.04 |
| FS18-7-33/84G09LALA | 0.82 | 0.35 | 63.95 | 36.56 |
| FS18-7-78/84G09LALA | 0.82 | 0.38 | 64.39 | 39.28 |
| FS18-7-62/84G09LALA | 0.65 | 0.02 | 58.97 | 18.13 |
| FS18-7-65/84G09LALA | 0.81 | 0.20 | 70.25 | 2.22 |
| FS18-7-95/84G09LALA | 1.10 | — | 79.77 | — |
| FS18-7-32/84G09LALA | 1.19 | 0.00 | 82.94 | 14.67 |
| FS18-7-36/84G09LALA | 1.05 | 0.32 | 71.56 | 8.83 |
| FS18-7-58/84G09LALA | 1.16 | 0.21 | 79.40 | 0.10 |
| 84G09LALA + 25F7 | 1.32 | 0.25 | 100.00 | |

Figure 3:
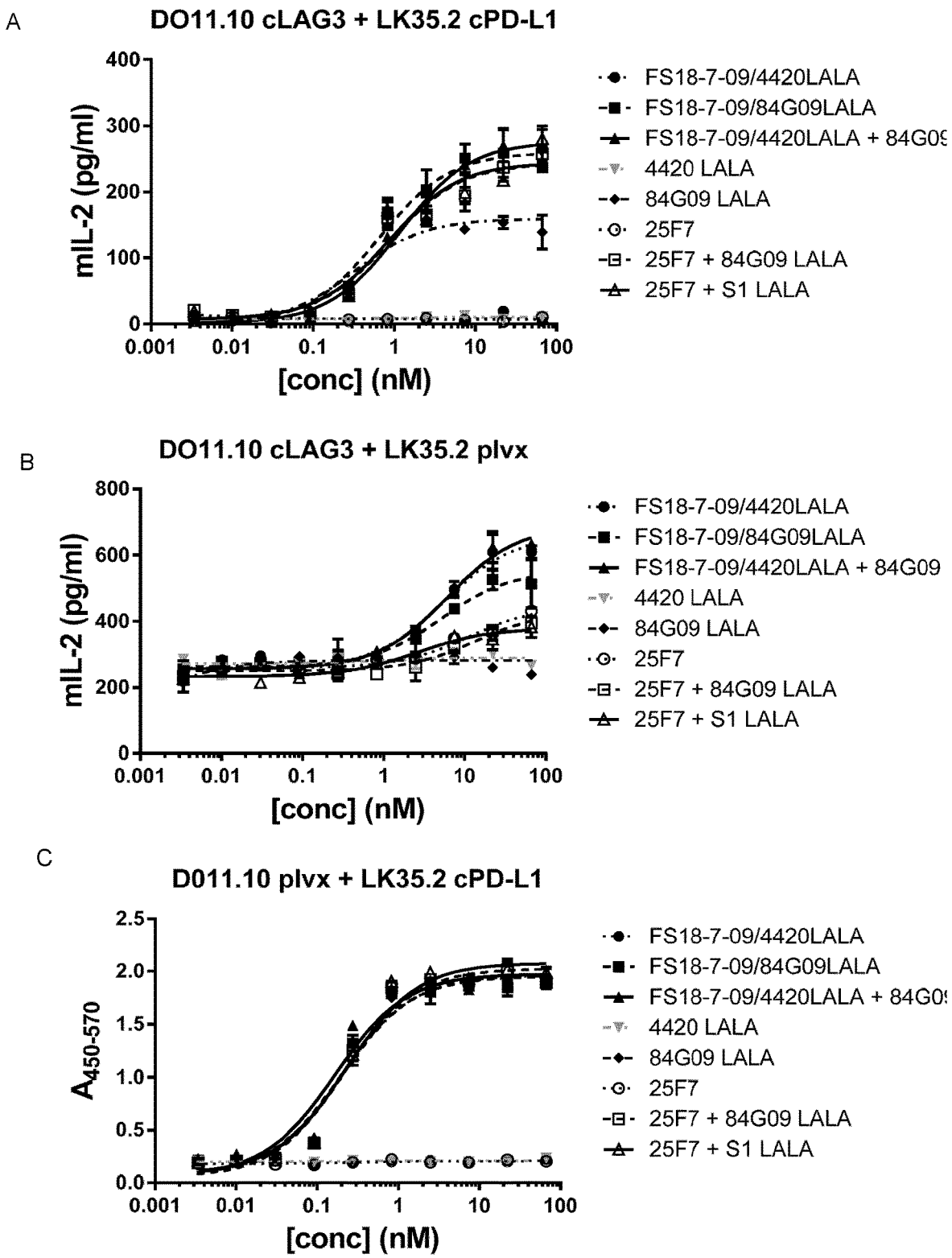
FIG. 3 shows that FS18-7-9/84G09 was able to induce T cell activation, as indicated by IL-2 release, in the presence of both cLAG-3+ cPD-L1 and cLAG-3 or cPD-L1 alone showing functionally cynomolgus cross-reactivity.

One of the mAb$^2$ (FS18-7-9/84G09 containing the LALA mutation) was tested for cynomolgus functional cross reactivity in the DO11.1-/LK35.2 T cell activation assay. FIG. 3 A-C show the results in the panel of three cell based assays. FS18-7-9/84G09 was able to induce T cell activation in the presence of both cLAG-3+ cPD-L1 and cLAG-3 or cPD-L1 alone, indicating that the mAb$^2$ are functionally cynomolgus cross-reactive and therefore suitable for use in primate based safety studies.

3.2 Staphylococcal Enterotoxin B Assay

Three mAb$^2$ (all containing the LALA mutation) were tested in the human-PBMC based Staphylococcal Enterotoxin B assay (SEB assay). Staphylococcal Enterotoxin B is a superantigen, and binds to MHC class II molecules on antigen presenting cells (APCs) and the vβ chain of the T cell receptor (TCR), causing non-specific activation of T cells and cytokine release. There is no requirement for antigen to be present to see T cell activation. The SEB assay uses stimulated human cells (PBMCs) with physiological levels of checkpoint inhibitors, and can be used to confirm that T cell activation is enhanced by the mAb$^2$ in a human system. Three mAb$^2$ were tested in the SEB system with cells coming from four different donors.

Generation of Expanded T Cells

PMBCs were isolated from leukocyte cones by Ficoll gradient separation. CD4+ T cells were isolated using human CD4+ T Cell Isolation Kit (Miltenyi Biotec Ltd, 130-096-533) according to the manufacturer's instruction. Human T-Activator CD3/CD28 Dynabeads (Life technologies, 11131D) were resuspended by vortexing. Beads were transferred to a sterile 15 ml tube and 10 ml RPMI (Life Technologies, 61870044) with 10% FBS (Life Technologies, 10270106) and 1× Penicillin Streptomycin (Life Technologies, 15140122) was added to wash Dynabeads. The supernatant was discarded. The required amount of CD4+ T cells at 1.0×10$^6$ cells/ml in RPMI with 10% FBS and 1× Penicillin Streptomycin Solution and 50 IU/ml recombinant human IL2 (Peprotech, 200-02-50 µg) with 3:1 bead to cell ratio were transferred to T75 flask (Greiner Bio-one, 690195) and incubated at 37° C.+5% CO$_2$. After 3 days the cells were gently resuspended and counted. The cell density was maintained between 0.8-1×10$^6$ cells/ml by adding fresh media (RPMI-10% FBS+Penicillin Streptomycin Solution 1×+50 IU/ml rhuIL2) as needed. On day 7 or 8, the CD3/28 beads were removed and CD4+ T cells were rested overnight at 1×10$^6$ cells/ml fresh media RPMI-10% FBS+ Penicillin Streptomycin Solution 1× with reduced 10 IU/ml rhuIL2. The cells were stored frozen until required.

Generation of MoiDCs

Untouched monocytes were isolated from human PBMCs using human Pan Monocyte Isolation Kit, (Miltenyi Biotec Ltd, 130-096-537) following the manufacturer's instructions. Monocytes were differentiated to iDCs using human Mo-DC Differentiation Medium (Miltenyi Biotec Ltd, 130-094-812) following the manufacturer's instructions.

SEB Assay

Figure 4:
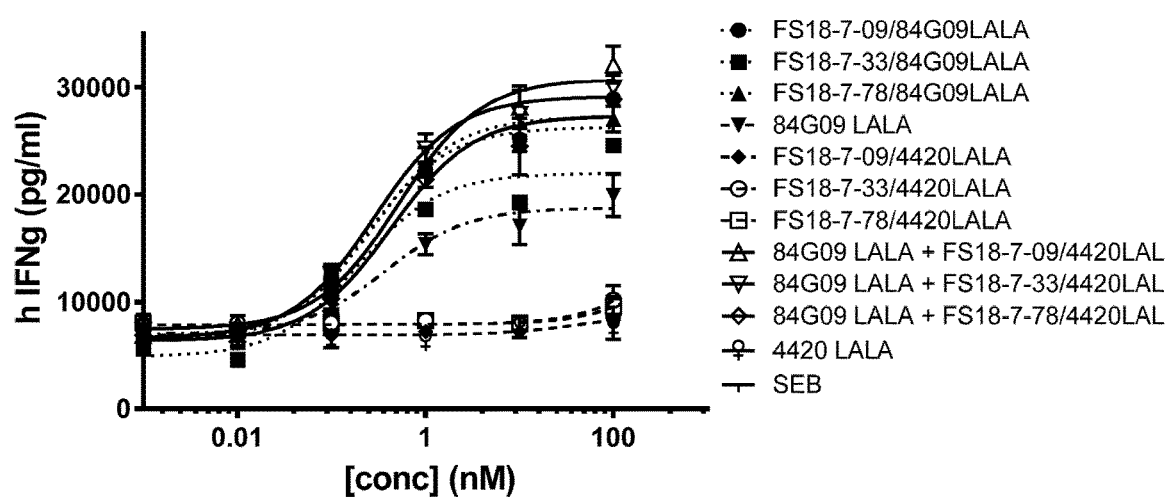
FIG. 4 shows a representative plot from the SEB assay. LAG-3/PD-L1 mAb$^2$ and the combination of the LAG-3/4420 mAb$^2$+84G09LALA showed greater activation that the 84G09LALA mAb alone, whereas the LAG-3/4420 mAb$^2$ or 4420 mAb did not show significant activation.

Expanded T cells were thawed one day before the experiment, washed with AIM medium (Gibco, 12055-091) and incubated at 37° C., 5% CO$_2$ overnight at 1×10$^6$ cells/ml in AIM medium. 2 µM concentration of each antibody/mixture was prepared in DPBS (Gibco, 14190-169) and diluted 1:10 in medium (30 µl+270 µl) to obtain 200 nM. In a 96 well plate, serial dilutions were carried out at 1:10 (30 µl+270 µl experimental medium; 2× final conc.). MoiDCs were thawed, washed with AIM medium and mixed with T cells from the same donor at a 1:10 ratio (5 ml of iDCs at 2×10$^5$ cells/ml were combined with 5 ml of T cells at 2×10$^6$ cells/ml). 20 µl of SEB (Sigma, S4881) at 0.1 µg/ml was added to 10 ml of the cells. In a round bottom 96 well plate, 100 µl of the cell/SEB mixture was added to 100 µl of the antibody dilution, giving a ratio of 10$^4$ iDC cells to 10$^5$ T cells with 0.1 ng/ml SEB in 200 µl of AIM media per well with final antibody concentrations of 100, 10, 1, 0.1, 0.01, 0.001 nM. Cells were incubated at 37° C., 5% CO2 for 3 days. Supernatants were collected and assayed immediately with human IFN$_γ$ ELISA kit (R&D Systems, PDIF50) or frozen down at −20° C. for further analysis. The assay was performed according to the kit manufacturer's instructions using supernatants diluted 1:30 with PBA (DPBS, 2% BSA (Sigma, A7906-100G)). The concentration of human IFN$_γ$ was plotted vs the log concentration of mAb$^2$ or mAb and the resulting curves were fitted using the log (agonist) vs response equation in GraphPad Prism software. Table 17 shows the EC$_{50}$ values and the span of the IFN$_γ$ release in the SEB assay with cells from four different cell donors (Donors A to D). FIG. 4 shows a representative plot of the SEB assay with a single donor. In all six assays the LAG-3/PD-L1 mAb$^2$ and the combination of the LAG-3/FITC mAb$^2$+ 84G09LALA showed greater activation than the 84G09LALA mAb alone, whereas when the LAG-3/FITC mAb$^2$ or 4420 mAb were assayed they did not show significant activation. The results of the SEB assay therefore confirm the results of the DO11.10/LK35.2 assay in a more physiological system.

TABLE 17

EC$_{50}$ values calculated for six mAb$^2$ based on six SEB assays with 4 different cell donors.

| | EC$_{50}$ (nM) | 95% Conf. Int. | SPAN | 95% Conf. Int. |
|---|---|---|---|---|
| Assay 1 Donor A | | | | |
| FS18-7-09/84G09LALA | 0.1551 | 0.08521 to 0.2824 | 12280 | 10802 to 13758 |
| FS18-7-62/84G09LALA | 0.1424 | 0.08665 to 0.2340 | 12120 | 10897 to 13342 |

TABLE 17-continued

EC$_{50}$ values calculated for six mAb$^2$ based on
six SEB assays with 4 different cell donors.

| | EC$_{50}$ (nM) | 95% Conf. Int. | SPAN | 95% Conf. Int. |
|---|---|---|---|---|
| FS18-7-78/84G09LALA | 0.2774 | 0.1220 to 0.6310 | 14156 | 11970 to 16341 |
| 84G09 LALA | 0.1884 | 0.08960 to 0.3962 | 10077 | 8612 to 11542 |
| FS18-7-09/4420LALA | — | — | 1010 | 384.8 to 1635 |
| FS18-7-62/4420LALA | — | — | 416.1 | −443.1 to 1275 |
| FS 18-7-78/4420LALA | — | — | 411 | −1103 to 1925 |
| 84G09 LALA + FS18-7-09/4420LAL | 0.2455 | 0.1030 to 0.5850 | 11836 | 9888 to 13785 |
| 84G09 LALA + FS18-7-62/4420LAL | 0.1601 | 0.05399 to 0.4750 | 11448 | 8958 to 13937 |
| 84G09 LALA + FS18-7-78/4420LAL | 0.1774 | 0.06863 to 0.4587 | 12250 | 9955 to 14544 |
| 4420 LALA | — | — | 218.6 | −35.91 to 473.1 |
| | | Assay 1 Donor B | | |
| FS18-7-09/84G09LALA | 0.07316 | 0.02255 to 0.2374 | 11825 | 8919 to 14730 |
| FS18-7-62/84G09LALA | 0.03236 | 0.007146 to 0.1465 | 12170 | 8419 to 15921 |
| FS18-7-78/84G09LALA | 0.09718 | 0.03128 to 0.3019 | 15198 | 11594 to 18802 |
| 84G09 LALA | 0.08562 | 0.03403 to 0.2154 | 12343 | 9957 to 14730 |
| FS18-7-09/4420LALA | — | — | 1337 | −195.8 to 2870 |
| FS18-7-62/4420LALA | — | — | 2508 | −2118 to 7133 |
| FS 18-7-78/4420LALA | — | — | 1425 | −58.52 to 2908 |
| 84G09 LALA + FS18-7-09/4420LAL | 0.2861 | 0.1005 to 0.8143 | 16037 | 12890 to 19184 |
| 84G09 LALA + FS18-7-62/4420LAL | 0.1431 | 0.02857 to 0.7172 | 13907 | 9358 to 18455 |
| 84G09 LALA + FS18-7-78/4420LAL | 0.3775 | 0.08929 to 1.596 | 14418 | 10502 to 18334 |
| 4420 LALA | — | — | 2293 | 1028 to 3558 |
| | | Assay 2 Donor A | | |
| FS18-7-09/84G09LALA | 0.2761 | 0.1654 to 0.4611 | 20727 | 18729 to 22724 |
| FS18-7-33/84G09LALA | 0.1934 | 0.07990 to 0.4681 | 171 03 | 14156 to 20049 |
| FS18-7-78/84G09LALA | 0.2384 | 0.1596 to 0.3560 | 19822 | 18311 to 21333 |
| 84G09 LALA | 0.3788 | 0.1166 to 1.230 | 11745 | 9138 to 14352 |
| FS 18-7-09/4420LALA | — | — | 1991 | −1927 to 5909 |
| FS 18-7-33/4420LALA | — | — | ~1.053e+006 | (Very wide) |
| FS 18-7-78/4420LALA | — | — | ~72657 | (Very wide) |
| 84G09 LALA + FS18-7-09/4420LALA | 0.5202 | 0.2624 to 1.031 | 23346 | 20230 to 26462 |
| 84G09 LALA + FS18-7-33/4420LALA | 0.2881 | 0.1529 to 0.5428 | 22529 | 19853 to 25205 |
| 84G09 LALA + FS18-7-78/4420LALA | 0.4335 | 0.2089 to 0.8996 | 20955 | 18038 to 23873 |
| | | Assay 2 Donor B | | |
| FS18-7-09/84G09LALA | 0.139 | 0.04157 to 0.4646 | 21572 | 16269 to 26874 |
| FS18-7-33/84G09LALA | 0.07278 | 0.01615 to 0.3280 | 19554 | 13408 to 25699 |
| FS18-7-78/84G09LALA | 0.1356 | 0.03552 to 0.5178 | 22319 | 16212 to 28426 |
| 84G09 LALA | 0.1959 | 0.03365 to 1.140 | 12077 | 7938 to 16216 |
| FS18-7-09/4420LALA | — | — | 1272 | −963.4 to 3507 |
| FS18-7-33/4420LALA | — | — | 2272 | −190.8 to 4735 |
| FS18-7-78/4420LALA | — | — | 1960 | −1287 to 5207 |
| 84G09 LALA + FS18-7-09/4420LALA | 0.2889 | 0.07772 to 1.074 | 23661 | 17835 to 29488 |
| 84G09 LALA + FS18-7-33/4420LALA | 0.3 | 0.06936 to 1.298 | 26145 | 18971 to 33320 |
| 84G09 LALA + FS18-7-78/4420LALA | 0.271 | 0.03980 to 1.845 | 25489 | 16292 to 34686 |
| | | Assay 1 Donor C | | |
| FS18-7-09/84G09LALA | 0.06739 | 0.01933 to 0.2349 | 2987 | 15107 to 27710 |
| 84G09 LALA | 0.08347 | 0.0331 to 0.2105 | 1509 | 11046 to 17414 |
| 84G09 LALA + FS18-7-09/4420LALA | 0.1618 | 0.06635 to 0.3944 | 1744 | 13346 to 20704 |
| Assay 1 Donor D | | | | |
| FS18-7-09/84G09LALA | 0.04373 | 0.01797 to 0.1064 | 1850 | 15995 to 23799 |
| 84G09 LALA | 0.07043 | 0.03483 to 0.1424 | 1045 | 10996 to 15405 |
| 84G09 LALA + FS18-7-09/4420LALA | 0.1351 | 0.08359 to 0.2182 | 968 | 15318 to 19403 |

Example 4: In Vivo Activity of mAb² Molecules in Murine Tumour Models

4.1 Activity of mAb² Molecules in a MC38 Non-Established Tumour Model

The MC38 syngeneic tumour model was used in this experiment as MC38 tumours are known to express PD-L1 on their cell surface and to be highly immunogenic resulting in increased LAG-3 expression on immune cells in the tumour and tumour periphery.

The surrogate mouse mAb² FS18-7-108-29/S1 containing the LALA mutation (SEQ ID NO: 117 and 119) referred to as FS18-29/S1 was tested for in vivo activity using a MC38 syngeneic mouse tumour growth model. The ability of the mAb² to inhibit tumour growth was compared to that of the LAG-3/mock mAb², FS18-7-108-29/4420 containing the LALA mutation (SEQ ID NO: 132 and 85) referred to as FS18-29/4420, the benchmark anti-LAG-3 mAb C9B7W (2B scientific; Catalogue Number BE0174-50MG), the benchmark anti-PD-L1 mAb S1 containing the LALA mutation (SEQ ID NO: 122 and 119) and to a combination of mAbs C9B7W and S1.

C57BL/6 female mice (Charles River) aged 8-10 weeks and weighing 20-25 g each were rested for one week prior to the study start. All animals were micro-chipped and given a unique identifier. Each cohort had 10 mice. The MC38 colon carcinoma cell line (S. Rosenberg, NIH) was initially expanded, stored, and then pre-screened by IDEXX Bioresearch for pathogens using the IMPACT I protocol and shown to be pathogen free. MC38 cells were thawed from $-150°$ C. storage and added to 20 ml DMEM (Gibco, 61965-026) with 10% FCS (Gibco, 10270-106) in a T175 tissue culture flask. Mice were anaesthetised using isoflurane (Abbott Laboratories) and each animal received $2 \times 10^6$ cells injected subcutaneously in the left flank. 7-8 days following tumour cell inoculation, mice which did not have tumours at this point were removed from the study.

All of the mAb² molecules and the control antibodies were analysed within 24 hours prior to injection by SEC-HPLC profiling and checked for impurities. Antibodies were prepared at a final concentration of 10 mg/kg in PBS and combined with a second antibody in the combination studies. The mAb² molecules and the control antibodies were administered to the mice by intraperitoneal (IP) injection on days 8, 11, and 14 following tumour inoculation. Accurate measurements of tumours were taken, any drug dosing due on the day in question was performed, and the mice subjected to close observation for the remainder of the trial. Tumour volume measurements were taken with callipers to determine the longest axis and the shortest axis of the tumour. The following formula was used to calculate the tumour volume:

$$L \times (S^2)/2$$

Where L=longest axis; S=shortest axis

The trial was halted at day 20 when the tumour burden was considered close to restrictions. All mice were humanely sacrificed and the tumours were excised and weighed.

Figure 5:
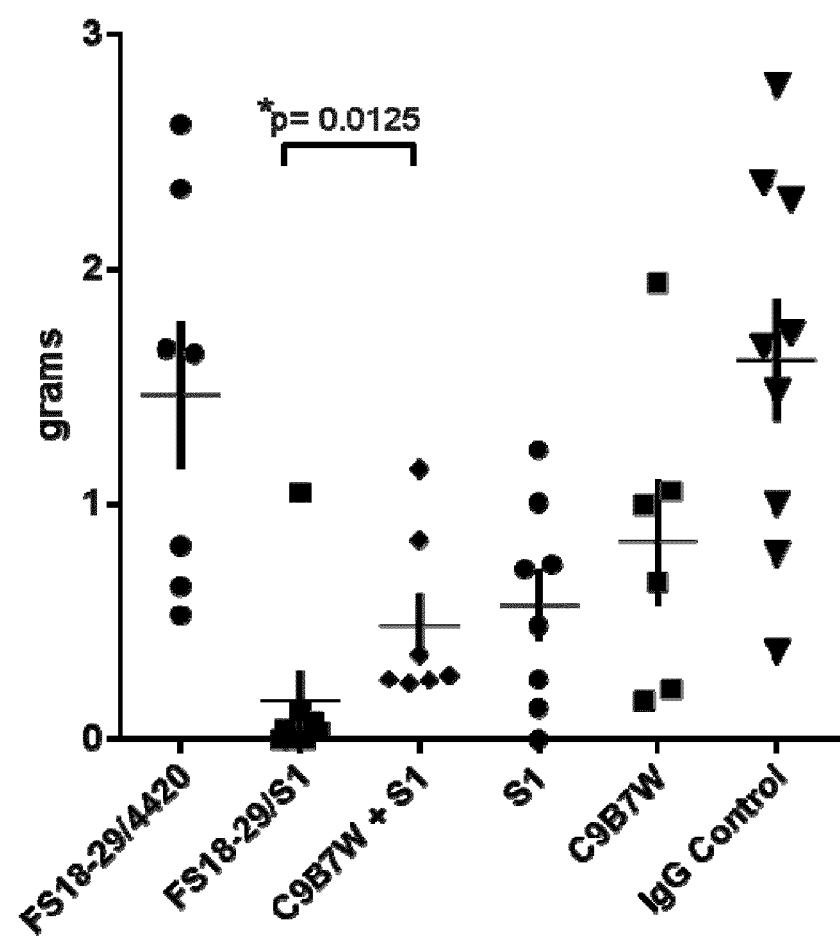
FIG. 5 shows the end tumour weights on day 20 in the non-established MC38 syngeneic tumour model. LAG-3/PD-L1 mAb$^2$ (FS18-29/S1) treated mice had end tumours with significantly smaller weights than those treated with a combination of benchmark mAbs, C9B7W and S1.
Figure 6:
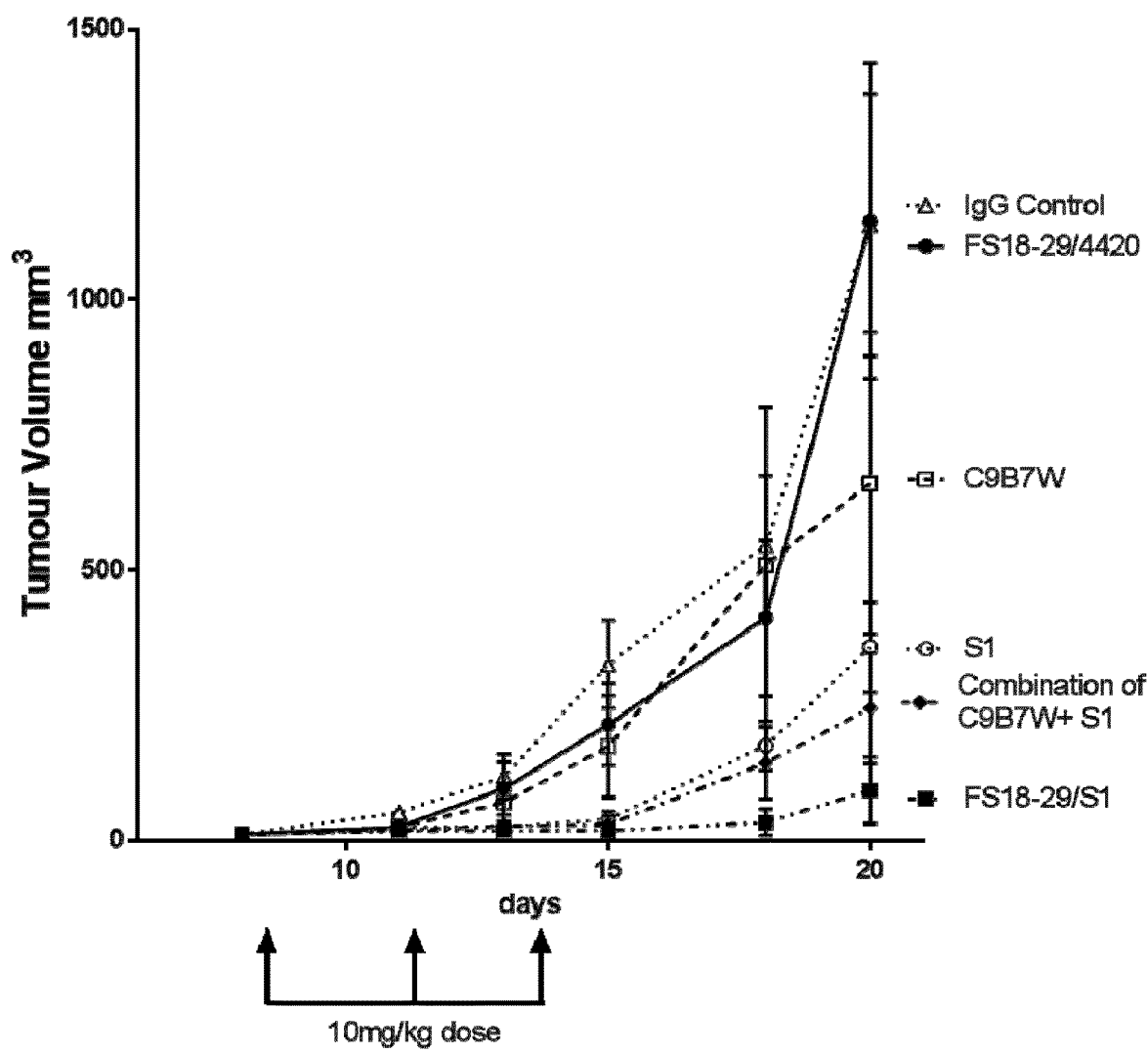
FIG. 6 shows growth curves of the non-established MC38 syngeneic tumour model. LAG-3/PD-L1 mAb$^2$ (FS18-29/S1) treated mice had smaller tumours than those treated with a combination of benchmark mAbs, C9B7W and S1, or those treated with S1 alone. The LAG-3/4420 mAb$^2$ and benchmark anti-LAG-3 mAb had little impact on tumour growth.

The results are shown in FIGS. 5 and 6. LAG-3/PD-L1 mAb² (FS18-29/S1) treated mice had end tumours with significantly smaller weights than those treated with a combination of benchmark mAbs, C9B7W and S1. Specifically, statistical analysis of end tumour weights was performed using a two tailed Student's t-test within the GraphPad Prism software package demonstrating a statistical significant difference between administration of FS18-29/S1 and administration of the combination of benchmark antibodies C9B7W and S1 (p=0.0125), indicating that LAG-3 and PD-L1 inhibition provided by the same molecule resulted in a synergistic effect on end tumour weights compared with LAG-3 and PD-L1 inhibition provided by separate molecules.

The surrogate mAb² FS18-29/S1 also had a marked effect on tumour growth preventing the establishment in 6 of 8 growing MC38 tumours, and slowing the growth of the remaining 2. Administration of the benchmark anti-LAG-3 and PD-L1 antibodies in combination slowed tumour growth in 7 animals with no animals being tumour free.

FS18-29/4420 alone had no marked effect on tumour growth, indicating that for maximal efficacy, the mAb² requires the anti-PD-L1 Fab. The benchmark anti-mouse LAG-3 antibody alone had little or no effect on resulting tumour growth while the benchmark anti-mouse PD-L1 prevented establishment of 1 of 7 tumours in this cohort, and had some overall effect of slowing tumour growth.

Syngeneic mouse models are accepted as appropriate murine systems for testing the anti-tumour effect of inhibiting therapeutic targets and have been used extensively to validate development of human therapeutics.

4.2 Activity of mAb2 Molecules in a MC38 Established Tumour Model

The surrogate mouse mAb² FS18-7-108-29/S1 containing the LALA mutation, (SEQ ID NO: 117 and 119) referred to as FS18-29/S1, was tested for in vivo activity in a MC38 syngeneic mouse tumour growth model. The ability of the mAb² to inhibit tumour growth was compared to that of the LAG-3/mock mAb², FS18-7-108-29/4420 containing the LALA mutation (SEQ ID NO: 132 and 85), referred to as FS18-29/4420, the benchmark LAG-3 mAb C9B7W, the benchmark PD-L1 mAb S1 containing the LALA mutation (SEQ ID NO: 122 and 119) and to a combination of C9B7W and S1.

C57BL/6 female mice (Charles River) aged 8-10 weeks and weighing 20-25 g each were rested for one week prior to the study start. All animals were micro-chipped and given a unique identifier. Each cohort had 10 mice. The MC38 colon carcinoma cell line (S. Rosenberg, NIH) was initially expanded, stored, and then pre-screened by IDEXX Bioresearch for pathogens using the IMPACT I protocol and shown to be pathogen free. MC38 cells (approximately $3-5 \times 10^6$) was thawed from $-150°$ C. storage and added to 20 ml DMEM (Gibco, 61965-026) with 10% FCS (Gibco, 10270-106) in a T175 tissue culture flask. Mice were anaesthetised using isofluorane (Abbot Laboratories) and $2 \times 10^6$ cells in 100 µl were injected subcutaneously into the left flank of each mouse. 7-8 days following tumour cell inoculation, mice were routinely monitored for health and tumour growth appropriate for initiation of the study. When the majority of mice exhibited tumours of 5-10 mm diameter, they were sorted and randomised back into study cohorts. Any mice which did not have appropriately sized tumours at this point were removed from the study.

All of the mAb² molecules and the control antibodies were analysed within 24 hours prior to injection by SEC-HPLC profiling and checked for impurities. Antibodies were prepared at a final concentration of 10 mg/kg in PBS and combined with the second antibody for the combination studies. The mAb² molecules and the control antibodies were administered to the mice on days 15, 18, and 21 following tumour inoculation by IP injection. Animals were health screened under anaesthesia three times a week in a blinded fashion, during which time accurate measurements of tumours were taken. Tumour volume measurements were taken with callipers to determine the longest axis and the shortest axis of the tumour. The formula used to calculate the tumour volume was as set out in section 4.1 above.

Figure 7:
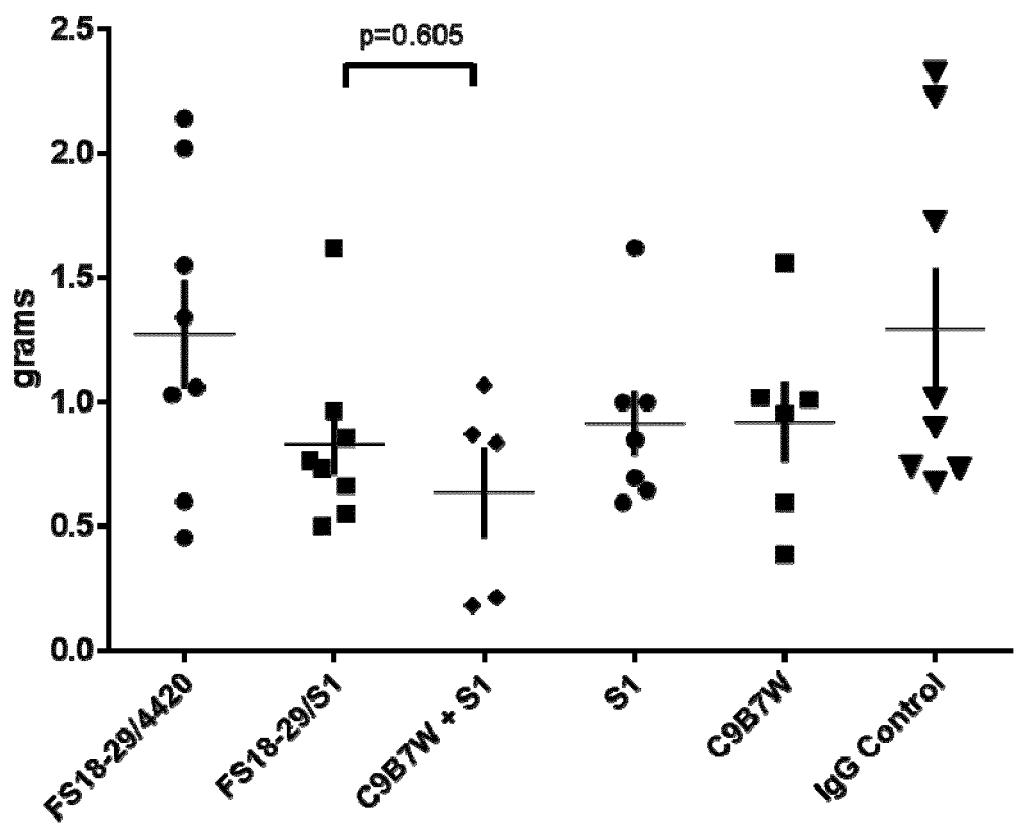
FIG. 7 shows the end tumour weights on day 24 in the established MC38 syngeneic tumour model. LAG-3/PD-L1 mAb$^2$ (FS18-29/S1) was just as effective in suppressing tumour growth as the combination of benchmark antibodies, C9B7W and S1. FS18-29/4420 alone had no noticeable impact on tumour growth and S1 and C9B7W both had a mild effect on resulting tumour growth.
Figure 8:
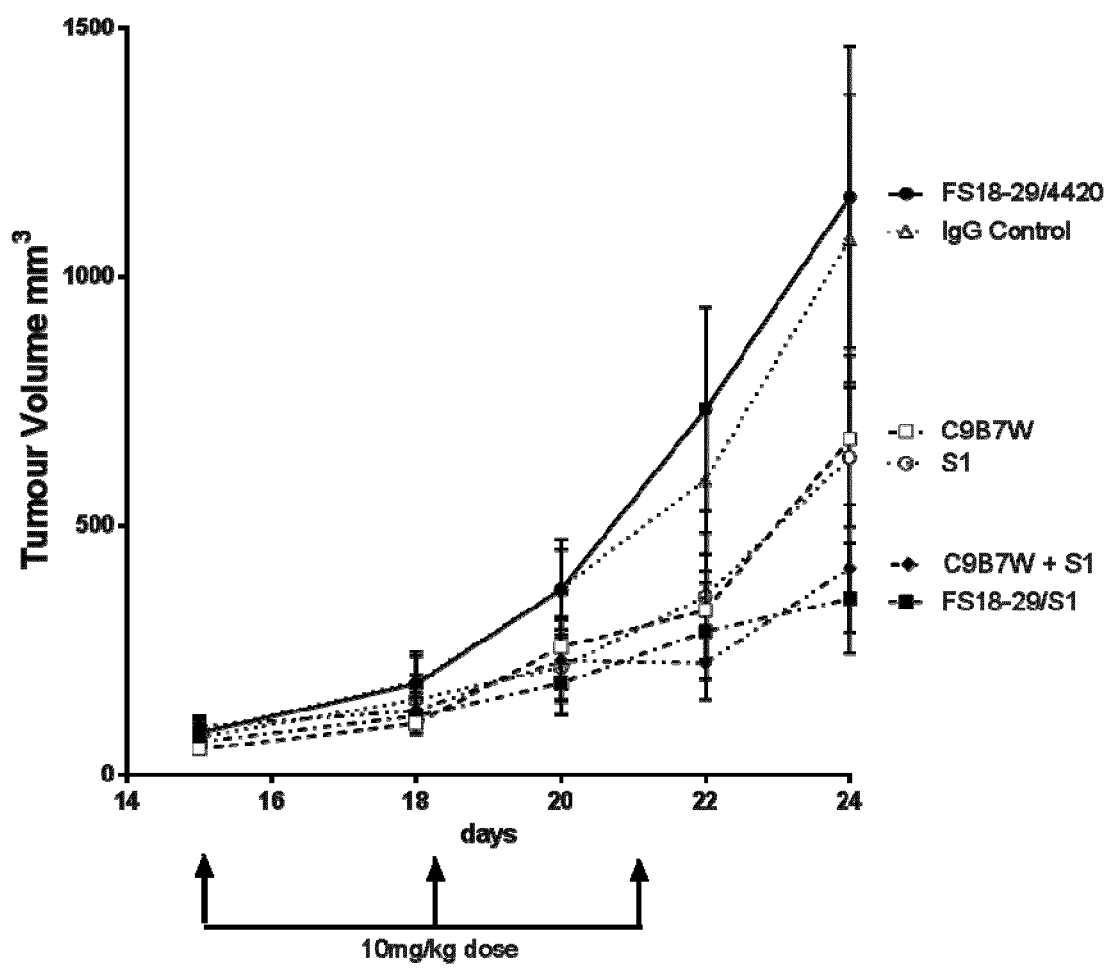
FIG. 8 shows tumour growth curves of the established MC38 syngeneic tumour model. LAG-3/PD-L1 mAb$^2$ (FS18-29/S1) treated mice had tumours volumes similar to those treated with a combination of benchmark mAbs, C9B7W and S1. Mice treated with S1 or C9B7W alone showed intermediate tumour volumes whereas LAG-3/4420 mAb$^2$ treatment had no impact on tumour growth.

The trial was halted at day 24 when the tumour burden was considered close to restrictions. All mice were humanely sacrificed and the tumours were excised and weighed. The results are shown in FIGS. 7 and 8.

Effective control or suppression of tumour growth in syngeneic tumour models in mice is best accomplished through therapeutic intervention at early time points (starting tumour volumes of less than 40 mm$^3$). The later the intervention is administered, the more difficult it is to observe positive effects with respect to tumour growth, though perhaps this is more akin to the situation in the human clinical setting.

FS18-29/S1 had a positive effect in both suppressing tumour growth and preventing the establishment of MC38 colon carcinoma in immune competent mice when given at early time points in C57BL/6 mice. When administered at later time points (starting tumour volumes of 50-125 mm$^3$), FS18-29/S1 was just as effective in suppressing tumour growth as the combination of benchmark antibodies. FS18-29/4420 alone had no noticeable impact on tumour growth and S1 and C9B7W both had a mild effect on resulting tumour growth.

4.3 Activity of mAb$^2$ Molecules in a CT26 Non-Established Tumour Model

The CT26 syngeneic tumour model was used in this experiment as CT26 tumours are known to express PD-L1 on their cell surface and to be highly immunogenic resulting in increased LAG-3 expression on immune cells in the tumour and periphery.

The surrogate mouse mAb$^2$ FS18-7-108-29/S1 containing the LALA mutation (SEQ ID NO: 117 and 119), referred to as FS18-29/S1, and FS18-7-108-35/S1 containing the LALA mutation (SEQ ID NO: 120 and 119), referred to as FS18-35/S1, were tested for in vivo activity in a CT26 syngeneic mouse tumour growth model. The ability of the mAb$^2$ to inhibit tumour growth was compared to that of the LAG-3/mock mAb$^2$, FS18-7-108-29/4420 containing the LALA mutation (SEQ ID NO: 132 and 85), referred to as FS18-29/4420, and FS18-7-108-35/4420 containing the LALA mutation (SEQ ID NO: 133 and 85), referred to as FS18-35/4420, the benchmark LAG-3 mAb C9B7W, the benchmark PD-L1 mAb containing the LALA mutation (SEQ ID NO: 122 and 119) and to a combination of C9B7W and S1.

BALB/c female mice (Charles River) aged 8-10 weeks and weighing 20-25 g each were rested for one week prior to the study start. All animals were micro-chipped and given a unique identifier. Each cohort had 10 mice. The CT26 colon carcinoma cell line (ATCC, CRL-2638) was initially expanded, stored, and then pre-screened by IDEXX Bioresearch for pathogens using the IMPACT I protocol and shown to be pathogen free. CT26 cells (approximately 3-5×10$^6$) were thawed from −150° C. storage and added to 20 ml DMEM (Gibco, 61965-026) with 10% FCS (Gibco, 10270-106) in a T175 tissue culture flask. 7-8 days following tumour cell inoculation, mice were routinely monitored for health and tumour growth appropriate for initiation of the study. When the majority of mice exhibited tumours with a diameter of 3-5 mm$^3$, they were sorted and randomised back into study cohorts. Any mice which did not have tumours at this point were removed from the study.

Figure 9:
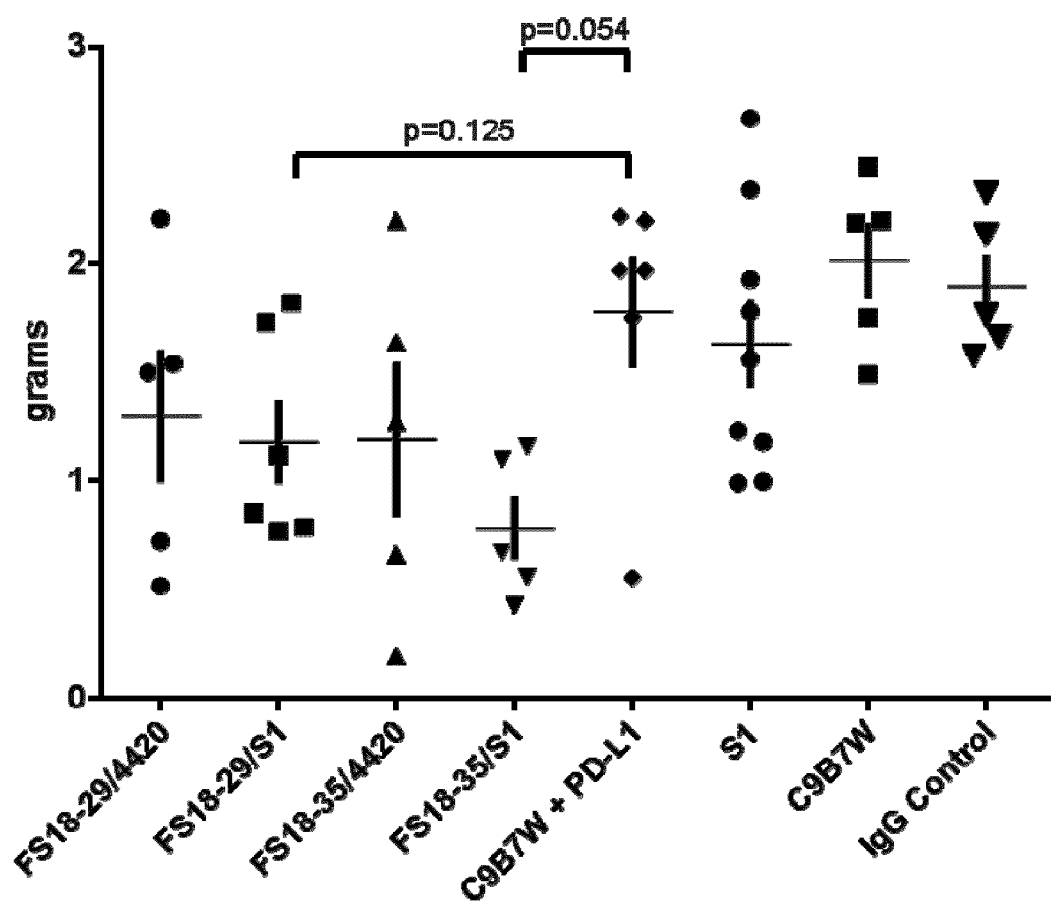
FIG. 9 shows the end tumour weights on day 20 in the non-established CT26 syngeneic tumour model. LAG-3/PD-L1 mAb$^2$ (FS18-29/S1 and FS18-35/S1) suppressed tumour growth to a greater extent than combination of benchmark antibodies, C9B7W and S1.
Figure 10:
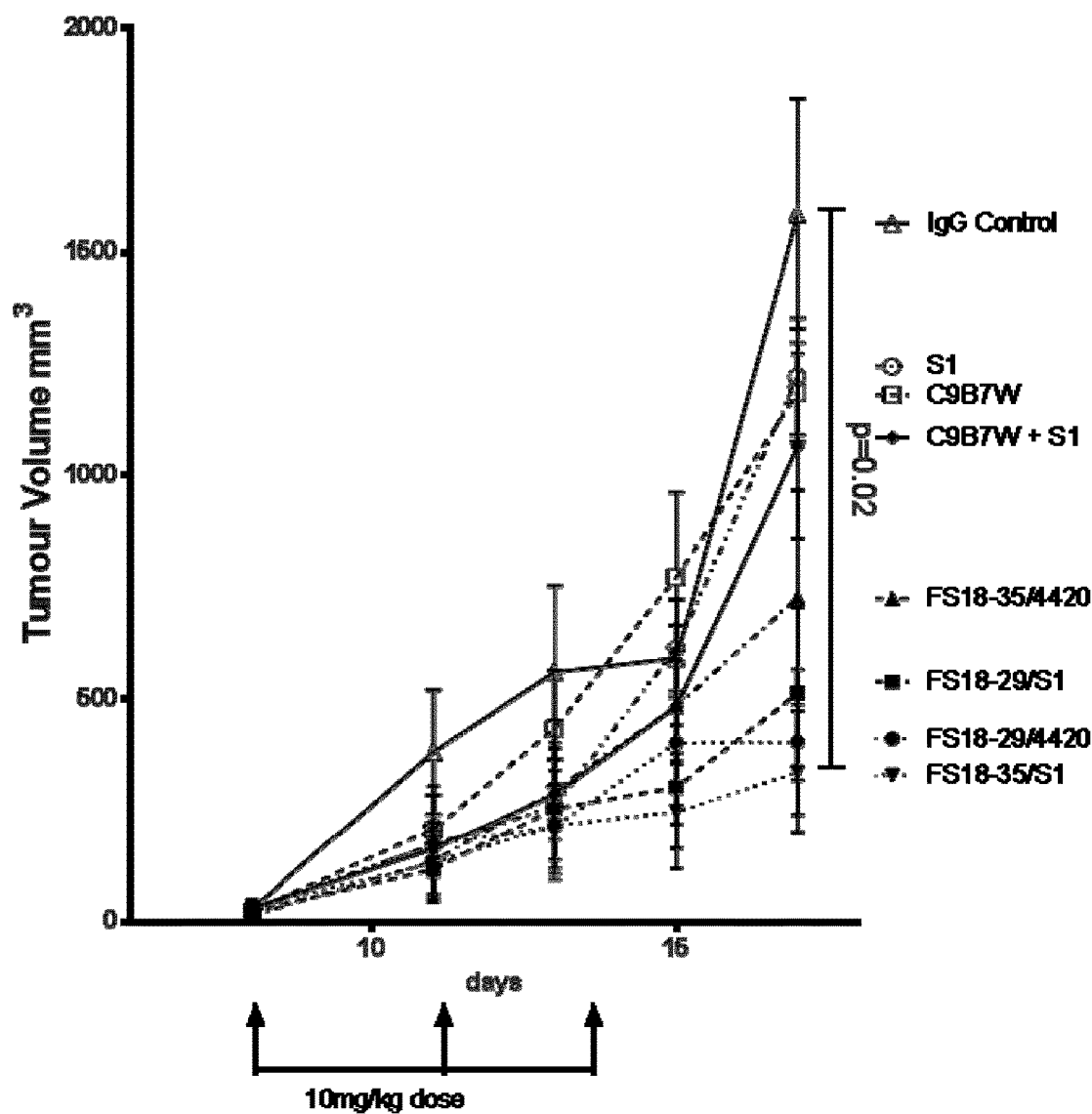
FIG. 10 shows tumour growth curves of the non-established CT26 syngeneic tumour model. There was a demonstrated statistically significant difference in FS18-35/S1 versus IgG control in suppressing tumour growth. Such a statistically significant difference was not observed with the combination of benchmark antibodies, versus the IgG control group.

All of the mAb$^2$ molecules and the control antibodies were analysed within 24 hours of injection by SEC-HPLC profiling and checked for impurities. Antibodies were prepared at a final concentration of 10 mg/kg in PBS and combined with a second antibody in the combination studies. The mAb$^2$ molecules and the control antibodies were administered to the mice on days 8, 11, and 14 following tumour inoculation. Animals were health screened during which time accurate measurements of tumours were taken. Tumour volume measurements were taken with callipers to determine the longest axis and the shortest axis of the tumour. The formula used to calculate the tumour volume was as set out in section 4.1 above:

The trial was halted at day 20 when the tumour burden was considered close to restrictions. All mice were humanely sacrificed and the tumours were excised and weighed. The results are shown in FIGS. 9 and 10.

Statistical analysis of the end tumour weights was performed using a two tailed Student's t-test within the GraphPad Prism software package. Statistical analysis of the tumour growth curves was determined using compare Growth Curves function from the Statistical Modeling package, statmod (Elso et al., 2004 and Baldwin et al., 2007), available from the R Project for Statistical Computing.

There was a demonstrated statistical significant difference between FS18-35/S1 mAb$^2$ and IgG control (normal growth) in suppressing tumour growth. Such a statistically significant difference was not observed with either the combination of benchmark antibodies, or FS18-29/S1 mAb$^2$ versus the IgG control group, or versus any other cohort in this trial.

The CT26 tumour model is an aggressive, fast growing tumour model, one that is inherently prone to mice developing intestinal metastasis, and as a result has a very limited therapeutic window.

Surprisingly the combination of benchmark LAG-3 and PD-L1 antibodies did not significantly suppress tumour growth compared to the IgG control cohort. However, the FS18-35/S1 treated cohort did reveal a significant suppression of growth compared to IgG control. FS18-29/S1, while it did suppress tumour growth as well compared to IgG control, it was not statistically significant. This trial shows a second tumour model in which the mouse reactive LAG-3/PD-L1 mAb$^2$ has demonstrated a positive effect in slowing tumour growth at least to the same degree as administration of a combination of benchmark monoclonal antibodies.

4.4 Effect of LALA Mutation on Tumour Growth Inhibition in the MC38 Non-Established Tumour Model Two mAb$^2$ (FS18-7-108-29/S1 LALA and FS18-7-108-29/S1) were tested to examine potential differences in anti-tumour activity of these mAb$^2$ with and without the LALA mutation in the Fc region. The surrogate mouse mAb$^2$ FS18-7-108-29/S1 referred to as FS18-29/S1 with (SEQ ID NO: 117 and 119) and without LALA mutation (SEQ ID NO: 118 and 119) were tested for in vivo activity using a MC38 syngeneic mouse tumour growth model. The ability of the mAb$^2$ to inhibit tumour growth was compared to that of the LAG-3/mock mAb$^2$, FS18-7-108-29/4420 with (SEQ ID NO: 132 and 85) and without LALA mutation (SEQ ID NO: 134 and 85) referred to as FS18-29/4420LALA and FS18-29/4420 and a combination of the LAG-3/mock mAb$^2$ with and without LALA mutation with the benchmark PD-L1 mAb S1 with (SEQ ID NO: 122 and 119) and without the LALA mutation (SEQ ID NO: 123 and 119).

C57BL/6 female mice (Charles River) aged 8-10 weeks and weighing 20-25 g each were rested for one week prior to the study start. All animals were micro-chipped and given a unique identifier. Each cohort had 10 mice. The MC38 colon carcinoma cell line (S. Rosenberg, NIH) was initially expanded, stored, and then pre-screened by IDEXX Bioresearch for pathogens using the IMPACT I protocol and shown to be pathogen free. MC38 cells (approximately 3-5×10$^6$) were thawed from −150° C. storage and added to 20 ml DMEM (Gibco, 61965-026) with 10% FCS (Gibco, 10270-106) in a T175 tissue culture flask. Mice were anaesthetised using isofluorane (Abbot Laboratories) and 2×10$^6$ cells in 100 µl were injected subcutaneously into the left flank of each mouse. Mice were allowed to recover under observation and the inoculation date noted as Day 0. 7-8 days following tumour cell inoculation, mice were routinely monitored for health and tumour growth appropriate for initiation of the study. Any mice which did not have tumours at this point were removed from the study.

All of the mAb$^2$ molecules and the control antibodies were analysed within 24 hours prior to injection by SEC-HPLC profiling and checked for impurities. Antibodies were prepared at a final concentration of 10 mg/kg in PBS and combined with a second antibody in the combination studies. The mAb$^2$ molecules and the control antibodies were administered to the mice on days 8, 11, and 14 following tumour inoculation by IP injection. Animals were health screened under anaesthesia three times a week in a blinded fashion, during which time accurate measurements of tumours were taken. Tumour volume measurements were taken with callipers to determine the longest axis and the shortest axis of the tumour. The formula used to calculate the tumour volume was as set out in section 4.1.

Figure 11:
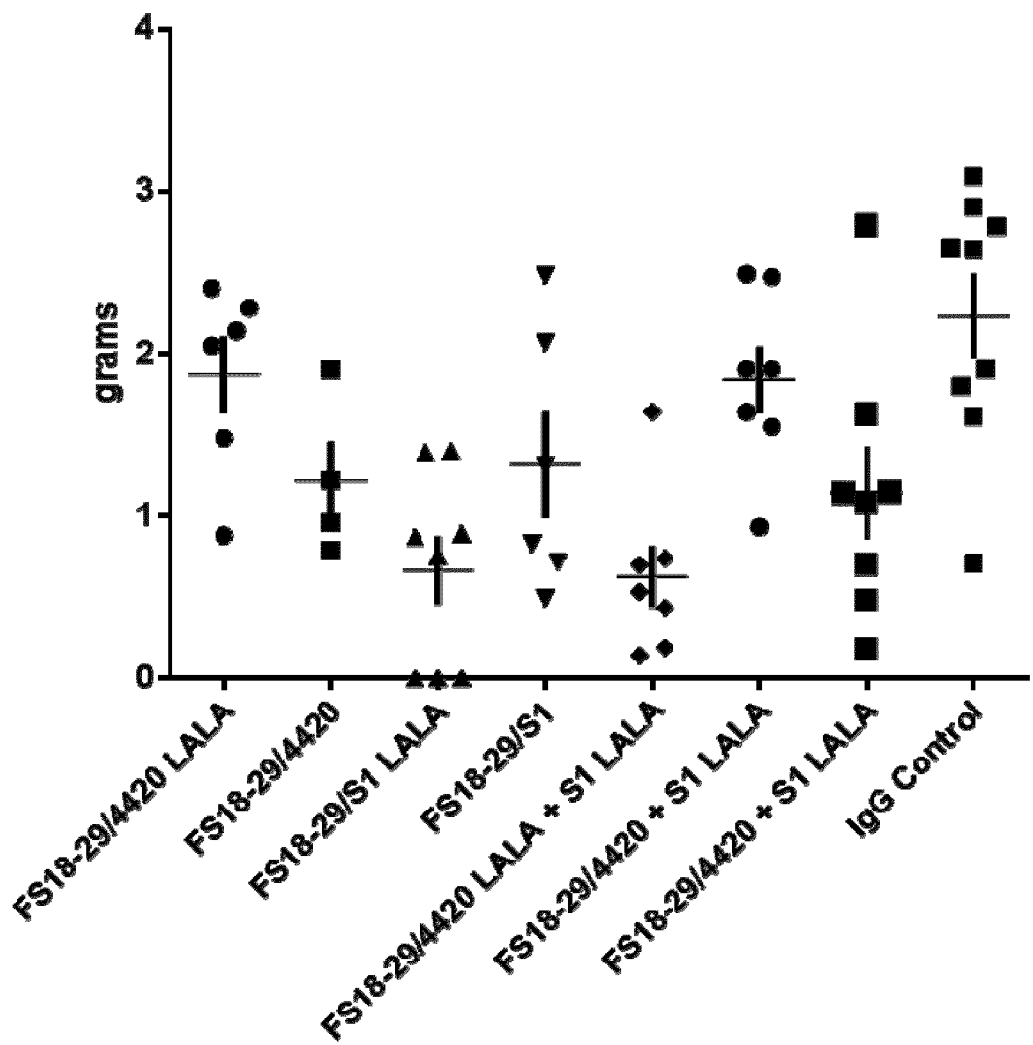
FIG. 11 shows the end tumour weights on day 22 in the non-established MC38 syngeneic tumour model used to compare the effect of the LALA mutation in the mAb$^2$ on tumour growth inhibition. There was no statistically significant difference in end tumour weight between mice treated with mAb$^2$ with and without the LALA mutation.
Figure 12:
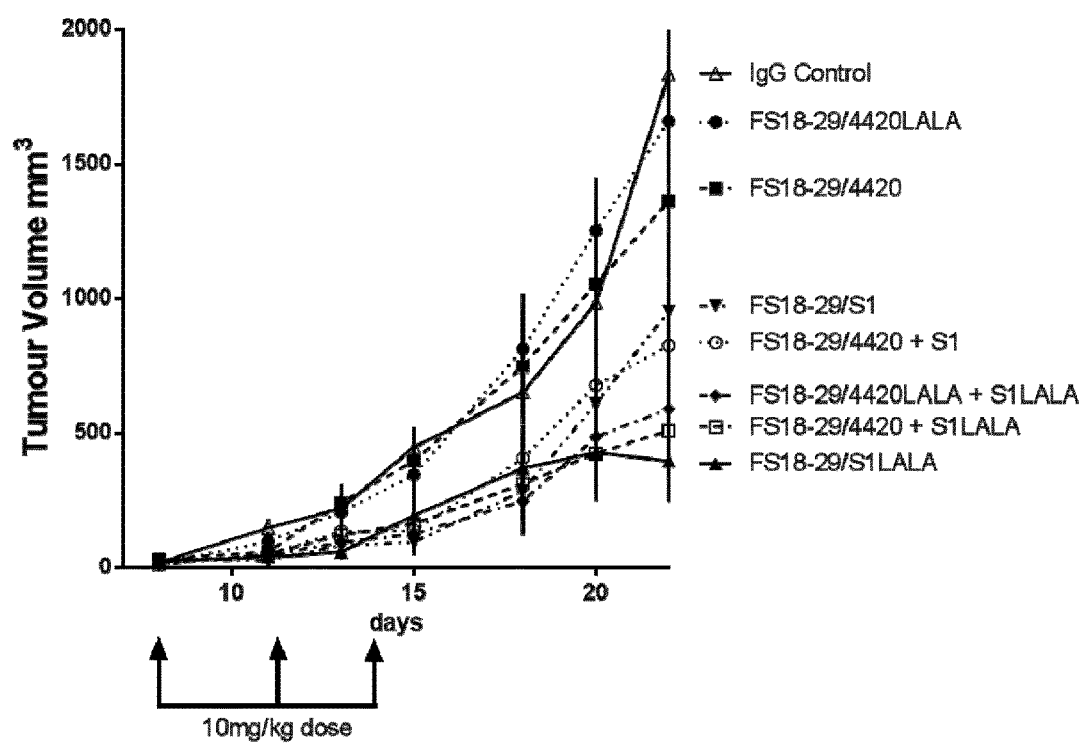
FIG. 12 shows tumour growth curves of the non-established MC38 syngeneic tumour model used to compare the effect of mAb$^2$ with and without the LALA mutation on tumour growth inhibition. There was no statistically significant difference in the tumour growth curves between mice treated with mAb$^2$ with and without the LALA mutation, however there was a trend toward increased tumour growth inhibition by molecules containing the LALA mutation.

All mice were humanely sacrificed and the tumours were excised and weighed. The results are shown in FIGS. 11 and 12.

This trial confirms that the presence or absence of the LALA mutation, which abrogates ADCC activity, has no statistically significant effect on tumour growth in the MC38 colon carcinoma model, however those mAb$^2$ which included the LALA mutation tended to result in increased tumour growth suppression. Nevertheless, the rationale for including the mutation to potentially inhibit ADCC activity against T cells expressing LAG-3 or PD-L1 is justified as the LALA mutation has no detrimental effect on the anti-tumour activity of LAG-3/PD-L1 mAb$^2$. There was some evidence to suggest that inclusion of the LALA mutation was only critical for the PD-L1 antibody.

This trial also examined whether the LAG-3/PD-L1 mAb$^2$ may have increased efficacy over administration of the individual antibodies (LAG-3 LALA+PD-L1 LALA). In this case there was no significant difference between these two cohorts. Both groups suppressed growth in the MC38 colon carcinoma model.

4.5 Conclusion

Overall, it is clear from the above results that there is a synergistic effect on tumour growth suppression when a mAb$^2$ molecule comprising binding sites for both LAG-3 and PD-L1 is administered to mice in the mouse models tested. Based on these results, it is expected that the antibody molecules of the invention will show a superior effect in the treatment of cancer in human patients, in particular in suppressing tumour growth, than administration of two separate molecules which bind LAG-3 and PD-L1, respectively.

Example 5: Effect of mAb2 Treatment on T Cell LAG-3 Expression

The mechanism by which the surrogate mouse mAb$^2$ FS18-7-108-29/S1 containing the LALA mutation, (SEQ ID NOs: 117 and 119) referred to as FS18-29/S1 led to decreased tumour burden was tested in a MC38 syngeneic mouse tumour growth model expressing ovalbumin (MC38.OVA). The effect of FS18-29/S1 was compared to that of the LAG-3/mock mAb$^2$, FS18-7-108-29/4420 containing the LALA mutation (SEQ ID NOs: 132 and 85), referred to as FS18-29/4420, the benchmark PD-L1 mAb S1 containing the LALA mutation (SEQ ID NOs: 122 and 119) and to a combination of FS18-29/4420 and S1.

On the day of implant, cultured MC38.OVA cells were harvested during log phase growth (Confluency ~75%) and resuspended in PBS at a concentration of 1×10$^7$ cells/mL. Tumours were initiated by first anesthetizing each animal with isoflurane, then subcutaneously implanting 1×10$^6$ MC38.OVA cells (0.1 mL suspension) into the left flank of each test animal. Eleven days after tumour cell implantation animals were randomised, using a deterministic randomisation method, into five groups with individual tumour volumes of 32 to 62.5 mm$^3$. Animals were dosed at 10 mg/kg antibody or mAb$^2$ on day 12, 14 and 16 after tumour inoculation, and tumours collected from three animals/group at days 19 and 23 after tumour inoculation. GentleMACS™ Dissociator was used to dissociate the tumour with cells subsequently sieved through a 70 µm cell strainer to obtain a single cell suspension. 1×10$^6$ cells/well on a 96-well plate were resuspended in FACS buffer with 1:3000 viability stain and Fc block (anti-CD16/32 antibody). Cells for FACS analysis were stained using a Master Mix that included labelled antibodies against CD43, CD8a, CD4, FoxP3, and LAG-3. For the FoxP3 intracellular staining cells were fixed and permeabilized prior to staining with the FoxP3 antibody. Samples were run on the Canto II flow cytometer with a compensation matrix and a minimum of 500,000 events counted.

Figure 13:
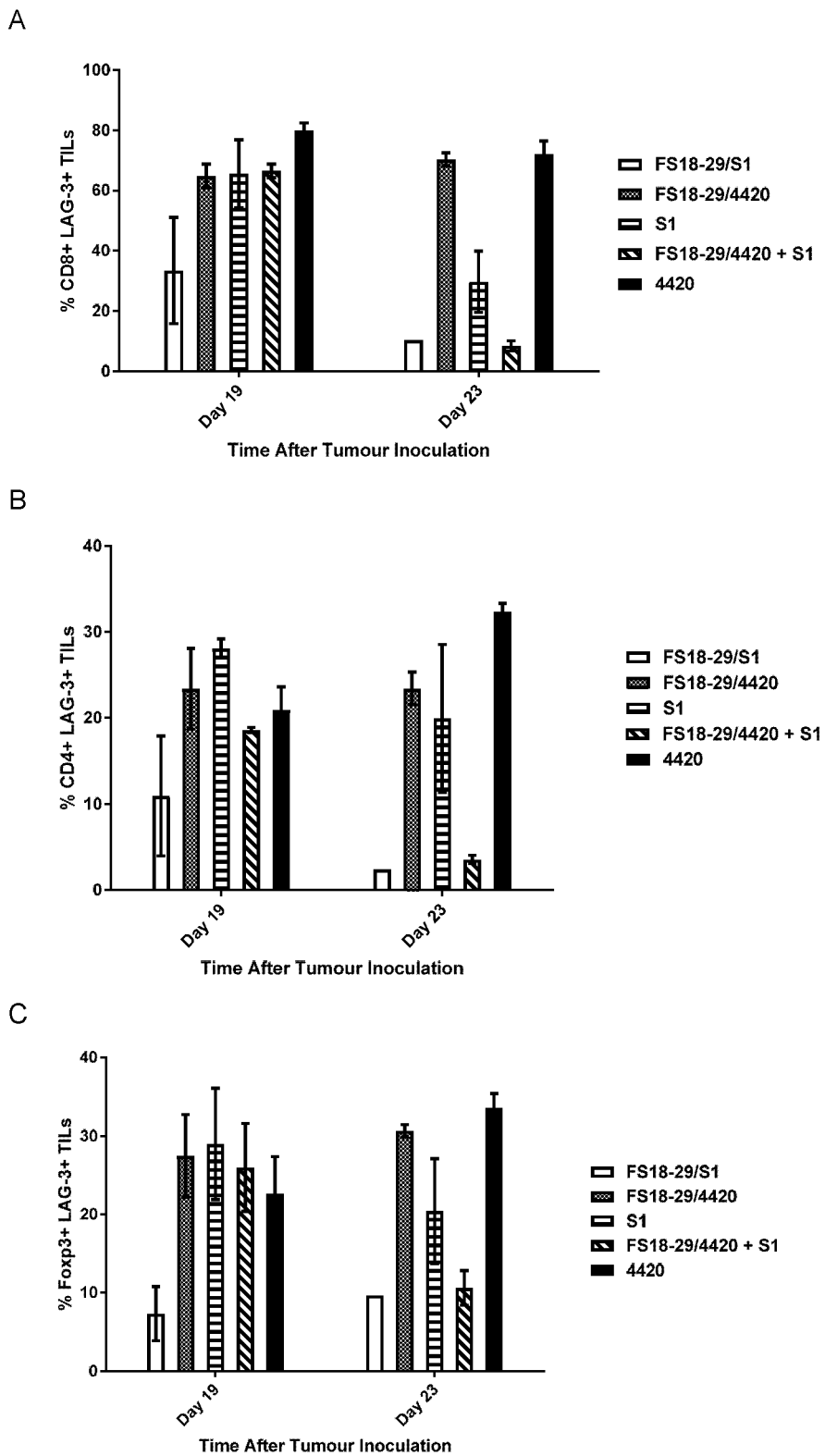
FIG. 13 shows the effect of mAb$^2$ treatment on T cell LAG-3 expression. LAG-3 expression on CD8 (A), CD4 (B) and FoxP3 (C) tumour infiltrating lymphocytes (TILs) treated with mAb$^2$ FS18-29/S1, FS18-29/4420, S1, FS18-29/4420 and S1, or control antibody 4420 is shown at day 19 and 23 after tumour inoculation, corresponding to days 3 and 7 after the last mAb$^2$/antibody dosing, respectively. LAG-3 expression was decreased after treatment with mAb$^2$ FS18-29/S1 at day 19 and 23. Animals given a combination of FS18-29/4420 and S1 also showed a decrease in LAG-3 expression but the effect was delayed until day 23, while FS18-29/4420 or S1 administered individually resulted in little to no decrease in LAG-3 expression.

In this experiment, TILs were examined for LAG-3 expression after the third dose of antibody/mAb$^2$ had been administered, when a separation in the growth of the tumour between control and mAb$^2$ treatments is seen but before there is a large difference between tumour sizes which might skew results. At this time point, LAG-3 expression on TILs was found to be markedly decreased in animals treated with the mAb$^2$ FS18-29/S1 or with the combination of FS18-29/4420 and S1. Specifically, as shown in FIG. 13, LAG-3 expression on CD8, CD4 and FoxP3 tumour infiltrating lymphocytes (TILs) was decreased after treatment with FS18-29/S1 at day 19 and 23 after tumour inoculation, which corresponds to 3 and 7 days after the last antibody/mAb$^2$ dosing, respectively. The decrease in LAG-3 expression was more pronounced at day 23 but was still evident at day 19. Animals given a combination of FS18-29/4420 and S1 also show a decrease in LAG-3 expression on TILs but the effect was delayed until day 23, while treatment with FS18-29/4420 or S1 administered individually had little to no effect on LAG-3 expression on TILs.

These results show that dual inhibition of LAG-3 and PD-L1 is required for a decrease in LAG-3 expression by TILs, as this phenomenon was not seen in animals treated with single agents against LAG-3 or PD-L1. Without wishing to be bound by theory, it is thought that dual anti-LAG-3 and anti-PD-L1 treatment leads to a decrease in LAG-3 expression on TILS, thereby reducing the inhibitory effect of LAG-3 and allowing the TILs to overcome exhaustion. Once the TI Ls become activated, they are able to recognise neo-antigens expressed by the tumour and mount a response against it. This is therefore thought to be the mechanism by which treatment with anti-LAG3/PD-L1 mAb$^2$ results in a reduction in the tumour burden.

Example 6: Antibody Dependent Cellular Cytotoxicity and Complement Dependent Cytotoxicity Activity of mAb²

IgG1 antibodies usually exhibit effector functions via conserved interaction sites within the constant region of the molecule. These include Antibody Dependent Cellular Cytotoxicity (ADCC), mediated by binding to FcγR expressed on Monocytes/Macrophages, dendritic cells, NK cells, neutrophils and other granulocytes, and Complement Dependent Cytotoxicity (CDC), mediated by induction of the complements cascade initiated by binding to C1q complement component. Since LAG-3 is predominantly expressed on activated T cells and PD-L1 is expressed on these but also on tumour cells at high levels, the ability of mAb² FS18-7-9/84G09 (SEQ ID NOs 94 and 116) to induce ADCC and CDC was investigated.

Specifically, it was tested whether FS18-7-9/84G09 treatment of LAG-3 or PD-L1 expressing cells, followed by incubation with either NK cells or complement, induces lysis of the respective target cells. In addition, since FS18-7-9/84G09 is a bispecific antibody, it was also tested whether target engagement on one of the specificities affects effector function towards cells expressing the target for the other specificity.

Understanding the effector functions of mAb² FS18-7-9/84G09 is useful for a number of reasons, including determining whether a mutation which reduces effector functions, such as the LALA mutation, should be included in the molecule to protect LAG-3 expressing effector T cells engaged in tumour killing from FS18-7-9/84G09-mediated ADCC and/or CDC.

6.1 Study Design

Raji cells recombinantly expressing LAG-3 or PD-L1 were used for all assays, using their endogenous expression of CD20 as a control for targeting with a generic version of Rituximab to demonstrate functional activity of the added complement and NK cell preparations independent of the recombinant expression of the target proteins. Target expression was confirmed prior to these experiments.

To determine the basic CDC activity towards LAG-3 or PD-L1 expressing cells, this activity was measured using LDH release, measured by conversion of a substrate into a fluorescent dye (CytoTox-ONE™ by Promega). To measure which target cells in a cell mixture comprising both LAG-3 expressing cells and PD-L1 expressing cells were being lysed, differential CDC was measured by flow cytometry of differentially fluorescently labelled target cells after incubation with the mAb²/antibody, detecting dead cells using a fluorescent dye excluded from live cells.

In order to determine ADCC activity towards LAG-3 or PD-L1 expressing cells, this activity was measured using NK cells isolated from frozen PBMC and LDH release measured colourimetrically (CytoTox 96 by Promega). For all these studies, Rituximab in various isotypes and Fc configurations was used as a control. No reliable method for measuring ADCC differentially is known, so differential ADCC activity was not measured.

In all experiments, the PD-L1 specific mAb (84G09) and the LAG-3 specific mAb (25F7) were used as controls. An IgG isotype control (4420) which was either used as negative control or to generate the CDC background activity was also used. The LALA versions of the respective antibodies and mAb² (excluding 25F7) were also compared to the IgG1 wild-type versions in the CDC and ADCC assays to determine the effect of this mutation on these effector functions.

6.2 Materials and Methods

6.2.1 CDC Assays

All antibodies/mAb², including Rituximab, were diluted in 10 point 1 in 2 serial dilutions. Control wells containing the IgG (4420 LALA) at the highest concentration used were also prepared. Cell suspensions of Raji cells recombinantly expressing LAG-3 or PD-L1 respectively, were prepared in serum free medium for the LDH release assay and added to an equal volume of the prepared antibodies/mAb².

For the Flow Cytometry based CDC assay, cell suspensions of $5 \times 10^7$ cells were prepared and resuspended in either 0.5 µM CellTracker deep red (CellTracker™ Deep Red, Thermo Fisher, #C34565) or 5 µM for CellTracker Green (CellTracker™ Green CMFDA (5-chloromethylfluorescein diacetate, Thermo Fisher, #C7025) in serum free medium. After a 30 min incubation at 37° C., cells were washed in serum free medium and either added to the prepared antibody/mAb²-containing wells directly, or combined with the other differentially stained cell line at equal volumes and then added to the antibody/mAb²-containing wells as described above. For both assays, after a 30 min incubation under cell culture conditions, wells were topped up with an equal volume of baby rabbit complement, 10% in serum free medium (Baby Rabbit Complement, TEBU-bio, #CL3441). Plates were incubated for 4 hrs in cell culture conditions. For the LDH release CDC assay, 100% lysis controls were generated by adding Triton X 100 to half of the 4420 LALA treated wells and the Cytotox assay was performed according to manufacturer's instructions (CytotoxOne, Promega, G7891). After obtaining the reads, the signal from the 100% lysis controls was set to 100% and the signals from the sample wells were calculated as a percentage of that level.

For the Flow Cytometry based CDC assay, at the end of the incubation period, the dead cell dye (SYTOX® Blue Dead Cell Stain, Thermo Fisher, #S34857) was diluted 1 in 500 in PBS and wells were topped up with an equal volume. Flow Cytometry was performed on a Cytoflex flow cytometer gating on the intact cell populations based on FSC and SSC and detecting the percentage of Sytox positive cells (channel PB450) of both the CellTracker™ Deep Red positive and the CellTracker™ Green CM FDA positive cell populations.

6.3.2 ADCC Assay

ADCC was measured as described previously (Broussas, Matthieu; Broyer, Lucile; and Goetsch, Liliane. (2013) Evaluation of Antibody-Dependent Cell Cytotoxicity Using Lactate Dehydrogenase (LDH) Measurement in *Glycosylation Engineering of Biopharmaceuticals: Methods and Protocols*, Methods in Molecular Biology. New York: Springer Science+ Business Media. Volume 988, pp 305-317). Briefly, target cells were pre-incubated with the antibodies before adding primary NK cells isolated from human PBMCs (NK cell isolation kit, Miltenyi Biotec, 130-092-657) at a ratio of 20 to 1 for 4 hrs. The cytotoxicity assay was performed following manufacturer's instructions (CytoTox 96 Non-Radioactive Cytotoxicity Assay, Promega, G1780). % lysis was calculated based on 100% target cell lysis, taking into account spontaneous lysis of effector and target cells.

6.3 Results and Conclusions

6.3.1 CDC Assay

Figure 14:
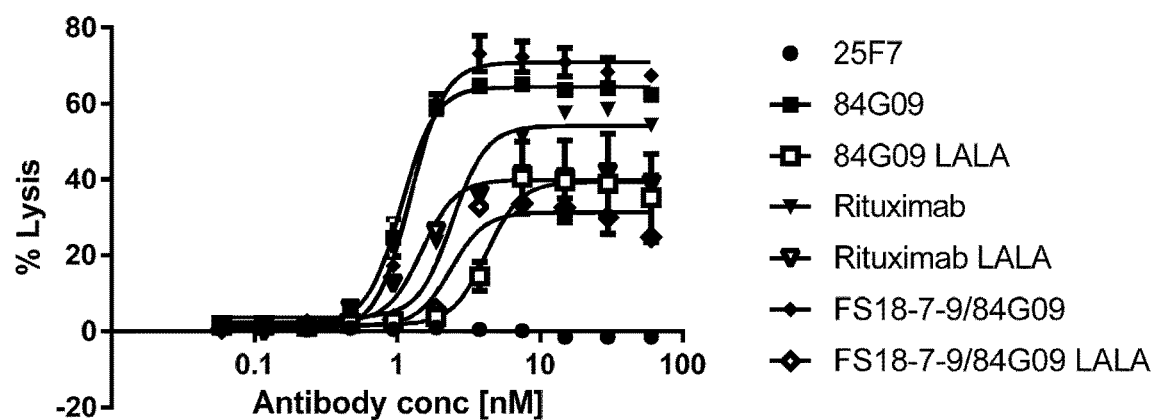
FIG. 14 shows the percentage of lysis of PD-L1 and LAG-3 expressing Raji cells following various antibody/mAb$^2$ treatments using a lactate dehydrogenase (LDH) release CDC assay. A and B show CDC-mediated lysis of PD-L1 and LAG-3 expressing Raji cells, respectively. Cells were incubated with anti-LAG-3 antibody 25F7, anti-PD-L1 antibody 84G09, anti-PD-L1 antibody 84G09 comprising the LALA mutation, anti-CD20 antibody Rituximab, mAb$^2$ FS18-7-9/84G09, mAb$^2$ FS18-7-9/84G09 comprising the LALA mutation, or Rituximab comprising the LALA mutation. Release of LDH was measured 4 hrs after treatment with baby rabbit complement and expressed as percentage compared to total lysis. The concentration of the antibody/mAb$^2$ treatment is indicated on the X-axis. A shared value was set for the slopes of all curves in order to be able to compare across the curves.
Figure 14:
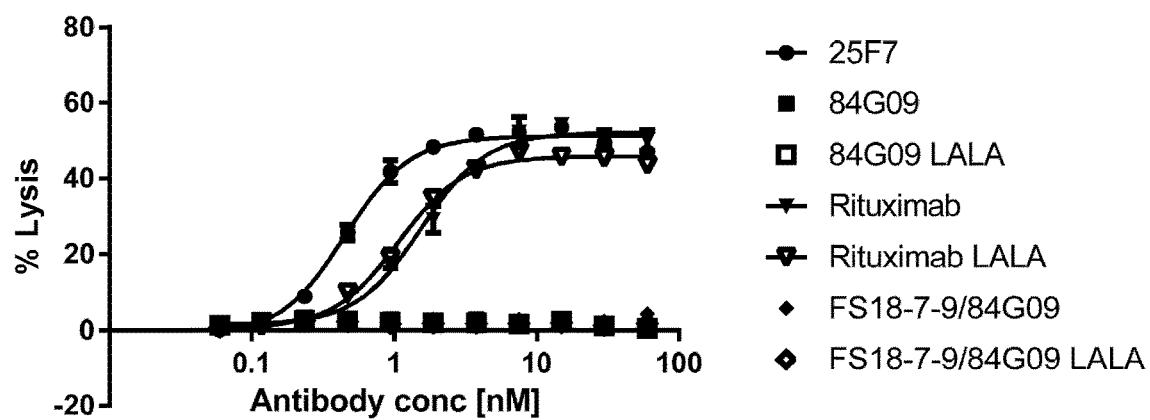

PD-L1 expressing Raji cells were targeted by the anti-CD20 antibody Rituximab, which resulted in a maximum lysis of <60% when measuring CDC by generic LDH release. Anti-PD-L1 antibody 84G09 (which comprises the F(ab)₂ portion of mAb² FS18-7-9/84G09), and FS18-7-9/84G09 in IgG1 format, showed higher maximum lysis and also higher lysis potency, with estimated half maximal doses of about half of that required by Rituximab in IgG1 format. This shows that the introduction of the LAG-3 binding site into the 84G09 antibody did not change its PD-L1 targeting activity with respect to potency or max response, as both were very similar when 84G09 and FS18-7-9/84G09 were compared. The introduction of the LALA mutation resulted in a reduced max response for Rituximab, 84G09 and FS18-7-9/84G09, however, the potency was only reduced for 84G09 and FS18-7-9/84G09. As expected, the anti-LAG-3 antibody 25F7 had no effect on cell viability of the PD-L1 expressing Raji cells, as these cells did not express human LAG-3. These results are shown in FIG. 14A.

LAG-3 expressing Raji cells were targeted for CDC by the anti-CD20 antibody Rituximab, however, the LAG-3 antibody 25F7 showed even better potency with an estimated half maximal dose of about half of that required for Rituximab. None of the other antibodies showed any CDC activity against LAG-3 expressing Raji cells, including FS18-7-9/84G09. The introduction of the LALA mutation had very limited effect on the CDC activity of Rituximab (FIG. 14B).

6.3.2 Differential CDC Assay

Figure 15:
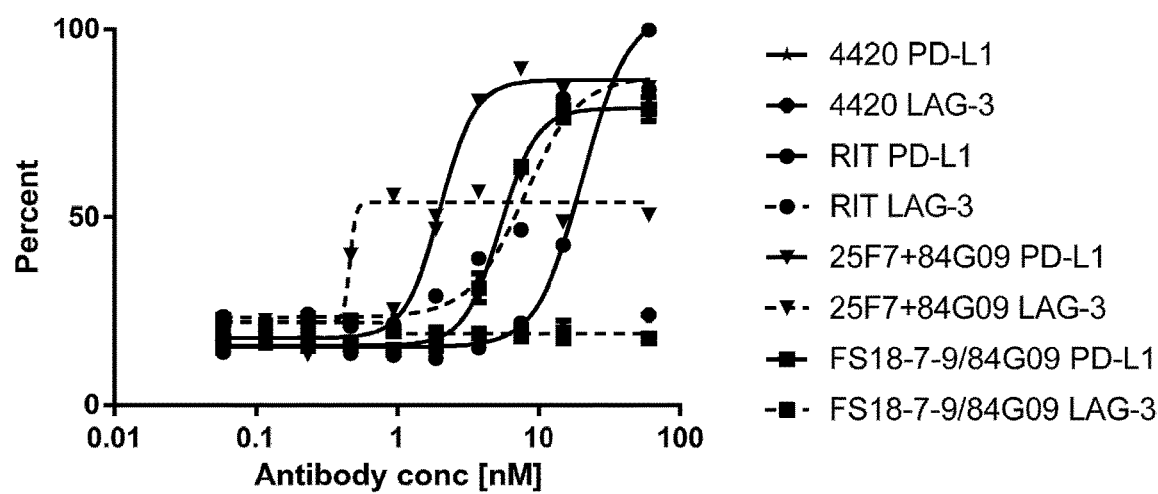
FIG. 15 shows the percentage of dead PD-L1 and LAG-3 expressing Raji cells following various treatments using a flow cytometry based CDC assay. A mixture of differentially fluorescently labelled PD-L1 and LAG-3 expressing cells were incubated with control antibody 4420, anti-CD20 antibody Rituximab (RIT), a combination of anti-LAG-3 antibody 25F7 and anti-PD-L1 antibody 84G09, or mAb$^2$ FS18-7-9/84G09. Cells were then treated with baby rabbit complement and stained using a dye only staining dead cells. The percentage of dead cells in the two cell populations was evaluated as a percentage of total cells. The cell type (PD-L1 expressing or LAG-3 expressing, identified by the differential fluorescent labels) evaluated following each treatment is indicated in FIG. 15 after the name of the relevant treatment, see e.g. 4420 PDL1, which refers to evaluation of viability of PD-L1 expressing Raji cells following treatment with control antibody 4420. The concentration of the antibody/mAb$^2$ treatment is indicated on the X-axis

A differential CDC assay, employing flow cytometry, was developed by the inventors to distinguish which target expressing cells were lysed when treated with FS18-7-9/84G09 or control antibodies. This assay was used to confirm the results from the basic LDH release CDC assay described above. Compared to the IgG isotype control antibody (4420), which had no effect on the percentage of live cells, Rituximab mediated a reduction of live cells and an increase of dead cells, both of PD-L1 and LAG-3 expressing cells. However, FS18-7-9/84G09 had no effect on LAG-3 expressing cells, but very efficiently lysed PD-L1 expressing cells. Similarly, the mixture of the LAG-3 specific antibody 25F7 and the PD-L1 antibody 84G09 also showed a dose-dependent decrease in live cells and a reciprocal increase in dead cells, however, the maximal lysis of LAG-3 expressing cells was only just over 50% of cells, but was reached already at a concentration around 1 nM, the lowest dose to achieve maximal lysis of all antibodies tested. This confirms the previous finding that the LAG-3 binding site in the CH3 domain of FS18-7-9/84G09 does not induce CDC mediated lysis of LAG-3 expressing target cells. In addition, this experiment shows that the presence of LAG-3 expressing cells has no effect on the CDC activity of FS18-7-9/84G09 towards PD-L1 expressing cells. The results are shown in FIG. 15.

6.3.3 ADCC Assay

PD-L1 expressing Raji cells were targeted for ADCC by the anti-CD20 antibody Rituximab, FS18-7-9/84G09, and 84G09 with very similar efficacy and potency, resulting in a maximum lysis of around 40% of cells. Rituximab and 84G09 containing the LALA mutation showed no ADCC-mediated lysis and FS18-7-9/84G09 containing the LALA mutation showed no or very low ADCC-meditated lysis of PD-L1 expressing target cells. The LAG-3 specific antibody 25F7 and the isotype control 4420 with and without the LALA mutation showed no activity in this assay.

Figure 16:
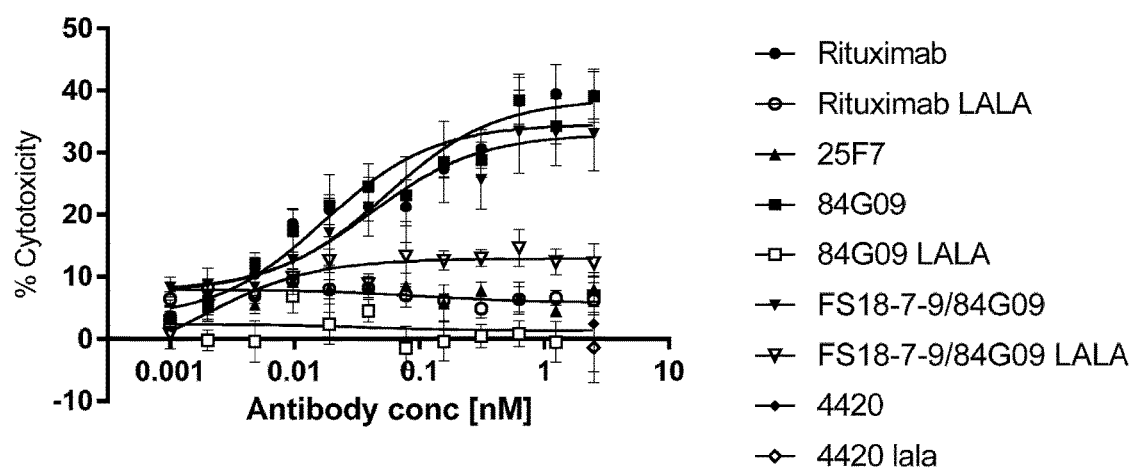
FIG. 16 shows the percentage lysis (cytotoxicity) of PD-L1 and LAG-3 expressing Raji cells following various treatments using a lactate dehydrogenase (LDH) release ADCC assay. Cells were treated with anti-CD20 antibody Rituximab, anti-PD-L1 antibody 84G09, mAb$^2$ FS18-7-9/84G09, Rituximab comprising the LALA mutation, mAb$^2$ FS18-7-9/84G09 comprising the LALA mutation, anti-LAG-3 antibody 25F7, anti-PD-L1 antibody 84G09 comprising the LALA mutation, control antibody 4420, or control antibody 4420 comprising the LALA mutation. Treated cells were then co-incubated with primary NK cells and specific LDH release was measured as a percentage compared to total lysis of target cells. The concentration of the antibody/mAb$^2$ treatment is indicated on the X-axis.
Figure 16:
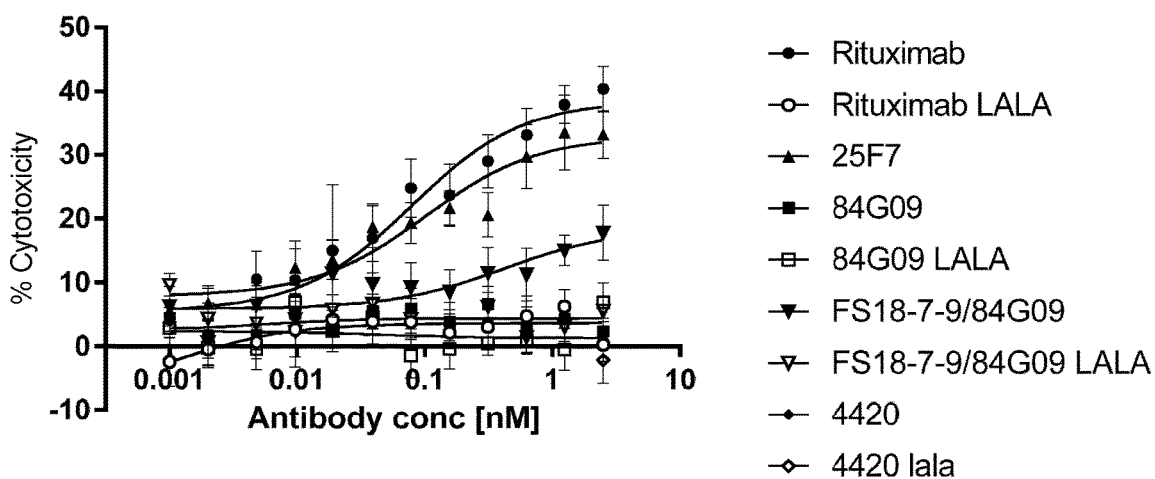

These results show that the introduction of the LAG-3 binding site into antibody 84G09 did not change its PD-L1 targeted ADCC activity in potency or max response, since both were very similar to the PD-L1 specific antibody 84G09. The introduction of the LALA mutation resulted in abrogation of ADCC activity (FIG. 16A).

LAG-3 expressing Raji cells were targeted by Rituximab and 25F7 for ADCC-mediated lysis, resulting in maximum lysis of about 40%. FS18-7-9/84G09 also mediated lysis of LAG-3 expressing cells by ADCC, be it with a much lower potency and efficacy, only reaching just under 20% lysis at 2.5 nM concentration. The introduction of the LALA mutation abrogated all ADCC activity of Rituximab and FS18-7-9/84G09. 84G09 and the isotype control 4420 with and without the LALA mutation showed no ADCC activity in this assay as expected, as these antibodies do not bind LAG-3 (FIG. 16B).

Sequence Listing

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~321 kb), which was created on Dec. 19, 2018, which is incorporated by reference herein.

```
Amino acid sequences of Fcab FS18-7-9 loop regions
FS18-7-9 AB loop - WDEPWGED (SEQ ID NO: 1)
FS18-7-9 CD loop - SNGQPENNY (SEQ ID NO: 2)
FS18-7-9 EF loop - PYDRWVWPDE (SEQ ID NO: 3)

Nucleotide sequence of Fcab FS18-7-9 CH3 domain (SEQ ID NO: 4)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGCTCC
TTCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT CHO codon optimised nucleotide sequence of Fcab FS18-7-9 CH3 domain (SEQ ID NO: 142)
GGCCAGCCCCGGGAACCCCAGGTGTACACACTGCCTCCATCCTGGGATGAGCCCTGGGGCGA
GGATGTGTCTCTGACCTGTCTCGTGAAAGGCTTCTACCCCTCCGATATCGCCGTGGAATGGGAG
AGCAACGGCCAGCCCGAGAACAACTACAAGACCACCCCCCCTGTGCTGGACTCCGACGGCTCA
TTCTTCCTGTACAGCAAGCTGACAGTGCCCTACGACAGATGGGTGTGGCCCGACGAGTTCTCCT
GCTCCGTGATGCACGAGGCCCTGCACAACCACTACACCCAGAAGTCCCTGTCCCTGAGCCCCG
GC Amino acid sequence of Fcab FS18-7-9 CH3 domain (SEQ ID NO: 5)
GQPREPQVYTLPPSWDEPWGEDVSLTCLVKGFYPSDIAVEWESNGQPENNYKTTPPVLDSDGSFFL
YSKLTVPYDRWVWPDEFSCSVMHEALHNHYTQKSLSLSPG
```

Amino acid sequence of Fcab FS18-7-9 CH3 domain comprising C-terminal lysine (SEQ ID NO: 135)
GQPREPQVYTLPPSWDEPWGEDVSLTCLVKGFYPSDIAVEWESNGQPENNYKTTPPVLDSDGSFFL
YSKLTVPYDRWVWPDEFSCSVMHEALHNHYTQKSLSLSPGK Amino acid sequence of Fcab FS18-7-9 CH2 and CH3 domains, comprising LALA mutation
(underlined) (SEQ ID NO: 6)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGQPENNYKTTPPVLDSDGSFFLYSKLTVPYDRWVWPDEFSCSVM
HEALHNHYTQKSLSLSPG Amino acid sequence of Fcab FS18-7-9 CH2 and CH3 domains without LALA mutation (SEQ ID NO: 7)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGQPENNYKTTPPVLDSDGSFFLYSKLTVPYDRWVWPDEFSCSVMHE
ALHNHYTQKSLSLSPG Amino acid sequences of Fcab FS18-7-32 loop regions
FS18-7-32 AB loop - WDEPWGED (SEQ ID NO: 1)
FS18-7-32 CD loop - SNGQPENNY (SEQ ID NO: 8)
FS18-7-32 EF loop - PYDRWVWPDE (SEQ ID NO: 3)

Nucleotide sequence of Fcab FS18-7-32 CH3 domain (SEQ ID NO: 9)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGAAATCGCCGTGGAGTGGGAG
AGCAATGGGCAGCCGGAGAACAACTACAAGACCACGCCTCCCGTGCTGGACTCCGACGGCTCC
TTCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-32 CH3 domain (SEQ ID NO: 10)
GQPREPQVYTLPPSWDEPWGEDVSLTCLVKGFYPSEIAVEWESNGQPENNYKTTPPVLDSDGSFFL
YSKLTVPYDRWVWPDEFSCSVMHEALHNHYTQKSLSLSPG Amino acid sequence of Fcab FS18-7-32 CH2 and CH3 domains, comprising LALA mutation
(underlined) (SEQ ID NO: 11)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSEIAVEWESNGQPENNYKTTPPVLDSDGSFFLYSKLTVPYDRWVWPDEFSCSVM
HEALHNHYTQKSLSLSPG Amino acid sequence of Fcab FS18-7-32 CH2 and CH3 domains without LALA mutation (SEQ ID NO: 12)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSEIAVEWESNGQPENNYKTTPPVLDSDGSFFLYSKLTVPYDRWVWPDEFSCSVMHE
ALHNHYTQKSLSLSPG Amino acid sequences of Fcab FS18-7-33 loop regions
FS18-7-33 AB loop - WDEPWGED (SEQ ID NO: 1)
FS18-7-33 CD loop - SNGQPEDNY (SEQ ID NO: 13)
FS18-7-33 EF loop - PYDRWVWPDE (SEQ ID NO: 3)

Nucleotide sequence of Fcab FS18-7-33 CH3 domain (SEQ ID NO: 14)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGCAGCCGGAGGACAACTACAAGACCACGCCTCCCGTGCTGGACTCCGACGGCTCC
TTCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-33 CH3 domain (SEQ ID NO: 15)
GQPREPQVYTLPPSWDEPWGEDVSLTCLVKGFYPSDIAVEWESNGQPEDNYKTTPPVLDSDGSFFL
YSKLTVPYDRWVWPDEFSCSVMHEALHNHYTQKSLSLSPG Amino acid sequence of Fcab FS18-7-33 CH2 and CH3 domains, comprising LALA mutation
(underlined) (SEQ ID NO: 16)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGQPEDNYKTTPPVLDSDGSFFLYSKLTVPYDRWVWPDEFSCSVM
HEALHNHYTQKSLSLSPG Amino acid sequence of Fcab FS18-7-33 CH2 and CH3 domains without LALA mutation (SEQ ID NO: 17)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGQPEDNYKTTPPVLDSDGSFFLYSKLTVPYDRWVWPDEFSCSVMHE
ALHNHYTQKSLSLSPG Amino acid sequences of Fcab FS18-7-36 loop regions
FS18-7-36 AB loop - WDEPWGED (SEQ ID NO: 1)
FS18-7-36 CD loop - SNGQPENNY (SEQ ID NO: 18)
FS18-7-36 EF loop - PYDRWVWPDE (SEQ ID NO: 3)

Nucleotide sequence of Fcab FS18-7-36 CH3 domain (SEQ ID NO: 19)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGCTCC
TACTTCCTCTACAGCAAGCTCACCGTGCCGTATGATAGGTGGGTTTGGCCGGATGAGTTCTCAT
GCTCCGTGATGCATGAGGCTCTGCACAACCACTACACACAGAAGAGCCTCTCCCTGTCTCCGGGT Amino acid sequence of Fcab FS18-7-36 CH3 domain (SEQ ID NO: 20)
GQPREPQVYTLPPSWDEPWGEDVSLTCLVKGFYPSDIAVEWESNGQPENNYKTTPPVLDSDGSYFL
YSKLTVPYDRWVWPDEFSCSVMHEALHNHYTQKSLSLSPG Amino acid sequence of CH2 + CH3 of Fcab FS18-7-36 CH2 and CH3 domains, comprising LALA
mutation (underlined) (SEQ ID NO: 21)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGQPENNYKTTPPVLDSDGSYFLYSKLTVPYDRWVWPDEFSCSVM
HEALHNHYTQKSLSLSPG Amino acid sequence of Fcab FS18-7-36 CH2 and CH3 domains without LALA mutation (SEQ ID NO: 22)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGQPENNYKTTPPVLDSDGSYFLYSKLTVPYDRWVWPDEFSCSVMHE
ALHNHYTQKSLSLSPG Amino acid sequences of Fcab FS18-7-58 loop regions
FS18-7-58 AB loop - WDEPWGED (SEQ ID NO: 1)
FS18-7-58 CD loop - SNGYPEIEF (SEQ ID NO: 23)
FS18-7-58 EF loop - PYDRWVWPDE (SEQ ID NO: 3)

Nucleotide sequence of Fcab FS18-7-58 CH3 domain (SEQ ID NO: 24)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATCCAGAAATCGAATTCAAGACCACGCCTCCCGTGCTGGACTCCGACGGCTCCT
TCTTCCTCTACAGCAAGCTCACCGTGCCTTATGATAGGTGGGTTTGGCCGGATGAGTTCTCATGC
TCCGTGATGCATGAGGCTCTGCACAACCACTACACACAGAAGAGCCTCTCCCTGTCTCCGGGT Amino acid sequence of Fcab FS18-7-58 CH3 domain (SEQ ID NO: 25)
GQPREPQVYTLPPSWDEPWGEDVSLTCLVKGFYPSDIAVEWESNGYPEIEFKTTPPVLDSDGSFFLY
SKLTVPYDRWVWPDEFSCSVMHEALHNHYTQKSLSLSPG Amino acid sequence of Fcab FS18-7-58 CH2 and CH3 domains, comprising LALA mutation
(underlined) (SEQ ID NO: 26)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGYPEIEFKTTPPVLDSDGSFFLYSKLTVPYDRWVWPDEFSCSVMH
EALHNHYTQKSLSLSPG Amino acid sequence of Fcab FS18-7-58 CH2 and CH3 domains without LALA mutation (SEQ ID NO: 27)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGYPEIEFKTTPPVLDSDGSFFLYSKLTVPYDRWVWPDEFSCSVMHEA
LHNHYTQKSLSLSPG Amino acid sequences of Fcab FS18-7-62 loop regions
FS18-7-62 AB loop - WDEPWGED (SEQ ID NO: 1)
FS18-7-62 CD loop - SNGIPEWNY (SEQ ID NO: 28)
FS18-7-62 EF loop - PYDRWVWPDE (SEQ ID NO: 3)

Nucleotide sequence of Fcab FS18-7-62 CH3 domain (SEQ ID NO: 29)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGATCCCAGAATGGAACTATAAGACCACGCCTCCCGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-62 CH3 domain (SEQ ID NO: 30)
GQPREPQVYTLPPSWDEPWGEDVSLTCLVKGFYPSDIAVEWESNGIPEWNYKTTPPVLDSDGSFFL
YSKLTVPYDRWVWPDEFSCSVMHEALHNHYTQKSLSLSPG Amino acid sequence of Fcab FS18-7-62 CH2 and CH3 domains, comprising LALA mutation
(underlined) (SEQ ID NO: 31)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED VSLTCLVKGFYPSDIAVEWESNGIPEWNYKTTPPVLDSDGSFFLYSKLTVPYDRWVWPDEFSCSVMH
EALHNHYTQKSLSLSPG Amino acid sequence of Fcab FS18-7-62 CH2 and CH3 domains without LALA mutation (SEQ ID NO: 32)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGIPEWNYKTTPPVLDSDGSFFLYSKLTVPYDRWVWPDEFSCSVMHEA
LHNHYTQKSLSLSPG Amino acid sequences of Fcab FS18-7-65 loop regions
FS18-7-65 AB loop - WDEPWGED (SEQ ID NO: 1)
FS18-7-65 CD loop - SNGYAEYNY (SEQ ID NO: 33)
FS18-7-65 EF loop - PYDRWVWPDE (SEQ ID NO: 3)

Nucleotide sequence of Fcab FS18-7-65 CH3 domain (SEQ ID NO: 34)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATGCAGAATATAACTATAAGACCACGCCTCCCGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-65 CH3 domain (SEQ ID NO: 35)
GQPREPQVYTLPPSWDEPWGEDVSLTCLVKGFYPSDIAVEWESNGYAEYNYKTTPPVLDSDGSFFL
YSKLTVPYDRWVWPDEFSCSVMHEALHNHYTQKSLSLSPG Amino acid sequence of Fcab FS18-7-65 CH2 and CH3 domains, comprising LALA mutation
(underlined) (SEQ ID NO: 36)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGYAEYNYKTTPPVLDSDGSFFLYSKLTVPYDRWVWPDEFSCSVM
HEALHNHYTQKSLSLSPG Amino acid sequence of Fcab FS18-7-65 CH2 and CH3 domains without LALA mutation (SEQ ID NO: 37)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGYAEYNYKTTPPVLDSDGSFFLYSKLTVPYDRWVWPDEFSCSVMHE
ALHNHYTQKSLSLSPG Amino acid sequences of Fcab FS18-7-78 loop regions
FS18-7-78 AB loop - WDEPWGED (SEQ ID NO: 1)
FS18-7-78 CD loop - SNGYKEENY (SEQ ID NO: 38)
FS18-7-78 EF loop - PYDRWVWPDE (SEQ ID NO: 3)

Nucleotide sequence of Fcab FS18-7-78 CH3 domain (SEQ ID NO: 39)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATAAAGAAGAAAACTATAAGACCACGCCTCCCGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-78 CH3 domain (SEQ ID NO: 40)
GQPREPQVYTLPPSWDEPWGEDVSLTCLVKGFYPSDIAVEWESNGYKEENYKTTPPVLDSDGSFFL
YSKLTVPYDRWVWPDEFSCSVMHEALHNHYTQKSLSLSPG Amino acid sequence of Fcab FS18-7-78 CH2 and CH3 domains, comprising LALA mutation
(underlined) (SEQ ID NO: 41)
APE<u>AA</u>GGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGYKEENYKTTPPVLDSDGSFFLYSKLTVPYDRWVWPDEFSCSVM
HEALHNHYTQKSLSLSPG Amino acid sequence of Fcab FS18-7-78 CH2 and CH3 domains without LALA mutation (SEQ ID NO: 42)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGYKEENYKTTPPVLDSDGSFFLYSKLTVPYDRWVWPDEFSCSVMHE
ALHNHYTQKSLSLSPG Amino acid sequences of Fcab FS18-7-88 loop regions
FS18-7-88 AB loop - WDEPWGED (SEQ ID NO: 1)
FS18-7-88 CD loop - SNGVPELNV (SEQ ID NO: 43)
FS18-7-88 EF loop - PYDRWVWPDE (SEQ ID NO: 3)

Nucleotide sequence of Fcab FS18-7-88 CH3 domain (SEQ ID NO: 44)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGGTTCCAGAACTGAACGTTAAGACCACGCCTCCCGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-88 CH3 domain (SEQ ID NO: 45)
GQPREPQVYTLPPSWDEPWGEDVSLTCLVKGFYPSDIAVEWESNGVPELNVKTTPPVLDSDGSFFL
YSKLTVPYDRWVWPDEFSCSVMHEALHNHYTQKSLSLSPG Amino acid sequence of Fcab FS18-7-88 CH2 and CH3 domains, comprising LALA mutation
(underlined) (SEQ ID NO: 46)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGVPELNVKTTPPVLDSDGSFFLYSKLTVPYDRWVWPDEFSCSVMH
EALHNHYTQKSLSLSPG Amino acid sequence of Fcab FS18-7-88 CH2 and CH3 domains without LALA mutation (SEQ ID NO: 47)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGVPELNVKTTPPVLDSDGSFFLYSKLTVPYDRWVWPDEFSCSVMHEA
LHNHYTQKSLSLSPG Amino acid sequences of Fcab FS18-7-95 loop regions
FS18-7-95 AB loop - WDEPWGED (SEQ ID NO: 1)
FS18-7-95 CD loop - SNGYQEDNY (SEQ ID NO: 48)
FS18-7-95 EF loop - PYDRWVWPDE (SEQ ID NO: 3)

Nucleotide sequence of Fcab FS18-7-95 CH3 domain (SEQ ID NO: 49)
GGCCAGCCTCGAGAACCACAGGTGTACACCCTGCCCCCATCCTGGGATGAGCCGTGGGGTGAA
GACGTCAGCCTGACCTGCCTGGTCAAAGGCTTCTATCCCAGCGACATCGCCGTGGAGTGGGAG
AGCAATGGGTATCAGGAAGATAACTATAAGACCACGCCTCCTGTGCTGGACTCCGACGGCTCCT
TCTTCCTCTACAGCAAGCTCACCGTGCCGTATGATAGGTGGGTTTGGCCGGATGAGTTCTCATG
CTCCGTGATGCATGAGGCTCTGCACAACCACTACACACAGAAGAGCCTCTCCCTGTCTCCGGGT Amino acid sequence of Fcab FS18-7-95 CH3 domain (SEQ ID NO: 50)
GQPREPQVYTLPPSWDEPWGEDVSLTCLVKGFYPSDIAVEWESNGYQEDNYKTTPPVLDSDGSFFL
YSKLTVPYDRWVWPDEFSCSVMHEALHNHYTQKSLSLSPG Amino acid sequence of Fcab FS18-7-95 CH2 and CH3 domains, comprising LALA mutation
(underlined) (SEQ ID NO: 51)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSWDEPWGED
VSLTCLVKGFYPSDIAVEWESNGYQEDNYKTTPPVLDSDGSFFLYSKLTVPYDRWVWPDEFSCSVM
HEALHNHYTQKSLSLSPG Amino acid sequence of Fcab FS18-7-95 CH2 and CH3 domains without LALA mutation
(SEQ ID NO: 52)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSWDEPWGEDVS
LTCLVKGFYPSDIAVEWESNGYQEDNYKTTPPVLDSDGSFFLYSKLTVPYDRWVWPDEFSCSVMHE
ALHNHYTQKSLSLSPG Amino acid sequence of the wild-type human IgG1 CH2 domain (SEQ ID NO: 53)
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAK Amino acid sequence of the human IgG1 CH2 domain comprising the "LALA mutation"
(underlined) (SEQ ID NO: 54)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAK Amino acid sequence of "wild-type" Fcab CH2 and CH3 domains without LALA mutation
(SEQ ID NO: 55).
APELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEA
LHNHYTQKSLSLSPG Amino acid sequence of "wild-type" Fcab CH2 and CH3 domains, comprising LALA mutation
(underlined) (SEQ ID NO: 56)
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFSCSVMH
EALHNHYTQKSLSLSPG Amino acid sequence of the human IgG1 hinge region (SEQ ID NO: 57)
EPKSCDKTHTCPPCP Amino acid sequence of the human IgG1 truncated hinge region (SEQ ID NO: 58)
TCPPCP Amino acid sequence anti-mouse LAG-3 Fcab FS18-7-108-29, comprising LALA mutation
(underlined) (SEQ ID NO: 59)

The CH3 domain is shown in italics. The AB, CD and EF loops of the CH3 domain are shown in bold and underlined.
TCPPCPAPEAAGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPQVYTLPPSWDEP*
*WGEDVSLTCLVKGFYPSDIVVEWESNGQPENNYKTTPPVLDSDGSFFLYSKLTVPFERWMWPDEFS*
*CSVMHEALHNHYTQKSLSLSPG*

Amino acid sequence of the anti-mouse LAG-3 Fcab FS18-7-108-29 without LALA mutation
(SEQ ID NO: 60)
The CH3 domain is shown in italics. The AB, CD and EF loops of the CH3 domain are shown in bold and underlined.
TCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPQVYTLPPSWDEP*
*WGEDVSLTCLVKGFYPSDIVVEWESNGQPENNYKTTPPVLDSDGSFFLYSKLTVPFERWMWPDEFS*
*CSVMHEALHNHYTQKSLSLSPG*

Amino acid sequence of the anti-mouse LAG-3 Fcab FS18-7-108-35, comprising LALA
mutation (underlined) (SEQ ID NO: 61)
The CH3 domain is shown in italics. The AB, CD and EF loop regions are shown in bold and underlined.
TCPPCPAPEAAGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPQVYTLPPSWDEP*
*WGEDVSLTCLVKGFYPSDISVEWESNGQPENNYKTTPPVLDSDGSFFLYSKLTVPFERWMWPDEFS*
*CSVMHEALHNHYTQKSLSLSPG*

Amino acid sequence of the anti-mouse LAG-3 Fcab FS18-7-108-35 without LALA mutation
(SEQ ID NO: 62)
The CH3 domain is shown in italics. The AB, CD and EF loop regions are shown in bold and underlined.
TCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK*GQPREPQVYTLPPSWDEP*
*WGEDVSLTCLVKGFYPSDISVEWESNGQPENNYKTTPPVLDSDGSFFLYSKLTVPFERWMWPDEFS*
*CSVMHEALHNHYTQKSLSLSPG*

Amino acid sequence of the heavy chain of anti-human LAG-3/FITC mAb[2] FS18-7-9/4420
comprising LALA mutation (SEQ ID NO: 63)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSDS</u>
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGQPENNYKTTPP
VLDSDGSFFLYSKLTVPYDRWVWPDEFSCSVMHEALHNHYTQKSLSLSPG Amino acid sequence of the heavy chain of anti-human LAG-3/FITC mAb[2] FS18-7-9/4420
without LALA mutation (SEQ ID NO: 64)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYYSDS</u>
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGQPENNYKTTPPVL
DSDGSFFLYSKLTVPYDRWVWPDEFSCSVMHEALHNHYTQKSLSLSPG Amino acid sequence of the heavy chain of anti-human LAG-3/FITC mAb[2] FS18-7-32/4420
comprising LALA mutation (SEQ ID NO: 65)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSDS</u>
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSEIAVEWESNGQPENNYKTTPP
VLDSDGSFFLYSKLTVPYDRWVWPDEFSCSVMHEALHNHYTQKSLSLSPG Amino acid sequence of the heavy chain of anti-human LAG-3/FITC mAb[2] FS18-7-
32/without LALA mutation (SEQ ID NO: 66)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYYSDS</u>
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP IEKTISKAKGQPREPQVYTLPPSWDEPWGEDVSLTCLVKGFYPSEIAVEWESNGQPENNYKTTPPVL
DSDGSFFLYSKLTVPYDRWVWPDEFSCSVMHEALHNHYTQKSLSLSPG Amino acid sequence of the heavy chain of anti-human LAG-3/FITC mAb[2] FS18-7-33/4420
comprising LALA mutation (SEQ ID NO: 67)
Position of the CDRs are underlined, and the AB, CD, and EF loop sequences are in bold and
underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGQPEDNYKTTPP
VLDSDGSFFLYSKLTVPYDRWVWPDEFSCSVMHEALHNHYTQKSLSLSPG Amino acid sequence of the heavy chain of anti-human LAG-3/FITC mAb[2] FS18-7-33/4420
without LALA mutation (SEQ ID NO: 68)
Position of the CDRs are underlined, and the AB, CD, and EF loop sequences are in bold and
underlined.
EVKLDETGGGLVQPGRPMKLSCVAS<u>GFTFSDYWMN</u>WVRQSPEKGLEWVAQ<u>IRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGQPEDNYKTTPPVL
DSDGSFFLYSKLTVPYDRWVWPDEFSCSVMHEALHNHYTQKSLSLSPG Amino acid sequence of the heavy chain of anti-human LAG-3/FITC mAb[2] FS18-7-36/4420
comprising LALA mutation (SEQ ID NO: 69)
Position of the CDRs are underlined, and the AB, CD, and EF loop sequences are in bold and
underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGQPENNYKTTPP
VLDSDGSYFLYSKLTVPYDRWVWPDEFSCSVMHEALHNHYTQKSLSLSPG Amino acid sequence of the heavy chain of anti-human LAG-3/FITC mAb[2] FS18-7-36/4420
without LALA mutation (SEQ ID NO: 70)
Position of the CDRs are underlined, and the AB, CD, and EF loop sequences are in bold and
underlined.
EVKLDETGGGLVQPGRPMKLSCVAS<u>GFTFSDYWMN</u>WVRQSPEKGLEWVAQ<u>IRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGQPENNYKTTPPVL
DSDGSYFLYSKLTVPYDRWVWPDEFSCSVMHEALHNHYTQKSLSLSPG Amino acid sequence of the heavy chain of anti-human LAG-3/FITC mAb[2] FS18-7-58/4420
comprising LALA mutation (SEQ ID NO: 71)
Position of the CDRs are underlined, and the AB, CD, and EF loop sequences are in bold and
underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGYPEIEFKTTPPV
LDSDGSFFLYSKLTVPYDRWVWPDEFSCSVMHEALHNHYTQKSLSLSPG Amino acid sequence of the heavy chain of anti-human LAG-3/FITC mAb[2] FS18-7-58/4420
without LALA mutation (SEQ ID NO: 72)
Position of the CDRs are underlined, and the AB, CD, and EF loop sequences are in bold and
underlined.
EVKLDETGGGLVQPGRPMKLSCVAS<u>GFTFSDYWMN</u>WVRQSPEKGLEWVAQ<u>IRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGYPEIEFKTTPPVLD
SDGSFFLYSKLTVPYDRWVWPDEFSCSVMHEALHNHYTQKSLSLSPG Amino acid sequence of the heavy chain of anti-human LAG-3/FITC mAb² FS18-7-62/4420 comprising LALA mutation (SEQ ID NO: 73)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNGIPEWNY</u>KTTPP
VLDSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-62/4420 without LALA mutation (SEQ ID NO: 74)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSDIAVEWE<u>SNGIPEWNY</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-65/4420 comprising LALA mutation (SEQ ID NO: 75)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNGYAEYNY</u>KTTPP
VLDSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-65/4420 without LALA mutation (SEQ ID NO: 76)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSDIAVEWE<u>SNGYAEYNY</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-78/4420 comprising LALA mutation (SEQ ID NO: 77)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDIAVEWE<u>SNGYKEENY</u>KTTPP
VLDSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-78/4420 without LALA mutation (SEQ ID NO: 78)
Position of the CDRs are underlined, and the AB, CD, and EF loop sequences are in bold and underlined.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSDIAVEWE<u>SNGYKEENY</u>KTTPPVL
DSDGSFFLYSKLTV<u>PYDRWVWPDE</u>FSCSVMHEALHNHYTQKSLSLSPG Amino acid sequence of the heavy chain of anti-human LAG-3/FITC mAb² FS18-7-88/4420 comprising LALA mutation (SEQ ID NO: 79)
Position of the CDRs are underlined, and the AB, CD, and EF loop sequences are in bold and underlined. Position of LALA mutation is in bold.
EVKLDETGGGLVQPGRPMKLSCVAS<u>GFTFSDYWMN</u>WVRQSPEKGLEWVAQ<u>IRNKPYNYETYY</u>SDS
VKGRFTISRDDSKSSVYLQMNNLRVEDMGIYYC<u>TGSYYGMDY</u>WGQGTSVTVSSASTKGPSVFPLAP

```
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGVPELNVKTTPP
VLDSDGSFFLYSKLTVPYDRWVWPDEFSCSVMHEALHNHYTQKSLSLSPG
```

Amino acid sequence of the heavy chain of anti-human LAG-3/FITC mAb² FS18-7-88/4420 without LALA mutation (SEQ ID NO: 80)
Position of the CDRs are underlined, and the AB, CD, and EF loop sequences are in bold and underlined.
```
EVKLDETGGGLVQPGRPMKLSCVAS<u>GFTFSDYWMN</u>WVRQSPEKGLEWVA<u>QIRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGVPELNVKTTPPVL
DSDGSFFLYSKLTVPYDRWVWPDEFSCSVMHEALHNHYTQKSLSLSPG
```

Amino acid sequence of the heavy chain of anti-human LAG-3/FITC mAb² FS18-7-95/4420 comprising LALA mutation (SEQ ID NO: 81)
Position of the CDRs are underlined, and the AB, CD, and EF loop sequences are in bold and underlined. Position of LALA mutation is in bold.
```
EVKLDETGGGLVQPGRPMKLSCVAS<u>GFTFSDYWMN</u>WVRQSPEKGLEWVA<u>QIRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIAVEWESNGYQEDNYKTTPP
VLDSDGSFFLYSKLTVPYDRWVWPDEFSCSVMHEALHNHYTQKSLSLSPG
```

Amino acid sequence of the heavy chain of anti-human LAG-3/FITC mAb² FS18-7-95/4420 without LALA mutation (SEQ ID NO: 82)
Position of the CDRs are underlined, and the AB, CD, and EF loop sequences are in bold and underlined.
```
EVKLDETGGGLVQPGRPMKLSCVAS<u>GFTFSDYWMN</u>WVRQSPEKGLEWVA<u>QIRNKPYNYETYYSDS
VKGRFTISRDDSKSSVYLQMNNLRVEDMGIYYC</u><u>TGSYYGMDY</u>WGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIAVEWESNGYQEDNYKTTPPVL
DSDGSFFLYSKLTVPYDRWVWPDEFSCSVMHEALHNHYTQKSLSLSPG
```

Amino acid sequence of the heavy chain of anti-FITC mAb 4420 comprising LALA mutation (SEQ ID NO: 83)
Position of the CDRs are underlined. Position of LALA mutation is in bold.
```
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG
```

Amino acid sequence of the heavy chain of anti-FITC mAb 4420 without LALA mutation (SEQ ID NO: 84)
Position of the CDRs are underlined.
```
EVKLDETGGGLVQPGRPMKLSCVASGFTFSDYWMNWVRQSPEKGLEWVAQIRNKPYNYETYYSDS
VKGRFTISRDDSKSSVYLQMNNLRVEDMGIYYCTGSYYGMDYWGQGTSVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG
```

Amino acid sequence of the anti-FITC mAb 4420 light chain (SEQ ID NO: 85)
Position of the CDRs are underlined.
```
DVVMTQTPLSLPVSLGDQASISCRSSQSLVHSNGNTYLRWYLQKPGQSPKVLIYKVSNRFSGVPDRF
SGSGSGTDFTLKISRVEAEDLGVYFCSQSTHVPWTFGGGTKLEIKRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC
```

Amino acid sequences of the CDRs of anti-PD-L1 antibody 84G09 (according to IMGT)
HCDR1 GFTFDDYA (SEQ ID NO: 86)
HCDR2 ISWKSNII (SEQ ID NO: 87)
HCDR3 ARDITGSGSYGWFDP (SEQ ID NO: 88)
LCDR1 QSISSY (SEQ ID NO: 89)
LCDR2 VAS (SEQ ID NO: 90)
LCDR3 QQSYSNPIT (SEQ ID NO: 91)

Amino acid sequences of the CDRs of anti-PD-L1 antibody 84G09 (according to Kabat)
HCDR1 DYAMH (SEQ ID NO: 136)
HCDR2 GISWKSNIIGYADSVKG (SEQ ID NO: 137)
HCDR3 DITGSGSYGWFDP (SEQ ID NO: 138)
LCDR1 RASQSISSYLN (SEQ ID NO: 139)
LCDR2 VASSLQS (SEQ ID NO: 140)
LCDR3 QQSYSNPIT (SEQ ID NO: 141)

Amino acid sequence of the anti-PD-L1 antibody 84G09 VH domain (SEQ ID NO: 92)
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTVSS Amino acid sequence of the anti-PD-L1 antibody 84G09 VL domain (SEQ ID NO: 93)
DIQMTQSPSSLSASVGDRVTITCRASQSISSYLNWYQQKPGKAPKPLIYVASSLQSGVPSSFSGSGS
GTDFTLTISSLQPEDFATYYCQQSYSNPITFGQGTRLEIK Amino acid sequence of the anti-human LAG-3/PD-L1 mAb² FS18-7-9/84G09 with LALA mutation
heavy chain (SEQ ID NO: 94)
Position of the CDRs are underlined, and the AB, CD, and EF loop sequences are in bold and
underlined. Position of LALA mutation is in bold.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSWDEPWGEDVSLTCLVKGFYPSDIAVEWESNGQPENNYKTT
PPVLDSDGSFFLYSKLTVPYDRWVWPDEFSCSVMHEALHNHYTQKSLSLSPG Amino acid sequence of the anti-human LAG-3/PD-L1 mAb² FS18-7-9/84G09 heavy chain
(SEQ ID NO: 95)
Position of the CDRs are underlined, and the AB, CD, and EF loop sequences are in bold and
underlined.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPSWDEPWGEDVSLTCLVKGFYPSDIAVEWESNGQPENNYKTTP
PVLDSDGSFFLYSKLTVPYDRWVWPDEFSCSVMHEALHNHYTQKSLSLSPG Amino acid sequence of the anti-human LAG-3/PD-L1 mAb² FS18-7-32/84G09 with LALA mutation
heavy chain (SEQ ID NO: 96)
Position of the CDRs are underlined, and the AB, CD, and EF loop sequences are in bold and
underlined. Position of LALA mutation is in bold.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSWDEPWGEDVSLTCLVKGFYPSEIAVEWESNGQPENNYKTT
PPVLDSDGSFFLYSKLTVPYDRWVWPDEFSCSVMHEALHNHYTQKSLSLSPG Amino acid sequence of the anti-human LAG-3/PD-L1 mAb² FS18-7-32/84G09 heavy chain
(SEQ ID NO: 97)
Position of the CDRs are underlined, and the AB, CD, and EF loop sequences are in bold and
underlined.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPSWDEPWGEDVSLTCLVKGFYPSEIAVEWESNGQPENNYKTTP
PVLDSDGSFFLYSKLTVPYDRWVWPDEFSCSVMHEALHNHYTQKSLSLSPG Amino acid sequence of the anti-human LAG-3/PD-L1 mAb² FS18-7-33/84G09 with LALA mutation
heavy chain (SEQ ID NO: 98)
Position of the CDRs are underlined, and the AB, CD, and EF loop sequences are in bold and
underlined. Position of LALA mutation is in bold.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSWDEPWGEDVSLTCLVKGFYPSDIAVEWESNGQPEDNYKTT
PPVLDSDGSFFLYSKLTVPYDRWVWPDEFSCSVMHEALHNHYTQKSLSLSPG Amino acid sequence of the anti-human LAG-3/PD-L1 mAb² FS18-7-33/84G09 heavy chain
(SEQ ID NO: 99)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGQPEDNY</u>KTTP
PVLDSDGSFFLYSKLTV<u>PYDRWVWPDE</u>FSCSVMHEALHNHYTQKSLSLSPG Amino acid sequence of the anti-human LAG-3/PD-L1 mAb² FS18-7-36/84G09 with LALA mutation
heavy chain (SEQ ID NO: 100)
Position of the CDRs are underlined, and the AB, CD, and EF loop sequences are in bold and
underlined. Position of LALA mutation is in bold.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPS<u>WDEPWGED</u>VSLTCLVKGFYPSDIAVEWE<u>SNGQPENNY</u>KTT
PPVLDSDGSYFLYSKLTV<u>PYDRWVWPDE</u>FSCSVMHEALHNHYTQKSLSLSPG Amino acid sequence of the anti-human LAG-3/PD-L1 mAb² FS18-7-36/84G09 heavy chain
(SEQ ID NO: 101)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGQPENNY</u>KTTP
PVLDSDGSYFLYSKLTV<u>PYDRWVWPDE</u>FSCSVMHEALHNHYTQKSLSLSPG Amino acid sequence of the anti-human LAG-3/PD-L1 mAb² FS18-7-58/84G09 with LALA mutation
heavy chain (SEQ ID NO: 102)
Position of the CDRs are underlined, and the AB, CD, and EF loop sequences are in bold and
underlined. Position of LALA mutation is in bold.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPS<u>WDEPWGED</u>VSLTCLVKGFYPSDIAVEWE<u>SNGYPEIEF</u>KTTP
PVLDSDGSFFLYSKLTV<u>PYDRWVWPDE</u>FSCSVMHEALHNHYTQKSLSLSPG Amino acid sequence of the anti-human LAG-3/PD-L1 mAb² FS18-7-58/84G09 heavy chain
(SEQ ID NO: 103)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGYPEIEF</u>KTTPP
VLDSDGSFFLYSKLTV<u>PYDRWVWPDE</u>FSCSVMHEALHNHYTQKSLSLSPG Amino acid sequence of the anti-human LAG-3/PD-L1 mAb² FS18-7-62/84G09 with LALA mutation
heavy chain (SEQ ID NO: 104)
Position of the CDRs are underlined, and the AB, CD, and EF loop sequences are in bold and
underlined. Position of LALA mutation is in bold.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPS<u>WDEPWGED</u>VSLTCLVKGFYPSDIAVEWE<u>SNGIPEWNY</u>KTT
PPVLDSDGSFFLYSKLTV<u>PYDRWVWPDE</u>FSCSVMHEALHNHYTQKSLSLSPG Amino acid sequence of the anti-human LAG-3/PD-L1 mAb² FS18-7-62/84G09 heavy chain
(SEQ ID NO: 105)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGIPEWNY</u>KTTP
PVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-65/84G09 with LALA mutation
heavy chain (SEQ ID NO: 106)
Position of the CDRs are underlined, and the AB, CD, and EF loop sequences are in bold and
underlined. Position of LALA mutation is in bold.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPS<u>WDEPWGED</u>VSLTCLVKGFYPSDIAVEWE<u>SNGYAEYNY</u>KTT
PPVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-65/84G09 heavy chain
(SEQ ID NO: 107)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGYAEYNY</u>KTTP
PVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-78/84G09 with LALA mutation
heavy chain (SEQ ID NO: 108)
Position of the CDRs are underlined, and the AB, CD, and EF loop sequences are in bold and
underlined. Position of LALA mutation is in bold.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPS<u>WDEPWGED</u>VSLTCLVKGFYPSDIAVEWE<u>SNGYKEENY</u>KTT
PPVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-78/84G09 heavy chain
(SEQ ID NO: 109)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGYKEENY</u>KTTP
PVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-88/84G09 with LALA mutation
heavy chain (SEQ ID NO: 110)
Position of the CDRs are underlined, and the AB, CD, and EF loop sequences are in bold and
underlined. Position of LALA mutation is in bold.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPS<u>WDEPWGED</u>VSLTCLVKGFYPSDIAVEWE<u>SNGVPELNV</u>KTT
PPVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-88/84G09 heavy chain
(SEQ ID NO: 111)
Position of the CDRs are underlined, and the AB, CD, and EF loop sequences are in bold and
underlined.
EVQLVESGGGLVQPGRSLRLSCAAS<u>GFTFDDYAMH</u>WVRQTPGKGLEWVSG<u>ISWKSNII</u>GYADSVKG
RFTISRDNAKNSLYLQMNSLRAEDTALYYC<u>ARDITGSGSYGWFDP</u>WGQGTLVTVSSASTKGPSVFPL
APSSKSTSGGTAALGCLVKDYFPEPVTVSWNSGALTSGVHTFPAVLQSSGLYSLSSVVTVPSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPS<u>WDEPWGED</u>VSLTCLVKGFYPSDIAVEWE<u>SNGVPELNV</u>KTTP
PVLDSDGSFFLYSKLTV_<u>PYDRWVWPDE</u>_FSCSVMHEALHNHYTQKSLSLSPG Amino acid sequence of the anti-human LAG-3/PD-L1 mAb² FS18-7-95/84G09 with LALA mutation
heavy chain (SEQ ID NO: 112)
Position of the CDRs are underlined, and the AB, CD, and EF loop sequences are in bold and
underlined. Position of LALA mutation is in bold.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSWDEPWGEDVSLTCLVKGFYPSDIAVEWESNGYQEDNYKTT
PPVLDSDGSFFLYSKLTVPYDRWVWPDEFSCSVMHEALHNHYTQKSLSLSPG Amino acid sequence of the anti-human LAG-3/PD-L1 mAb² FS18-7-95/84G09 heavy chain
(SEQ ID NO: 113)
Position of the CDRs are underlined, and the AB, CD, and EF loop sequences are in bold and
underlined. Position of LALA mutation is in bold.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPSWDEPWGEDVSLTCLVKGFYPSDIAVEWESNGYQEDNYKTTP
PVLDSDGSFFLYSKLTVPYDRWVWPDEFSCSVMHEALHNHYTQKSLSLSPG Amino acid sequence of the anti-human PD-L1 mAb 84G09 with LALA heavy chain (SEQ ID NO: 114)
Position of the CDRs are underlined. Position of LALA mutation is in bold.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG Amino acid sequence of the anti-human PD-L1 mAb 84G09 heavy chain (SEQ ID NO: 115)
Position of the CDRs are underlined.
EVQLVESGGGLVQPGRSLRLSCAASGFTFDDYAMHWVRQTPGKGLEWVSGISWKSNIIGYADSVKG
RFTISRDNAKNSLYLQMNSLRAEDTALYYCARDITGSGSYGWFDPWGQGTLVTSSASTKGPSVFPL
APSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG Amino acid sequence of the anti-human PD-L1 mAb 84G09 light chain (SEQ ID NO: 116)
Position of the CDRs are underlined.
DIQMTQSPSSLSASVGDRVTITCRASQSISSYLNWYQQKPGKAPKPLIYVASSLQSGVPSSFSGSGS
GTDFTLTISSLQPEDFATYYCQQSYSNPITFGQGTRLEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Amino acid sequence of the anti-mouse LAG-3/PD-L1 mAb² FS18-7-108-29/S1 with LALA mutation
heavy chain (SEQ ID NO: 117)
Position of the CDRs are underlined, and the AB, CD, and EF loop sequences are in bold and
underlined. Position of LALA mutation is in bold.
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSWDEPWGEDVSLTCLVKGFYPSDIVVEWESNGQPENNYKTTPP
VLDSDGSFFLYSKLTVPFERWMWPDEFSCSVMHEALHNHYTQKSLSLSPG Amino acid sequence of the anti-mouse LAG-3/PD-L1 mAb² FS18-7-108-29/S1 heavy chain
(SEQ ID NO: 118)
Position of the CDRs are underlined, and the AB, CD, and EF loop sequences are in bold and
underlined.
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSWDEPWGEDVSLTCLVKGFYPSDIVVEWESNGQPENNYKTTPPVL
DSDGSFFLYSKLTVPFERWMWPDEFSCSVMHEALHNHYTQKSLSLSPG -continued Amino acid sequence of the anti-mouse PD-L1 mAb S1 light chain (SEQ ID NO: 119)
Position of the CDRs are underlined.
DIQMTQSPSSLSASVGDRVTITCRAS<u>QDVSTA</u>VAWYQQKPGKAPKLLIY<u>SAS</u>FLYSGVPSRFSGSGS
GTDFTLTISSLQPEDFATYYC<u>QQYLFTPPT</u>FGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Amino acid sequence of the anti-mouse LAG-3/PD-L1 mAb² FS18-7-108-35/S1 with LALA mutation
heavy chain (SEQ ID NO: 120)
Position of the CDRs are underlined, and the AB, CD, and EF loop sequences are in bold and
underlined. Position of LALA mutation is in bold.
EVQLVESGGGLVQPGGSLRLSCAAS<u>GFTFSDSW</u>IHWVRQAPGKGLEWVAW<u>ISPYGGST</u>YYADSVK
GRFTISADTSKNTAYLQMNSLRAEDTAVYYC<u>ARRHWPGGFDY</u>WGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPS<u>WDEPWGED</u>VSLTCLVKGFYPSDISVEWE<u>SNGQPENNY</u>KTTPP
VLDSDGSFFLYSKLTV<u>PFERWMWPDE</u>FSCSVMHEALHNHYTQKSLSLSPG Amino acid sequence of the anti-mouse LAG-3/PD-L1 mAb² FS18-7-108-35/S1 heavy chain
(SEQ ID NO: 121)
Position of the CDRs are underlined, and the AB, CD, and EF loop sequences are in bold and
underlined.
EVQLVESGGGLVQPGGSLRLSCAAS<u>GFTFSDSW</u>IHWVRQAPGKGLEWVAW<u>ISPYGGST</u>YYADSVK
GRFTISADTSKNTAYLQMNSLRAEDTAVYYC<u>ARRHWPGGFDY</u>WGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPS<u>WDEPWGED</u>VSLTCLVKGFYPSDISVEWE<u>SNGQPENNY</u>KTTPPVL
DSDGSFFLYSKLTV<u>PFERWMWPDE</u>FSCSVMHEALHNHYTQKSLSLSPG Amino acid sequence of the control PD-L1 mAb S1 with LALA mutation heavy chain (SEQ ID NO: 122)
Position of the CDRs are underlined. Position of LALA mutation is in bold.
EVQLVESGGGLVQPGGSLRLSCAAS<u>GFTFSDSW</u>IHWVRQAPGKGLEWVAW<u>ISPYGGST</u>YYADSVK
GRFTISADTSKNTAYLQMNSLRAEDTAVYYC<u>ARRHWPGGFDY</u>WGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequence of the control PD-L1 mAb S1 heavy chain (SEQ ID NO: 123)
Position of the CDRs are underlined. Position of LALA mutation is in bold.
EVQLVESGGGLVQPGGSLRLSCAAS<u>GFTFSDSW</u>IHWVRQAPGKGLEWVAW<u>ISPYGGST</u>YYADSVK
GRFTISADTSKNTAYLQMNSLRAEDTAVYYC<u>ARRHWPGGFDY</u>WGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the control anti-human LAG-3 mAb 25F7 heavy chain (SEQ ID NO: 124)
Position of the CDRs are underlined.
QVQLQQWGAGLLKPSETLSLTCAVY<u>GGSFSDYY</u>WNWIRQPPGKGLEWIG<u>EINHRGST</u>NSNPSLKSR
VTLSLDTSKNQFSLKLRSVTAADTAVYYC<u>AFGYSDYEYN</u>WFDPWGQGTLVTVSSASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of the control anti-human LAG-3 mAb 25F7 light chain (SEQ ID NO: 125)
Position of the CDRs are underlined.
EIVLTQSPATLSLSPGERATLSCRAS<u>QSISSY</u>LAWYQQKPGQAPRLLIY<u>DAS</u>NRATGIPARFSGSGSG
TDFTLTISSLEPEDFAVYYC<u>QQRSNWPLT</u>FGQGTNLEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSS
PVTKSFNRGEC Amino acid sequence of human LAG-3 (SEQ ID NO: 126)
MWEAQFLGLLFLQPLWVAPVKPLQPGAEVPVVWAQEGAPAQLPCSPTIPLQDLSLLRRAGVTWQHQ
PDSGPPAAAPGHPLAPGPHPAAPSSWGPRPRRYTVLSVGPGGLRSGRLPLQPRVQLDERGRQRGD
FSLWLRPARRADAGEYRAAVHLRDRALSCRLRLRLGQASMTASPPGSLRASDWVILNCSFSRPDRP
ASVHWFRNRGQGRVPVRESPHHHLAESFLFLPQVSPMDSGPWGCILTYRDGFNVSIMYNLTVLGLE
PPTPLTVYAGAGSRVGLPCRLPAGVGTRSFLTAKWTPPGGGPDLLVTGDNGDFTLRLEDVSQAQAG
TYTCHIHLQEQQLNATVTLAIITVTPKSFGSPGSLGKLLCEVTPVSGQERFVWSSLDTPSQRSFSGPW
LEAQEAQLLSQPWQCQLYQGERLLGAAVYFTELSSPGAQRSGRAPGALPAGHLLLFLILGVLSLLLLV
TGAFGFHLWRRQWRPRRFSALEQGIHPPQAQSKIEELEQEPEPEPEPEPEPEPEPEPEPEQL Amino acid sequence of mouse LAG-3 (SEQ ID NO: 127)
MREDLLLGFLLLGLLWEAPVVSSGPGKELPVVWAQEGAPVHLPCSLKSPNLDPNFLRRGGVIWQHQ
PDSGQPTPIPALDLHQGMPSPRQPAPGRYTVLSVAPGGLRSGRQPLHPHVQLEERGLQRGDFSLWL
RPALRTDAGEYHATVRLPNRALSCSLRLRVGQASMIASPSGVLKLSDWVLLNCSFSRPDRPVSVHW
FQGQNRVPVYNSPRHFLAETFLLLPQVSPLDSGTWGCVLTYRDGFNVSITYNLKVLGLEPVAPLTVYA
AEGSRVELPCHLPPGVGTPSLLIAKWTPGGGPELPVAGKSGNFTLHLEAVGLAQAGTYTCSIHLQG
QQLNATVTLAVITVTPKSFGLPGSRGKLLCEVTPASGKERFVWRPLNNLSRSCPGPVLEIQEARLLAE
RWQCQLYEGQRLLGATVYAAESSSGAHSARRISGDLKGGHLVLVLILGALSLFLLVAGAFGFHVWVRK
QLLLRRFSALEHGIQPFPAQRKIEELERELETEMGQEPEPEPEPQLEPEPRQL Amino acid sequence of cynomolgus LAG-3 (SEQ ID NO: 128)
MWEAQFLGLLFLQPLWVAPVKPPQPGAEISVVWAQEGAPAQLPCSPTIPLQDLSLLRRAGVTWQHQ
PDSGPPAAAPGHPPVPGHRPAAPYSWGPRPRRYTVLSVGPGGLRSGRLPLQPRVQLDERGRQRG
DFSLWLRPARRADAGEYRATVHLRDRALSCRLRLRVGQASMTASPPGSLRTSDWVILNCSFSRPDR
PASVHWFRSRGQGRVPVQGSPHHHLAESFLFLPHVGPMDSGLWGCILTYRDGFNVSIMYNLTVLGL
EPATPLTVYAGAGSRVELPCRLPPAVGTQSFLTAKWAPPGGGPDLLVAGDNGDFTLRLEDVSQAQA
GTYICHIRLQGQQLNATVTLAIITVTPKSFGSPGSLGKLLCEVTPASGQEHFVWSPLNTPSQRSFSGP
WLEAQEAQLLSQPWQCQLHQGERLLGAAVYFTELSSPGAQRSGRAPGALRAGHLPLFLILGVLFLLL
LVTGAFGFHLWRRQWRPRRFSALEQGIHPPQAQSKIEELEQEPELEPEPELERELGPEPEPGPEPEP
EQL Amino acid sequence of human PD-L1 (SEQ ID NO: 129)
MRIFAVFIFMTYWHLLNAFTVTVPKDLYVVEYGSNMTIECKFPVEKQLDLAALIVYWEMEDKNIIQFV
HGEEDLKVQHSSYRQRARLLKDQLSLGNAALQITDVKLQDAGVYRCMISYGGADYKRITVKVNAPY
NKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERTHLVILGAILLCLGVALTFIFRLRKGRMMDVKK
CGIQDTNSKKQSDTHLEET Amino acid sequence of murine PD-L1 (SEQ ID NO: 130)
MRIFAGIIFTACCHLLRAFTITAPKDLYVVEYGSNVTMECRFPVERELDLLALVVYWEKEDEQVIQFV
AGEEDLKPQHSNFRGRASLPKDQLLKGNAALQITDVKLQDAGVYCCIISYGGADYKRITLKVNAPYR
KINQRISVDPATSEHELICQAEGYPEAEVIWTNSDHQPVSGKRSVTTSRTEGMLLNVTSSLRVNATA
NDVFYCTFWRSQPGQNHTAELIIPELPATHPPQNRTHWVLLGSILLFLIVVSTVLLFLRKQVRMLDVE
KCGVEDTSSKNRNDTQFEET Amino acid sequence of cynomolgus PD-L1 (SEQ ID NO: 131)
MRIFAVFIFTIYWHLLNAFTVTVPKDLYVVEYGSNMTIECKFPVEKQLDLTSLIVYWEMEDKNIIQFVH
GEEDLKVQHSNYRQRAQLLKDQLSLGNAALRITDVKLQDAGVYRCMISYGGADYKRITVKVNAPYN
KINQRILVVDPVTSEHELTCQAEGYPKAEVIWTSSSDHQVLSGKTTTTNSKREEKLLNVTSTLRINTTA
NEIFYCIFRRLDPEENHTAELVIPELPLALPPNERTHLVILGAIFLLLGVALTFIFYLRKGRMMDMKKCG
IRVTNSKKQRDTQLEET Amino acid sequence of the heavy chain of anti-mouse LAG-3/FITC mAb[2] FS18-7-108-
29/4420 comprising LALA mutation (SEQ ID NO: 132)
Position of the CDRs are underlined, and the AB, CD, and EF loop sequences are in bold and
underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSD
SVKGRFTISRDDSKSSVYLQMNNLRVEDMGIYYC<u>TGSYYGMDY</u>WGQGTSVTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVS
NKALPAPIEKTISKAKGQPREPQVYTLPPS<u>WDEPWGED</u>VSLTCLVKGFYPSDIVVEWE**<u>SNGQPENN
Y</u>KTTPPVLDSDGSFFLYSKLTV<u>PFERWMWPDE</u>**FSCSVMHEALHNHYTQKSLSLSPG Amino acid sequence of the heavy chain of anti-mouse LAG-3/FITC mAb[2] FS18-7-108-
35/4420 comprising LALA mutation (SEQ ID NO: 133)
Position of the CDRs are underlined, and the AB, CD, and EF loop sequences are in bold and
underlined. Position of LALA mutation is in bold.
EVKLDETGGGLVQPGRPMKLSCVAS<u>GFTFSDYWMN</u>WVRQSPEKGLEWVAQ<u>IRNKPYNYETYYSD
SVKGRFTISRDDSKSSVYLQMNNLRVEDMGIYYC<u>TGSYYGMDY</u>WGQGTSVTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLHQDWLNGKEYKCKVS
NKALPAPIEKTISKAKGQPREPQVYTLPPS<u>WDEPWGED</u>VSLTCLVKGFYPSDISVEWE**<u>SNGQPENN
Y</u>KTTPPVLDSDGSFFLYSKLTV<u>PFERWMWPDE</u>**FSCSVMHEALHNHYTQKSLSLSPG Amino acid sequence of the heavy chain of anti-mouse LAG-3/FITC mAb[2] FS18-7-108-
29/4420 (SEQ ID NO: 134)
Position of the CDRs are underlined, and the AB, CD, and EF loop sequences are in bold and
underlined.
EVKLDETGGGLVQPGRPMKLSCVAS<u>GFTFSDYWMN</u>WVRQSPEKGLEWVAQ<u>IRNKPYNYETYYSD
SVKGRFTISRDDSKSSVYLQMNNLRVEDMGIYYC<u>TGSYYGMDY</u>WGQGTSVTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSN
KALPAPIEKTISKAKGQPREPQVYTLPPS<u>WDEPWGED</u>VSLTCLVKGFYPSDIVVEWE<u>SNGQPENNY</u>
KTTPPVLDSDGSFFLYSKLTV<u>PFERWMWPDE</u>FSCSVMHEALHNHYTQKSLSLSPG

REFERENCES

All documents mentioned in this specification are incorporated herein by reference in their entirety.

Bae J, Lee S J, Park C G, Lee Y S, Chun T. Trafficking of LAG-3 to the surface on activated T cells via its cytoplasmic domain and protein kinase C signaling. J Immunol. 193(6), 3101-12 (2014).

Baecher-Allan C, Wolf E, Hafler D A. MHC class II expression identifies functionally distinct human regulatory T cells. J Immunol. 176(8), 4622-31 (2006).

Camisaschi C, Casati C, Rini F, Perego M, De Filippo A, Triebel F, Parmiani G, Belli F, Rivoltini L, Castelli C. LAG-3 expression defines a subset of CD4(+)CD25(high) Foxp3(+) regulatory T cells that are expanded at tumor sites. J Immunol. 184(11), 6545-51 (2010).

Curran M A, Montalvo W, Yagita H, Allison J P. PD-1 and CTLA-4 combination blockade expands infiltrating T cells and reduces regulatory T and myeloid cells within B16 melanoma tumors. Proc Natl Acad Sci USA. 107(9), 4275-80 (2010).

Demeure, C. E., Wolfers, J., Martin-Garcia, N., Gaulard, P. & Triebel, F. T Lymphocytes infiltrating various tumour types express the MHC class II ligand lymphocyte activation gene-3 (LAG-3): role of LAG-3/MHC class II interactions in cell-cell contacts. European journal of cancer 37, 1709-1718 (2001).

Durham N M, Nirschl C J, Jackson C M, Elias J, Kochel C M, Anders R A, Drake C G. Lymphocyte Activation Gene 3 (LAG-3) modulates the ability of CD4 T cells to be suppressed in vivo. PLoS One. 9(11), e109080 (2015).

Engels B, Engelhard V H, Sidney J, Sette A, Binder D C, Liu R B, Kranz D M, Meredith S C, Rowley D A, Schreiber H. Relapse or eradication of cancer is predicted by peptide-major histocompatibility complex affinity. Cancer Cell. 23(4), 516-26 (2013).

Gandhi M K, Lambley E, Duraiswamy J, Dua U, Smith C, Elliott S, Gill D, Marlton P, Seymour J, Khanna R. Expression of LAG-3 by tumor-infiltrating lymphocytes is coincident with the suppression of latent membrane antigen-specific CD8+ T cell function in Hodgkin lymphoma patients. Blood 108(7), 2280-9 (2006).

Grosso J, Inzunza D, Wu Q, et al. Programmed death-ligand 1 (PD-L1) expression in various tumor types. Journal for Immunotherapy of Cancer. 1(Suppl 1):P53. (2013).

Herbst R S, Soria J C, Kowanetz M, Fine G D, Hamid O, Gordon M S, Sosman J A, McDermott D F, Powderly J D, Gettinger S N, Kohrt H E, Horn L, Lawrence D P, Rost S, Leabman M, Xiao Y, Mokatrin A, Koeppen H, Hegde P S, Mellman I, Chen D S, Hodi F S. Predictive correlates of response to the anti-PD-L1 antibody MPDL3280A in cancer patients. Nature 515(7528), 563-7 (2014).

Huard B, Mastrangeli R, Prigent P, et al. Characterization of the major histocompatibility complex class II binding site on LAG-3 protein. Proc Natl Acad Sci USA 94, 5744-9 (1997).

Iwai Y, Ishida M, Tanaka Y, Okazaki T, Honjo T, Minato N. Involvement of PD-L1 on tumor cells in the escape from host immune system and tumor immunotherapy by PD-L1 blockade. Proc Natl Acad Sci USA. 99(19), 12293-7.

Jing W, Gershan J A, Weber J, Tlomak D, McOlash L, Sabatos-Peyton C, Johnson BD1. Combined immune checkpoint protein blockade and low dose whole body irradiation as immunotherapy for myeloma. J Immunother Cancer. 3(1):2 (2015).

Kabat, E. A. et al., In: Sequences of Proteins of Immunological Interest. NIH Publication, 91-3242 (1991).

Larkin J, Hodi F S, Wolchok J D. Combined Nivolumab and Ipilimumab or Monotherapy in Untreated Melanoma. N Engl J Med. 373(13), 1270-1 (2015).

Huard B, Mastrangeli R, Prigent P, et al. Characterization of the major histocompatibility complex class II binding site on LAG-3 protein. Proc Natl Acad Sci USA 94, 5744-9 (1997).

Powles T, Eder J P, Fine G D, Braiteh F S, Loriot Y, Cruz C, Bellmunt J, Burris H A, Petrylak D P, Teng S L, Shen X, Boyd Z, Hegde P S, Chen D S, Vogelzang N J. MPDL3280A (anti-PD-L1) treatment leads to clinical activity in metastatic bladder cancer. Nature. 515(7528), 558-62 (2014).

Sega E I, Leveson-Gower D B, Florek M, Schneidawind D, Luong R H, Negrin R S. Role of lymphocyte activation gene-3 (Lag-3) in conventional and regulatory T cell function in allogeneic transplantation. PLoS One. 9(1), e86551 (2014).

Wolchok J et al; Nivolumab plus ipilimumab in advanced melanoma. N Engl J Med. 369(2), 122-33 (2013).

Woo S R, Turnis M E, Goldberg M V, Bankoti J, Selby M, Nirschl C J, Bettini M L, Gravano D M, Vogel P, Liu C L, Tangsombatvisit S, Grosso J F, Netto G, Smeltzer M P, Chaux A, Utz P J, Workman C J, Pardoll D M, Korman A J, Drake C G, Vignali D A. Immune inhibitory molecules LAG-3 and PD-1 synergistically regulate T cell function to promote tumoral immune escape. Cancer Res. 72(4), 917-2 (2012).

Workman C J, Vignali D A. Negative regulation of T cell homeostasis by lymphocyte activation gene-3 (CD223). J Immunol. 2005 Jan. 15; 174(2):688-95.

Workman C J, Vignali D A. The CD4-related molecule, LAG-3 (CD223), regulates the expansion of activated T cells. Eur J Immunol. 2003 April; 33(4):970-9.

---

The invention claimed is:

1. An antibody molecule which binds to programmed death-ligand 1 (PD-L1) and lymphocyte-activation gene 3 (LAG-3), wherein the antibody molecule comprises:
   (i) a CDR-based antigen binding site for PD-L1; and
   (ii) a LAG-3 antigen binding site located in a CH3 domain of the antibody molecule, wherein the LAG-3 binding site comprises the amino acid sequences WDEPWGED (SEQ ID NO: 1) and PYDRWVWPDE (SEQ ID NO: 3), and wherein the amino acid sequence WDEPWGED is located in a first structural loop of the CH3 domain and the amino acid sequence PYDRWVWPDE is located in a second structural loop of the CH3 domain.

2. An antibody molecule according to claim 1, wherein the LAG-3 antigen binding site comprises the amino acid sequence set forth in SEQ ID NO: 1 in the AB loop, and the amino acid sequence set forth in SEQ ID NO: 3 in the EF loop of the CH3 domain.

3. An antibody molecule according to claim 1, wherein the LAG-3 antigen binding site further comprises one of the following sequences:

(i)
   SNGQPENNY;                    (SEQ ID NOS 2, 8 and 18)

(ii)
   SNGQPEDNY;                    (SEQ ID NO: 13)

(iii)
   SNGYPEIEF;                    (SEQ ID NO: 23)

(iv)
   SNGIPEWNY;                    (SEQ ID NO: 28)

(v)
   SNGYAEYNY;                    (SEQ ID NO: 33)

(vi)
   SNGYKEENY;                    (SEQ ID NO: 38)

(vii)
   SNGVPELNV;                    (SEQ ID NO: 43)
   or (viii)
   SNGYQEDNY.                    (SEQ ID NO: 48)

4. An antibody molecule according to claim 3, wherein the LAG-3 antigen binding site comprises the amino acid sequence set forth in SEQ ID NO: 2, 8, 13, 18, 23, 28, 33, 38, 43, or 48 in the CD loop of the CH3 domain.

5. An antibody molecule according to claim 1, wherein the antibody molecule is an immunoglobulin G molecule.

6. An antibody molecule according to claim 1, wherein the antibody molecule comprises the CH3 domain set forth in SEQ ID NO: 5, 10, 15, 20, 25, 30, 35, 40, 45, or 50.

7. An antibody molecule according to claim 1, wherein the antibody molecule comprises the sequence set forth in SEQ ID NO: 6, 7, 11, 12, 16, 17, 21, 22, 26, 27, 31, 32, 36, 37, 41, 42, 46, 47, 51, or 52.

8. An antibody molecule according to claim 1, comprising the complementarity determining regions (CDRs) set forth in SEQ ID NOs: 86 to 91.

9. An antibody molecule according to claim 8, wherein the antibody molecule comprises the VH and/or VL domains set forth in SEQ ID NOs: 92 and 93.

10. An antibody molecule according to claim 8, wherein the antibody molecule comprises the heavy chain sequence set forth in any one of SEQ ID NOs: 94 to 113.

11. An antibody molecule according to claim 8, wherein the antibody molecule comprises the light chain sequence set forth in SEQ ID NO: 116.

12. An antibody molecule according to claim 1, wherein the antibody molecule is conjugated to an immune system modulator, cytotoxic molecule, radioisotope, or detectable label.

13. A nucleic acid encoding an antibody molecule according to claim 1.

14. A vector comprising the nucleic acid of claim 13.

15. A recombinant host cell comprising the nucleic acid of claim 13.

16. A method of producing an antibody molecule, comprising culturing the recombinant host cell of claim 15 under conditions for production of the antibody molecule.

17. A pharmaceutical composition comprising an antibody molecule according to claim 1 and a pharmaceutically acceptable excipient.

18. A method of treating cancer in a patient, wherein the method comprises administering to the patient a therapeutically effective amount of an antibody molecule according to claim 1.

19. A method according to claim 18, wherein the cancer is selected from the group consisting of: Hodgkin's lymphoma, non-Hodgkin's lymphoma, ovarian cancer, prostate cancer, colorectal cancer, fibrosarcoma, renal cell carcinoma, melanoma, pancreatic cancer, breast cancer, glioblastoma multiforme, lung cancer, head and neck cancer, stomach cancer, bladder cancer, cervical cancer, uterine cancer, vulvar cancer, testicular cancer, penile cancer, leukemia, multiple myeloma, squamous cell cancer, testicular cancer, esophageal cancer, Kaposi's sarcoma, and central nervous system (CNS) lymphoma, hepatocellular carcinoma, Merkel cell carcinoma, nasopharyngeal cancer, and mesothelioma.

20. An antibody molecule according to claim 10, wherein the antibody molecule comprises the heavy chain sequence set forth in SEQ ID NO: 94 and the light chain sequence set forth in SEQ ID NO: 116.

\* \* \* \* \*

UNITED STATES PATENT AND TRADEMARK OFFICE
CERTIFICATE OF CORRECTION

| | |
|---|---|
| PATENT NO. | : 11,214,620 B2 |
| APPLICATION NO. | : 16/311604 |
| DATED | : January 4, 2022 |
| INVENTOR(S) | : Campbell et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 477 days.

Signed and Sealed this
Eleventh Day of February, 2025

Coke Morgan Stewart
*Acting Director of the United States Patent and Trademark Office*

SEQUENCE LISTING

```
<160> NUMBER OF SEQ ID NOS: 142

<210> SEQ ID NO 1
<211> LENGTH: 8
<212> TYPE: PRT
<213> ORGANISM: Artificial Sequence
<220> FEATURE:
<223> OTHER INFORMATION: FS18-7-9 AB loop

<400> SEQUENCE: 1

Trp Asp Glu Pro Trp Gly Glu Asp
1               5
```

<210> SEQ ID NO 2
<211> LENGTH: 9
<212> TYPE: PRT
<213> ORGANISM: Artificial Sequence
<220> FEATURE:
<223> OTHER INFORMATION: FS18-7-9 CD loop

<400> SEQUENCE: 2

Ser Asn Gly Gln Pro Glu Asn Asn Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: FS18-7-9 EF loop

<400> SEQUENCE: 3

Pro Tyr Asp Arg Trp Val Trp Pro Asp Glu
1               5                   10

<210> SEQ ID NO 4
<211> LENGTH: 318
<212> TYPE: DNA
<213> ORGANISM: Artificial Sequence
<220> FEATURE:
<223> OTHER INFORMATION: Nucleotide sequence of Fcab FS18-7-9 CH3 domain

<400> SEQUENCE: 4
ggccagcctc gagaaccaca ggtgtacacc ctgcccccat cctgggatga gccgtggggt      60
gaagacgtca gcctgacctg cctggtcaaa ggcttctatc ccagcgaaat cgccgtggag     120
tgggagagca atgggcagcc ggagaacaac tacaagacca cgcctcccgt gctggactcc     180
gacggctcct tcttcctcta cagcaagctc accgtgccgt atgataggtg ggtttggccg     240
gatgagttct catgctccgt gatgcatgag gctctgcaca accactacac acagaagagc     300 ctctcccctgt ctccgggt                                                   318

<210> SEQ ID NO 5
<211> LENGTH: 106
<212> TYPE: PRT
<213> ORGANISM: Artificial Sequence
<220> FEATURE:
<223> OTHER INFORMATION: Amino acid sequence of Fcab FS18-7-9 CH3 domain

<400> SEQUENCE: 5

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 6
<211> LENGTH: 216
<212> TYPE: PRT
<213> ORGANISM: Artificial Sequence
<220> FEATURE:
<223> OTHER INFORMATION: Amino acid sequence of Fcab FS18-7-9 CH2 and
      CH3 domains, comprising LALA mutation

<400> SEQUENCE: 6

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 7
<211> LENGTH: 216
<212> TYPE: PRT
<213> ORGANISM: Artificial Sequence
<220> FEATURE:
<223> OTHER INFORMATION: Amino acid sequence of Fcab FS18-7-9 CH2 and
      CH3 domains without LALA mutation

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 8
<211> LENGTH: 9
<212> TYPE: PRT
<213> ORGANISM: Artificial Sequence
<220> FEATURE:
<223> OTHER INFORMATION: FS18-7-32 CD loop

<400> SEQUENCE: 8

Ser Asn Gly Gln Pro Glu Asn Asn Tyr
1               5

<210> SEQ ID NO 9
<211> LENGTH: 318
<212> TYPE: DNA
<213> ORGANISM: Artificial Sequence
<220> FEATURE:
<223> OTHER INFORMATION: Nucleotide sequence of Fcab FS18-7-32 CH3
      domain

<400> SEQUENCE: 9
ggccagcctc gagaaccaca ggtgtacacc ctgccccat cctgggatga gccgtggggt      60
gaagacgtca gcctgacctg cctggtcaaa ggcttctatc ccagcgaaat cgccgtggag    120
tgggagagca atgggcagcc ggagaacaac tacaagacca cgcctcccgt gctggactcc    180
gacggctcct tcttcctcta cagcaagctc accgtgccgt atgataggtg ggtttggccg    240
gatgagttct catgctccgt gatgcatgag gctctgcaca accactacac acagaagagc    300
ctctccctgt ctccgggt                                                  318

<210> SEQ ID NO 10
<211> LENGTH: 106
<212> TYPE: PRT
<213> ORGANISM: Artificial Sequence
<220> FEATURE:
<223> OTHER INFORMATION: Amino acid sequence of Fcab FS18-7-32 CH3
      domain

<400> SEQUENCE: 10

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
```

```
                    20                  25                  30

Tyr Pro Ser Glu Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 11
<211> LENGTH: 216
<212> TYPE: PRT
<213> ORGANISM: Artificial Sequence
<220> FEATURE:
<223> OTHER INFORMATION: Amino acid sequence of Fcab FS18-7-32 CH2 and
      CH3 domains, comprising LALA mutation

<400> SEQUENCE: 11

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Glu Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 12
<211> LENGTH: 216
<212> TYPE: PRT
<213> ORGANISM: Artificial Sequence
<220> FEATURE:
<223> OTHER INFORMATION: Amino acid sequence of Fcab FS18-7-32 CH2 and
      CH3 domains without LALA mutation
```

-continued

```
<400> SEQUENCE: 12

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Glu Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 13
<211> LENGTH: 9
<212> TYPE: PRT
<213> ORGANISM: Artificial Sequence
<220> FEATURE:
<223> OTHER INFORMATION: FS18-7-33 CD loop

<400> SEQUENCE: 13

Ser Asn Gly Gln Pro Glu Asp Asn Tyr
1               5

<210> SEQ ID NO 14
<211> LENGTH: 318
<212> TYPE: DNA
<213> ORGANISM: Artificial Sequence
<220> FEATURE:
<223> OTHER INFORMATION: Nucleotide sequence of Fcab FS18-7-33 CH3
      domain

<400> SEQUENCE: 14
ggccagcctc gagaaccaca ggtgtacacc ctgcccccat cctgggatga gccgtggggt      60
gaagacgtca gcctgacctg cctggtcaaa ggcttctatc ccagcgacat cgccgtggag    120
tgggagagca atgggcagcc ggaggacaac tacaagacca cgcctcccgt gctggactcc    180
gacggctcct tcttcctcta cagcaagctc accgtgccgt atgataggtg ggtttggccg    240
gatgagttct catgctccgt gatgcatgag gctctgcaca accactacac acagaagagc    300 ctctcccctgt ctccgggt                                                  318
```

<210> SEQ ID NO 15
<211> LENGTH: 106
<212> TYPE: PRT
<213> ORGANISM: Artificial Sequence
<220> FEATURE:
<223> OTHER INFORMATION: Amino acid sequence of Fcab FS18-7-33 CH3 domain

<400> SEQUENCE: 15

```
Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asp Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 16
<211> LENGTH: 216
<212> TYPE: PRT
<213> ORGANISM: Artificial Sequence
<220> FEATURE:
<223> OTHER INFORMATION: Amino acid sequence of Fcab FS18-7-33 CH2 and CH3 domains, comprising LALA mutation

<400> SEQUENCE: 16

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190
```

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 17
<211> LENGTH: 216
<212> TYPE: PRT
<213> ORGANISM: Artificial Sequence
<220> FEATURE:
<223> OTHER INFORMATION: Amino acid sequence of Fcab FS18-7-33 CH2 and
      CH3 domains without LALA mutation

<400> SEQUENCE: 17

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 18
<211> LENGTH: 9
<212> TYPE: PRT
<213> ORGANISM: Artificial Sequence
<220> FEATURE:
<223> OTHER INFORMATION: FS18-7-36 CD loop

<400> SEQUENCE: 18

Ser Asn Gly Gln Pro Glu Asn Asn Tyr
1               5

<210> SEQ ID NO 19
<211> LENGTH: 318
<212> TYPE: DNA
<213> ORGANISM: Artificial Sequence
<220> FEATURE:

```
<223> OTHER INFORMATION: Nucleotide sequence of Fcab FS18-7-36 CH3
      domain

<400> SEQUENCE: 19
ggccagcctc gagaaccaca ggtgtacacc ctgcccccat cctgggatga gccgtggggt    60
gaagacgtca gcctgacctg cctggtcaaa ggcttctatc ccagcgacat cgccgtggag   120
tgggagagca atgggcagcc ggagaacaac tacaagacca cgcctcccgt gctggactcc   180
gacggctcct acttcctcta cagcaagctc accgtgccgt atgataggtg ggtttggccg   240
gatgagttct catgctccgt gatgcatgag gctctgcaca accactacac acagaagagc   300 ctctcccctgt ctccgggt                                                318

<210> SEQ ID NO 20
<211> LENGTH: 106
<212> TYPE: PRT
<213> ORGANISM: Artificial Sequence
<220> FEATURE:
<223> OTHER INFORMATION: Amino acid sequence of Fcab FS18-7-36 CH3
      domain

<400> SEQUENCE: 20

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Tyr
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 21
<211> LENGTH: 216
<212> TYPE: PRT
<213> ORGANISM: Artificial Sequence
<220> FEATURE:
<223> OTHER INFORMATION: Amino acid sequence of CH2+CH3 of Fcab
      FS18-7-36 CH2 and CH3 domains, comprising LALA mutation

<400> SEQUENCE: 21

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
```

```
            100                 105                 110
Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Tyr Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 22
<211> LENGTH: 216
<212> TYPE: PRT
<213> ORGANISM: Artificial Sequence
<220> FEATURE:
<223> OTHER INFORMATION: Amino acid sequence of Fcab FS18-7-36 CH2 and
      CH3 domains without LALA mutation

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Tyr Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 23
<211> LENGTH: 9
```

<212> TYPE: PRT
<213> ORGANISM: Artificial Sequence
<220> FEATURE:
<223> OTHER INFORMATION: FS18-7-58 CD loop

<400> SEQUENCE: 23

Ser Asn Gly Tyr Pro Glu Ile Glu Phe
1               5

<210> SEQ ID NO 24
<211> LENGTH: 318
<212> TYPE: DNA
<213> ORGANISM: Artificial Sequence
<220> FEATURE:
<223> OTHER INFORMATION: Nucleotide sequence of Fcab FS18-7-58 CH3
      domain

<400> SEQUENCE: 24
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggtatcc agaaatcgaa ttcaagacca cgcctcccgt gctggactcc     180
gacggctcct tcttcctcta cagcaagctc accgtgcctt atgataggtg ggtttggccg     240
gatgagttct catgctccgt gatgcatgag gctctgcaca accactacac acagaagagc     300
ctctccctgt ctccgggt                                                   318

<210> SEQ ID NO 25
<211> LENGTH: 106
<212> TYPE: PRT
<213> ORGANISM: Artificial Sequence
<220> FEATURE:
<223> OTHER INFORMATION: Amino acid sequence of Fcab FS18-7-58 CH3
      domain

<400> SEQUENCE: 25

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
                20                  25                  30

Tyr Pro Ser Asp Ile Ala Val Glu Trp Glu Ser Asn Gly Tyr Pro Glu
            35                  40                  45

Ile Glu Phe Lys Thr Thr Pro Pro Val Leu Asp Ser Asp Gly Ser Phe
        50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
                100                 105

<210> SEQ ID NO 26
<211> LENGTH: 216
<212> TYPE: PRT
<213> ORGANISM: Artificial Sequence
<220> FEATURE:
<223> OTHER INFORMATION: Amino acid sequence of Fcab FS18-7-58 CH2 and
      CH3 domains, comprising LALA mutation

<400> SEQUENCE: 26

Ala Pro Glu Ala Ala Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
        100                 105                 110

Pro Arg Glu Pro Gln Val Tyr Thr Leu Pro Pro Ser Trp Asp Glu Pro
    115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Pro Glu Ile Glu
145                 150                 155                 160

Phe Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
            195                 200                 205

Lys Ser Leu Ser Leu Ser Pro Gly
    210                 215

<210> SEQ ID NO 27
<211> LENGTH: 216
<212> TYPE: PRT
<213> ORGANISM: Artificial Sequence
<220> FEATURE:
<223> OTHER INFORMATION: Amino acid sequence of Fcab FS18-7-58 CH2 and
      CH3 domains without LALA mutation

<400> SEQUENCE: 27

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
        100                 105                 110

Pro Arg Glu Pro Gln Val Tyr Thr Leu Pro Pro Ser Trp Asp Glu Pro
    115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Pro Glu Ile Glu
145                 150                 155                 160
```

```
Phe Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 28
<211> LENGTH: 9
<212> TYPE: PRT
<213> ORGANISM: Artificial Sequence
<220> FEATURE:
<223> OTHER INFORMATION: FS18-7-62 CD loop

<400> SEQUENCE: 28

```
Ser Asn Gly Ile Pro Glu Trp Asn Tyr
1               5
```

<210> SEQ ID NO 29
<211> LENGTH: 318
<212> TYPE: DNA
<213> ORGANISM: Artificial Sequence
<220> FEATURE:
<223> OTHER INFORMATION: Nucleotide sequence of Fcab FS18-7-62 CH3
      domain

<400> SEQUENCE: 29

```
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggatccc agaatggaac tataagacca cgcctcccgt gctggactcc     180
gacggctcct tcttcctcta cagcaagctc accgtgccgt atgataggtg ggtttggccg     240
gatgagttct catgctccgt gatgcatgag gctctgcaca accactacac acagaagagc     300
ctctccctgt ctccgggt                                                  318
```

<210> SEQ ID NO 30
<211> LENGTH: 106
<212> TYPE: PRT
<213> ORGANISM: Artificial Sequence
<220> FEATURE:
<223> OTHER INFORMATION: Amino acid sequence of Fcab FS18-7-62 CH3
      domain

<400> SEQUENCE: 30

```
Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Ile Pro Glu
        35                  40                  45

Trp Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 31
<211> LENGTH: 216
<212> TYPE: PRT
<213> ORGANISM: Artificial Sequence
<220> FEATURE:
<223> OTHER INFORMATION: Amino acid sequence of Fcab FS18-7-62 CH2 and
      CH3 domains, comprising LALA mutation

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Ile Pro Glu Trp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 32
<211> LENGTH: 216
<212> TYPE: PRT
<213> ORGANISM: Artificial Sequence
<220> FEATURE:
<223> OTHER INFORMATION: Amino acid sequence of Fcab FS18-7-62 CH2 and
      CH3 domains without LALA mutation

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His

```
                65                  70                  75                  80
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Ile Pro Glu Trp Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 33
<211> LENGTH: 9
<212> TYPE: PRT
<213> ORGANISM: Artificial Sequence
<220> FEATURE:
<223> OTHER INFORMATION: FS18-7-65 CD loop

<400> SEQUENCE: 33

Ser Asn Gly Tyr Ala Glu Tyr Asn Tyr
1               5

<210> SEQ ID NO 34
<211> LENGTH: 318
<212> TYPE: DNA
<213> ORGANISM: Artificial Sequence
<220> FEATURE:
<223> OTHER INFORMATION: Nucleotide sequence of Fcab FS18-7-65 CH3
      domain

<400> SEQUENCE: 34
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggtatgc agaatataac tataagacca cgcctcccgt gctggactcc     180
gacggctcct tcttcctcta cagcaagctc accgtgccgt atgataggtg ggtttggccg     240
gatgagttct catgctccgt gatgcatgag gctctgcaca accactacac acagaagagc     300
ctctccctgt ctccgggt                                                    318

<210> SEQ ID NO 35
<211> LENGTH: 106
<212> TYPE: PRT
<213> ORGANISM: Artificial Sequence
<220> FEATURE:
<223> OTHER INFORMATION: Amino acid sequence of Fcab FS18-7-65 CH3
      domain

<400> SEQUENCE: 35

Gly Gln Pro Arg Glu Pro Gln Val Tyr Thr Leu Pro Pro Ser Trp Asp
1               5                  10                  15
```

```
Glu Pro Trp Gly Glu Asp Val Ser Leu Thr Cys Leu Val Lys Gly Phe
                20                  25                  30

Tyr Pro Ser Asp Ile Ala Val Glu Trp Glu Ser Asn Gly Tyr Ala Glu
            35                  40                  45

Tyr Asn Tyr Lys Thr Thr Pro Pro Val Leu Asp Ser Asp Gly Ser Phe
 50                  55                  60

Phe Leu Tyr Ser Lys Leu Thr Val Pro Tyr Asp Arg Trp Val Trp Pro
 65                  70                  75                  80

Asp Glu Phe Ser Cys Ser Val Met His Glu Ala Leu His Asn His Tyr
                 85                  90                  95

Thr Gln Lys Ser Leu Ser Leu Ser Pro Gly
            100                 105
```

<210> SEQ ID NO 36
<211> LENGTH: 216
<212> TYPE: PRT
<213> ORGANISM: Artificial Sequence
<220> FEATURE:
<223> OTHER INFORMATION: Amino acid sequence of Fcab FS18-7-65 CH2 and
      CH3 domains, comprising LALA mutation

<400> SEQUENCE: 36

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Trp Asp Glu Pro
            115                 120                 125

Trp Gly Glu Asp Val Ser Leu Thr Cys Leu Val Lys Gly Phe Tyr Pro
        130                 135                 140

Ser Asp Ile Ala Val Glu Trp Glu Ser Asn Gly Tyr Ala Glu Tyr Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
        210                 215
```

<210> SEQ ID NO 37
<211> LENGTH: 216
<212> TYPE: PRT
<213> ORGANISM: Artificial Sequence
<220> FEATURE:
<223> OTHER INFORMATION: Amino acid sequence of Fcab FS18-7-65 CH2 and
      CH3 domains without LALA mutation

<400> SEQUENCE: 37

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Ala Glu Tyr Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 38
<211> LENGTH: 9
<212> TYPE: PRT
<213> ORGANISM: Artificial Sequence
<220> FEATURE:
<223> OTHER INFORMATION: FS18-7-78 CD loop

<400> SEQUENCE: 38

```
Ser Asn Gly Tyr Lys Glu Glu Asn Tyr
1               5
```

<210> SEQ ID NO 39
<211> LENGTH: 318
<212> TYPE: DNA
<213> ORGANISM: Artificial Sequence
<220> FEATURE:
<223> OTHER INFORMATION: Nucleotide sequence of Fcab FS18-7-78 CH3
      domain

<400> SEQUENCE: 39

```
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca atgggtataa agaagaaaac tataagacca cgcctcccgt gctggactcc     180
gacggctcct tcttcctcta cagcaagctc accgtgccgt atgataggtg ggtttggccg     240
gatgagttct catgctccgt gatgcatgag gctctgcaca accactacac acagaagagc     300
```
ctctccctgt ctccgggt                                                318

```
<210> SEQ ID NO 40
<211> LENGTH: 106
<212> TYPE: PRT
<213> ORGANISM: Artificial Sequence
<220> FEATURE:
<223> OTHER INFORMATION: Amino acid sequence of Fcab FS18-7-78 CH3
      domain

<400> SEQUENCE: 40
```

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Tyr Lys Glu
        35                  40                  45

Glu Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

```
<210> SEQ ID NO 41
<211> LENGTH: 216
<212> TYPE: PRT
<213> ORGANISM: Artificial Sequence
<220> FEATURE:
<223> OTHER INFORMATION: Amino acid sequence of Fcab FS18-7-78 CH2 and
      CH3 domains, comprising LALA mutation

<400> SEQUENCE: 41
```

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Lys Glu Glu Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu

```
                180             185             190
Phe Ser Cys Ser Val Met His Glu Ala Leu His Asn His Tyr Thr Gln
                195             200             205
Lys Ser Leu Ser Leu Ser Pro Gly
    210             215

<210> SEQ ID NO 42
<211> LENGTH: 216
<212> TYPE: PRT
<213> ORGANISM: Artificial Sequence
<220> FEATURE:
<223> OTHER INFORMATION: Amino acid sequence of Fcab FS18-7-78 CH2 and
      CH3 domains without LALA mutation

<400> SEQUENCE: 42

Ala Pro Glu Leu Leu Gly Gly Pro Ser Val Phe Leu Phe Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Trp Asp Glu Pro
            115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Lys Glu Glu Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Tyr Asp Arg Trp Val Trp Pro Asp Glu
                180                 185                 190

Phe Ser Cys Ser Val Met His Glu Ala Leu His Asn His Tyr Thr Gln
                195                 200                 205

Lys Ser Leu Ser Leu Ser Pro Gly
    210             215

<210> SEQ ID NO 43
<211> LENGTH: 9
<212> TYPE: PRT
<213> ORGANISM: Artificial Sequence
<220> FEATURE:
<223> OTHER INFORMATION: FS18-7-88 CD loop

<400> SEQUENCE: 43

Ser Asn Gly Val Pro Glu Leu Asn Val
1               5

<210> SEQ ID NO 44
<211> LENGTH: 318
<212> TYPE: DNA
<213> ORGANISM: Artificial Sequence
```

<220> FEATURE:
<223> OTHER INFORMATION: Nucleotide sequence of Fcab FS18-7-88 CH3 domain

<400> SEQUENCE: 44

```
ggccagcctc gagaaccaca ggtgtacacc ctgcccccat cctgggatga gccgtggggt      60
gaagacgtca gcctgacctg cctggtcaaa ggcttctatc ccagcgacat cgccgtggag     120
tgggagagca tgggggttcc agaactgaac gttaagacca cgcctcccgt gctggactcc     180
gacggctcct tcttcctcta cagcaagctc accgtgccgt atgataggtg ggtttggccg     240
gatgagttct catgctccgt gatgcatgag gctctgcaca accactacac acagaagagc     300
ctctccctgt ctccgggt                                                    318
```

<210> SEQ ID NO 45
<211> LENGTH: 106
<212> TYPE: PRT
<213> ORGANISM: Artificial Sequence
<220> FEATURE:
<223> OTHER INFORMATION: Amino acid sequence of Fcab FS18-7-88 CH3 domain

<400> SEQUENCE: 45

```
Gly Gln Pro Arg Glu Pro Gln Val Tyr Thr Leu Pro Pro Ser Trp Asp
1               5                   10                  15
Glu Pro Trp Gly Glu Asp Val Ser Leu Thr Cys Leu Val Lys Gly Phe
            20                  25                  30
Tyr Pro Ser Asp Ile Ala Val Glu Trp Glu Ser Asn Gly Val Pro Glu
        35                  40                  45
Leu Asn Val Lys Thr Thr Pro Pro Val Leu Asp Ser Asp Gly Ser Phe
    50                  55                  60
Phe Leu Tyr Ser Lys Leu Thr Val Pro Tyr Asp Arg Trp Val Trp Pro
65                  70                  75                  80
Asp Glu Phe Ser Cys Ser Val Met His Glu Ala Leu His Asn His Tyr
                85                  90                  95
Thr Gln Lys Ser Leu Ser Leu Ser Pro Gly
            100                 105
```

<210> SEQ ID NO 46
<211> LENGTH: 216
<212> TYPE: PRT
<213> ORGANISM: Artificial Sequence
<220> FEATURE:
<223> OTHER INFORMATION: Amino acid sequence of Fcab FS18-7-88 CH2 and CH3 domains, comprising LALA mutation

<400> SEQUENCE: 46

```
Ala Pro Glu Ala Ala Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
```

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
            115                 120                 125

Trp Gly Glu Asp Val Ser Leu Thr Cys Leu Val Lys Gly Phe Tyr Pro
            130                 135                 140

Ser Asp Ile Ala Val Glu Trp Glu Ser Asn Gly Val Pro Glu Leu Asn
145                 150                 155                 160

Val Lys Thr Thr Pro Pro Val Leu Asp Ser Asp Gly Ser Phe Phe Leu
            165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
            195                 200                 205

Lys Ser Leu Ser Leu Ser Pro Gly
            210                 215

<210> SEQ ID NO 47
<211> LENGTH: 216
<212> TYPE: PRT
<213> ORGANISM: Artificial Sequence
<220> FEATURE:
<223> OTHER INFORMATION: Amino acid sequence of Fcab FS18-7-88 CH2 and
      CH3 domains without LALA mutation

<400> SEQUENCE: 47

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Trp Asp Glu Pro
            115                 120                 125

Trp Gly Glu Asp Val Ser Leu Thr Cys Leu Val Lys Gly Phe Tyr Pro
            130                 135                 140

Ser Asp Ile Ala Val Glu Trp Glu Ser Asn Gly Val Pro Glu Leu Asn
145                 150                 155                 160

Val Lys Thr Thr Pro Pro Val Leu Asp Ser Asp Gly Ser Phe Phe Leu
            165                 170                 175

Tyr Ser Lys Leu Thr Val Pro Tyr Asp Arg Trp Val Trp Pro Asp Glu
            180                 185                 190

Phe Ser Cys Ser Val Met His Glu Ala Leu His Asn His Tyr Thr Gln
            195                 200                 205

Lys Ser Leu Ser Leu Ser Pro Gly
            210                 215

<210> SEQ ID NO 48

```
<211> LENGTH: 9
<212> TYPE: PRT
<213> ORGANISM: Artificial Sequence
<220> FEATURE:
<223> OTHER INFORMATION: FS18-7-95 CD loop

<400> SEQUENCE: 48

Ser Asn Gly Tyr Gln Glu Asp Asn Tyr
1               5

<210> SEQ ID NO 49
<211> LENGTH: 318
<212> TYPE: DNA
<213> ORGANISM: Artificial Sequence
<220> FEATURE:
<223> OTHER INFORMATION: Nucleotide sequence of Fcab FS18-7-95 CH3
      domain

<400> SEQUENCE: 49
ggccagcctc gagaaccaca ggtgtacacc ctgcccccat cctgggatga gccgtggggt    60
gaagacgtca gcctgacctg cctggtcaaa ggcttctatc ccagcgacat cgccgtggag   120
tgggagagca atgggtatca ggaagataac tataagacca cgcctcccgt gctggactcc   180
gacggctcct tcttcctcta cagcaagctc accgtgccgt atgataggtg ggtttggccg   240
gatgagttct catgctccgt gatgcatgag gctctgcaca accactacac acagaagagc   300 ctctcccctgt ctccgggt                                                318

<210> SEQ ID NO 50
<211> LENGTH: 106
<212> TYPE: PRT
<213> ORGANISM: Artificial Sequence
<220> FEATURE:
<223> OTHER INFORMATION: Amino acid sequence of Fcab FS18-7-95 CH3
      domain

<400> SEQUENCE: 50

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Tyr Gln Glu
        35                  40                  45

Asp Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 51
<211> LENGTH: 216
<212> TYPE: PRT
<213> ORGANISM: Artificial Sequence
<220> FEATURE:
<223> OTHER INFORMATION: Amino acid sequence of Fcab FS18-7-95 CH2 and
      CH3 domains, comprising LALA mutation

<400> SEQUENCE: 51

Ala Pro Glu Ala Ala Gly Gly Pro Ser Val Phe Leu Phe Pro Pro Lys
1               5                   10                  15
```

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
        100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Gln Glu Asp Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Pro Tyr Asp Arg Trp Val Trp Pro Asp Glu
        180                 185                 190

Phe Ser Cys Ser Val Met His Glu Ala Leu His Asn His Tyr Thr Gln
        195                 200                 205

Lys Ser Leu Ser Leu Ser Pro Gly
        210                 215

<210> SEQ ID NO 52
<211> LENGTH: 216
<212> TYPE: PRT
<213> ORGANISM: Artificial Sequence
<220> FEATURE:
<223> OTHER INFORMATION: Amino acid sequence of Fcab FS18-7-95 CH2 and
      CH3 domains without LALA mutation

<400> SEQUENCE: 52

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
        100                 105                 110

Pro Arg Glu Pro Gln Val Tyr Thr Leu Pro Pro Ser Trp Asp Glu Pro
        115                 120                 125

Trp Gly Glu Asp Val Ser Leu Thr Cys Leu Val Lys Gly Phe Tyr Pro
    130                 135                 140

Ser Asp Ile Ala Val Glu Trp Glu Ser Asn Gly Tyr Gln Glu Asp Asn
```

```
                145                 150                 155                 160
Tyr Lys Thr Thr Pro Val Leu Asp Ser Asp Gly Ser Phe Phe Leu
                    165                 170                 175

Tyr Ser Lys Leu Thr Val Pro Tyr Asp Arg Trp Val Trp Pro Asp Glu
                180                 185                 190

Phe Ser Cys Ser Val Met His Glu Ala Leu His Asn His Tyr Thr Gln
            195                 200                 205

Lys Ser Leu Ser Leu Ser Pro Gly
    210                 215

<210> SEQ ID NO 53
<211> LENGTH: 110
<212> TYPE: PRT
<213> ORGANISM: Artificial Sequence
<220> FEATURE:
<223> OTHER INFORMATION: Amino acid sequence of the wild-type human IgG1
      CH2 domain

<400> SEQUENCE: 53

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 54
<211> LENGTH: 110
<212> TYPE: PRT
<213> ORGANISM: Artificial Sequence
<220> FEATURE:
<223> OTHER INFORMATION: Amino acid sequence of the human IgG1 CH2
      domain comprising the "LALA mutation"

<400> SEQUENCE: 54

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

-continued

```
<210> SEQ ID NO 55
<211> LENGTH: 216
<212> TYPE: PRT
<213> ORGANISM: Artificial Sequence
<220> FEATURE:
<223> OTHER INFORMATION: Amino acid sequence of "wild-type" Fcab CH2 and
      CH3 domains without LALA mutation

<400> SEQUENCE: 55

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 56
<211> LENGTH: 216
<212> TYPE: PRT
<213> ORGANISM: Artificial Sequence
<220> FEATURE:
<223> OTHER INFORMATION: Amino acid sequence of "wild-type" Fcab CH2 and
      CH3 domains, comprising LALA mutation

<400> SEQUENCE: 56

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                    85                  90                  95
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly
    210                 215

<210> SEQ ID NO 57
<211> LENGTH: 15
<212> TYPE: PRT
<213> ORGANISM: Artificial Sequence
<220> FEATURE:
<223> OTHER INFORMATION: Amino acid sequence of the human IgG1 hinge
      region

<400> SEQUENCE: 57

Glu Pro Lys Ser Cys Asp Lys Thr His Thr Cys Pro Pro Cys Pro
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Amino acid sequence of the human IgG1 truncated
      hinge region

<400> SEQUENCE: 58

Thr Cys Pro Pro Cys Pro
1               5

<210> SEQ ID NO 59
<211> LENGTH: 222
<212> TYPE: PRT
<213> ORGANISM: Artificial Sequence
<220> FEATURE:
<223> OTHER INFORMATION: Amino acid sequence anti-mouse LAG-3 Fcab
      FS18-7-108-29, comprising LALA mutation

<400> SEQUENCE: 59

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80
```

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Trp Asp Glu Pro Trp Gly Glu Asp Val Ser Leu Thr Cys Leu
130                 135                 140

Val Lys Gly Phe Tyr Pro Ser Asp Ile Val Val Glu Trp Glu Ser Asn
145                 150                 155                 160

Gly Gln Pro Glu Asn Asn Tyr Lys Thr Thr Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 60
<211> LENGTH: 222
<212> TYPE: PRT
<213> ORGANISM: Artificial Sequence
<220> FEATURE:
<223> OTHER INFORMATION: Amino acid sequence of the anti-mouse LAG-3
      Fcab FS18-7-108-29 without LALA mutation

<400> SEQUENCE: 60

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Trp Asp Glu Pro Trp Gly Glu Asp Val Ser Leu Thr Cys Leu
130                 135                 140

Val Lys Gly Phe Tyr Pro Ser Asp Ile Val Val Glu Trp Glu Ser Asn
145                 150                 155                 160

Gly Gln Pro Glu Asn Asn Tyr Lys Thr Thr Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly

```
            210                 215                 220

<210> SEQ ID NO 61
<211> LENGTH: 222
<212> TYPE: PRT
<213> ORGANISM: Artificial Sequence
<220> FEATURE:
<223> OTHER INFORMATION: Amino acid sequence of the anti-mouse LAG-3
      Fcab FS18-7-108-35, comprising LALA mutation

<400> SEQUENCE: 61

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Trp Asp Glu Pro Trp Gly Glu Asp Val Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Pro Phe Glu Arg
            180                 185                 190

Trp Met Trp Pro Asp Glu Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 62
<211> LENGTH: 222
<212> TYPE: PRT
<213> ORGANISM: Artificial Sequence
<220> FEATURE:
<223> OTHER INFORMATION: Amino acid sequence of the anti-mouse LAG-3
      Fcab FS18-7-108-35 without LALA mutation

<400> SEQUENCE: 62

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
```

```
                65                  70                  75                  80
Val Leu Thr Val Leu His Gln Asp Trp Leu Asn Gly Lys Glu Tyr Lys
                    85                  90                  95

Cys Lys Val Ser Asn Lys Ala Leu Pro Ala Pro Ile Glu Lys Thr Ile
                    100                 105                 110

Ser Lys Ala Lys Gly Gln Pro Arg Glu Pro Gln Val Tyr Thr Leu Pro
                    115                 120                 125

Pro Ser Trp Asp Glu Pro Trp Gly Glu Asp Val Ser Leu Thr Cys Leu
                    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Val Leu Asp Ser
                    165                 170                 175

Asp Gly Ser Phe Phe Leu Tyr Ser Lys Leu Thr Val Pro Phe Glu Arg
                    180                 185                 190

Trp Met Trp Pro Asp Glu Phe Ser Cys Ser Val Met His Glu Ala Leu
                    195                 200                 205

His Asn His Tyr Thr Gln Lys Ser Leu Ser Leu Ser Pro Gly
                    210                 215                 220

<210> SEQ ID NO 63
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-9/4420 comprising LALA mutation

<400> SEQUENCE: 63

Glu Val Lys Leu Asp Glu Thr Gly Gly Gly Leu Val Gln Pro Gly Arg
1                   5                   10                  15

Pro Met Lys Leu Ser Cys Val Ala Ser Gly Phe Thr Phe Ser Asp Tyr
                    20                  25                  30

Trp Met Asn Trp Val Arg Gln Ser Pro Glu Lys Gly Leu Glu Trp Val
                    35                  40                  45

Ala Gln Ile Arg Asn Lys Pro Tyr Asn Tyr Glu Thr Tyr Tyr Ser Asp
                    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                    85                  90                  95

Tyr Cys Thr Gly Ser Tyr Tyr Gly Met Asp Tyr Trp Gly Gln Gly Thr
                    100                 105                 110

Ser Val Thr Val Ser Ser Ala Ser Thr Lys Gly Pro Ser Val Phe Pro
                    115                 120                 125

Leu Ala Pro Ser Ser Lys Ser Thr Ser Gly Gly Thr Ala Ala Leu Gly
                    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205
```

```
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Trp Asp Glu Pro Trp Gly Glu Asp Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Pro Tyr Asp
                405                 410                 415
Arg Trp Val Trp Pro Asp Glu Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 64
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-9/4420 without LALA mutation

<400> SEQUENCE: 64

Glu Val Lys Leu Asp Glu Thr Gly Gly Gly Leu Val Gln Pro Gly Arg
1               5                   10                  15
Pro Met Lys Leu Ser Cys Val Ala Ser Gly Phe Thr Phe Ser Asp Tyr
                20                  25                  30
Trp Met Asn Trp Val Arg Gln Ser Pro Glu Lys Gly Leu Glu Trp Val
            35                  40                  45
Ala Gln Ile Arg Asn Lys Pro Tyr Asn Tyr Glu Thr Tyr Tyr Ser Asp
        50                  55                  60
Ser Val Lys Gly Arg Phe Thr Ile Ser Arg Asp Asp Ser Lys Ser Ser
65                  70                  75                  80
Val Tyr Leu Gln Met Asn Asn Leu Arg Val Glu Asp Met Gly Ile Tyr
                85                  90                  95
Tyr Cys Thr Gly Ser Tyr Tyr Gly Met Asp Tyr Trp Gly Gln Gly Thr
                100                 105                 110
Ser Val Thr Val Ser Ser Ala Ser Thr Lys Gly Pro Ser Val Phe Pro
            115                 120                 125
```

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 65
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-32/4420 comprising LALA mutation

<400> SEQUENCE: 65

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val

Ala Gln Ile Arg Asn Lys Pro Tyr Asn Tyr Glu Thr Tyr Tyr Ser Asp
 35                  40                  45                  50

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Glu Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 66

```
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-32/without LALA mutation

<400> SEQUENCE: 66
```

| | | | | | | | | | | | | | | |
|---|---|---|---|---|---|---|---|---|---|---|---|---|---|---|
| Glu | Val | Lys | Leu | Asp | Glu | Thr | Gly | Gly | Leu | Val | Gln | Pro | Gly | Arg |
| 1 | | | | 5 | | | | | 10 | | | | | 15 |
| Pro | Met | Lys | Leu | Ser | Cys | Val | Ala | Ser | Gly | Phe | Thr | Phe | Ser | Asp | Tyr |
| | | | 20 | | | | | 25 | | | | | 30 | |
| Trp | Met | Asn | Trp | Val | Arg | Gln | Ser | Pro | Glu | Lys | Gly | Leu | Glu | Trp | Val |
| | | 35 | | | | | 40 | | | | | 45 | | |
| Ala | Gln | Ile | Arg | Asn | Lys | Pro | Tyr | Asn | Tyr | Glu | Thr | Tyr | Tyr | Ser | Asp |
| | 50 | | | | | 55 | | | | | 60 | | | | |
| Ser | Val | Lys | Gly | Arg | Phe | Thr | Ile | Ser | Arg | Asp | Asp | Ser | Lys | Ser | Ser |
| 65 | | | | | 70 | | | | | 75 | | | | | 80 |
| Val | Tyr | Leu | Gln | Met | Asn | Asn | Leu | Arg | Val | Glu | Asp | Met | Gly | Ile | Tyr |
| | | | | 85 | | | | | 90 | | | | | 95 | |
| Tyr | Cys | Thr | Gly | Ser | Tyr | Tyr | Gly | Met | Asp | Tyr | Trp | Gly | Gln | Gly | Thr |
| | | | 100 | | | | | 105 | | | | | 110 | | |
| Ser | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Trp | Asp | Glu | Pro | Trp | Gly | Glu | Asp | Val | Ser | Leu | Thr | Cys |
| | | 355 | | | | | 360 | | | | | 365 | | | |
| Leu | Val | Lys | Gly | Phe | Tyr | Pro | Ser | Glu | Ile | Ala | Val | Glu | Trp | Glu | Ser |

```
                370                 375                 380
Asn Gly Gln Pro Glu Asn Asn Tyr Lys Thr Thr Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 67
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-33/4420 comprising LALA mutation

<400> SEQUENCE: 67

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
435                 440                 445

<210> SEQ ID NO 68
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-33/4420 without LALA mutation

<400> SEQUENCE: 68

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
            405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 69
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-36/4420 comprising LALA mutation

<400> SEQUENCE: 69

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
```

|  | 115 |  |  |  | 120 |  |  |  | 125 |  |  |
|---|---|---|---|---|---|---|---|---|---|---|---|

Leu Ala Pro Ser Ser Lys Ser Thr Ser Gly Gly Thr Ala Ala Leu Gly
    130                    135               140

Cys Leu Val Lys Asp Tyr Phe Pro Glu Pro Val Thr Val Ser Trp Asn
145                  150               155                 160

Ser Gly Ala Leu Thr Ser Gly Val His Thr Phe Pro Ala Val Leu Gln
                165               170               175

Ser Ser Gly Leu Tyr Ser Leu Ser Ser Val Val Thr Val Pro Ser Ser
            180               185               190

Ser Leu Gly Thr Gln Thr Tyr Ile Cys Asn Val Asn His Lys Pro Ser
            195               200               205

Asn Thr Lys Val Asp Lys Lys Val Glu Pro Lys Ser Cys Asp Lys Thr
   210                    215               220

His Thr Cys Pro Pro Cys Pro Ala Pro Glu Ala Ala Gly Gly Pro Ser
225                  230               235                 240

Val Phe Leu Phe Pro Pro Lys Pro Lys Asp Thr Leu Met Ile Ser Arg
                245               250               255

Thr Pro Glu Val Thr Cys Val Val Val Asp Val Ser His Glu Asp Pro
            260               265               270

Glu Val Lys Phe Asn Trp Tyr Val Asp Gly Val Glu Val His Asn Ala
            275               280               285

Lys Thr Lys Pro Arg Glu Glu Gln Tyr Asn Ser Thr Tyr Arg Val Val
   290                    295               300

Ser Val Leu Thr Val Leu His Gln Asp Trp Leu Asn Gly Lys Glu Tyr
305                  310               315                 320

Lys Cys Lys Val Ser Asn Lys Ala Leu Pro Ala Pro Ile Glu Lys Thr
                325               330               335

Ile Ser Lys Ala Lys Gly Gln Pro Arg Glu Pro Gln Val Tyr Thr Leu
            340               345               350

Pro Pro Ser Trp Asp Glu Pro Trp Gly Glu Asp Val Ser Leu Thr Cys
            355               360               365

Leu Val Lys Gly Phe Tyr Pro Ser Asp Ile Ala Val Glu Trp Glu Ser
   370                    375               380

Asn Gly Gln Pro Glu Asn Asn Tyr Lys Thr Thr Pro Pro Val Leu Asp
385                  390               395                 400

Ser Asp Gly Ser Tyr Phe Leu Tyr Ser Lys Leu Thr Val Pro Tyr Asp
                405               410               415

Arg Trp Val Trp Pro Asp Glu Phe Ser Cys Ser Val Met His Glu Ala
            420               425               430

Leu His Asn His Tyr Thr Gln Lys Ser Leu Ser Leu Ser Pro Gly
            435               440               445

<210> SEQ ID NO 70
<211> LENGTH: 447
<212> TYPE: PRT
<213> ORGANISM: Artificial Sequence
<220> FEATURE:
<223> OTHER INFORMATION: Amino acid sequence of the heavy chain of
     anti-human LAG-3/FITC mAb2 FS18-7-36/4420 without LALA mutation

<400> SEQUENCE: 70

Glu Val Lys Leu Asp Glu Thr Gly Gly Gly Leu Val Gln Pro Gly Arg
1                 5                    10                 15

Pro Met Lys Leu Ser Cys Val Ala Ser Gly Phe Thr Phe Ser Asp Tyr
                20               25               30

-continued

```
Trp Met Asn Trp Val Arg Gln Ser Pro Glu Lys Gly Leu Glu Trp Val
         35                  40                  45
Ala Gln Ile Arg Asn Lys Pro Tyr Asn Tyr Glu Thr Tyr Tyr Ser Asp
 50                  55                  60
Ser Val Lys Gly Arg Phe Thr Ile Ser Arg Asp Asp Ser Lys Ser Ser
 65                  70                  75                  80
Val Tyr Leu Gln Met Asn Asn Leu Arg Val Glu Asp Met Gly Ile Tyr
                 85                  90                  95
Tyr Cys Thr Gly Ser Tyr Tyr Gly Met Asp Tyr Trp Gly Gln Gly Thr
             100                 105                 110
Ser Val Thr Val Ser Ser Ala Ser Thr Lys Gly Pro Ser Val Phe Pro
         115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                 165                 170                 175
Ser Ser Gly Leu Tyr Ser Leu Ser Ser Val Val Thr Val Pro Ser Ser
             180                 185                 190
Ser Leu Gly Thr Gln Thr Tyr Ile Cys Asn Val Asn His Lys Pro Ser
         195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                 245                 250                 255
Thr Pro Glu Val Thr Cys Val Val Val Asp Val Ser His Glu Asp Pro
             260                 265                 270
Glu Val Lys Phe Asn Trp Tyr Val Asp Gly Val Glu Val His Asn Ala
         275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                 325                 330                 335
Ile Ser Lys Ala Lys Gly Gln Pro Arg Glu Pro Gln Val Tyr Thr Leu
             340                 345                 350
Pro Pro Ser Trp Asp Glu Pro Trp Gly Glu Asp Val Ser Leu Thr Cys
         355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Tyr Phe Leu Tyr Ser Lys Leu Thr Val Pro Tyr Asp
                 405                 410                 415
Arg Trp Val Trp Pro Asp Glu Phe Ser Cys Ser Val Met His Glu Ala
             420                 425                 430
Leu His Asn His Tyr Thr Gln Lys Ser Leu Ser Leu Ser Pro Gly
         435                 440                 445
```

-continued

```
<210> SEQ ID NO 71
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-58/4420 comprising LALA mutation

<400> SEQUENCE: 71
```

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
370                 375                 380

Asn Gly Tyr Pro Glu Ile Glu Phe Lys Thr Thr Pro Pro Val Leu Asp
385                 390                 395                 400

Ser Asp Gly Ser Phe Phe Leu Tyr Ser Lys Leu Thr Val Pro Tyr Asp
            405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 72
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-58/4420 without LALA mutation

<400> SEQUENCE: 72

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

```
Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
            370                 375                 380

Asn Gly Tyr Pro Glu Ile Glu Phe Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 73
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-62/4420 comprising LALA mutation

<400> SEQUENCE: 73

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
            195                 200                 205
Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Ile Pro Glu Trp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 74
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-62/4420 without LALA mutation

<400> SEQUENCE: 74

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110
```

```
Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
    355                 360                 365

Leu Val Lys Gly Phe Tyr Pro Ser Asp Ile Ala Val Glu Trp Glu Ser
370                 375                 380

Asn Gly Ile Pro Glu Trp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
    435                 440                 445

<210> SEQ ID NO 75
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-65/4420 comprising LALA mutation

<400> SEQUENCE: 75

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30
```

-continued

```
Trp Met Asn Trp Val Arg Gln Ser Pro Glu Lys Gly Leu Glu Trp Val
         35                  40                  45

Ala Gln Ile Arg Asn Lys Pro Tyr Asn Tyr Glu Thr Tyr Tyr Ser Asp
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Tyr Ala Glu Tyr Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 76
<211> LENGTH: 447
<212> TYPE: PRT
<213> ORGANISM: Artificial Sequence
<220> FEATURE:
<223> OTHER INFORMATION: Amino acid sequence of the heavy chain of
     anti-human LAG-3/FITC mAb2 FS18-7-65/4420 without LALA mutation

<400> SEQUENCE: 76

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365
```

```
Leu Val Lys Gly Phe Tyr Pro Ser Asp Ile Ala Val Glu Trp Glu Ser
        370                 375                 380

Asn Gly Tyr Ala Glu Tyr Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 77
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-78/4420 comprising LALA mutation

<400> SEQUENCE: 77

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

-continued

```
                    275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Trp Asp Glu Pro Trp Gly Glu Asp Val Ser Leu Thr Cys
                355                 360                 365
Leu Val Lys Gly Phe Tyr Pro Ser Asp Ile Ala Val Glu Trp Glu Ser
    370                 375                 380
Asn Gly Tyr Lys Glu Glu Asn Tyr Lys Thr Thr Pro Pro Val Leu Asp
385                 390                 395                 400
Ser Asp Gly Ser Phe Phe Leu Tyr Ser Lys Leu Thr Val Pro Tyr Asp
                405                 410                 415
Arg Trp Val Trp Pro Asp Glu Phe Ser Cys Ser Val Met His Glu Ala
            420                 425                 430
Leu His Asn His Tyr Thr Gln Lys Ser Leu Ser Leu Ser Pro Gly
    435                 440                 445
```

<210> SEQ ID NO 78
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-78/4420 without LALA mutation

<400> SEQUENCE: 78

```
Glu Val Lys Leu Asp Glu Thr Gly Gly Gly Leu Val Gln Pro Gly Arg
1               5                   10                  15
Pro Met Lys Leu Ser Cys Val Ala Ser Gly Phe Thr Phe Ser Asp Tyr
            20                  25                  30
Trp Met Asn Trp Val Arg Gln Ser Pro Glu Lys Gly Leu Glu Trp Val
        35                  40                  45
Ala Gln Ile Arg Asn Lys Pro Tyr Asn Tyr Glu Thr Tyr Tyr Ser Asp
    50                  55                  60
Ser Val Lys Gly Arg Phe Thr Ile Ser Arg Asp Asp Ser Lys Ser Ser
65                  70                  75                  80
Val Tyr Leu Gln Met Asn Asn Leu Arg Val Glu Asp Met Gly Ile Tyr
                85                  90                  95
Tyr Cys Thr Gly Ser Tyr Tyr Gly Met Asp Tyr Trp Gly Gln Gly Thr
            100                 105                 110
Ser Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
```

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Tyr Lys Glu Glu Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 79
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-88/4420 comprising LALA mutation

<400> SEQUENCE: 79

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

```
Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
        340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
        370                 375                 380

Asn Gly Val Pro Glu Leu Asn Val Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
                420                 425                 430

Leu His Asn His Tyr Thr Gln Lys Ser Leu Ser Leu Ser Pro Gly
        435                 440                 445

<210> SEQ ID NO 80
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-88/4420 without LALA mutation

<400> SEQUENCE: 80

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
```

```
            20                  25                  30
Trp Met Asn Trp Val Arg Gln Ser Pro Glu Lys Gly Leu Glu Trp Val
         35                  40                  45

Ala Gln Ile Arg Asn Lys Pro Tyr Asn Tyr Glu Thr Tyr Tyr Ser Asp
     50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                 85                  90                  95

Tyr Cys Thr Gly Ser Tyr Tyr Gly Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ala Val Glu Trp Glu Ser
    370                 375                 380

Asn Gly Val Pro Glu Leu Asn Val Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 81
<211> LENGTH: 447
<212> TYPE: PRT
<213> ORGANISM: Artificial Sequence
<220> FEATURE:
<223> OTHER INFORMATION: Amino acid sequence of the heavy chain of
anti-human LAG-3/FITC mAb2 FS18-7-95/4420 comprising LALA mutation

<400> SEQUENCE: 81

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys

```
            355                 360                 365
Leu Val Lys Gly Phe Tyr Pro Ser Asp Ile Ala Val Glu Trp Glu Ser
        370                 375                 380

Asn Gly Tyr Gln Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 82
<211> LENGTH: 447
<212> TYPE: PRT
<213> ORGANISM: Artificial Sequence
<220> FEATURE:
<223> OTHER INFORMATION: Amino acid sequence of the heavy chain of
      anti-human LAG-3/FITC mAb2 FS18-7-95/4420 without LALA mutation

<400> SEQUENCE: 82

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ala Val Glu Trp Glu Ser
        370                 375                 380

Asn Gly Tyr Gln Glu Asp Asn Tyr Lys Thr Thr Pro Pro Val Leu Asp
385                 390                 395                 400

Ser Asp Gly Ser Phe Phe Leu Tyr Ser Lys Leu Thr Val Pro Tyr Asp
                405                 410                 415

Arg Trp Val Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 83
<211> LENGTH: 447
<212> TYPE: PRT
<213> ORGANISM: Artificial Sequence
<220> FEATURE:
<223> OTHER INFORMATION: Amino acid sequence of the heavy chain of
      anti-FITC mAb 4420 comprising LALA mutation

<400> SEQUENCE: 83

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190
```

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 84
<211> LENGTH: 447
<212> TYPE: PRT
<213> ORGANISM: Artificial Sequence
<220> FEATURE:
<223> OTHER INFORMATION: Amino acid sequence of the heavy chain of
      anti-FITC mAb 4420 without LALA mutation

<400> SEQUENCE: 84

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr

```
                100                 105                 110
Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 85
<211> LENGTH: 219
<212> TYPE: PRT
<213> ORGANISM: Artificial Sequence
<220> FEATURE:
<223> OTHER INFORMATION: Amino acid sequence of the anti-FITC mAb 4420
      light chain

<400> SEQUENCE: 85

Asp Val Val Met Thr Gln Thr Pro Leu Ser Leu Pro Val Ser Leu Gly
1               5                   10                  15
```

```
Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 86
<211> LENGTH: 8
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to IMGT) HCDR1

<400> SEQUENCE: 86

Gly Phe Thr Phe Asp Asp Tyr Ala
1               5

<210> SEQ ID NO 87
<211> LENGTH: 8
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to IMGT) HCDR2

<400> SEQUENCE: 87

Ile Ser Trp Lys Ser Asn Ile Ile
1               5

<210> SEQ ID NO 88
<211> LENGTH: 15
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to IMGT) HCDR3

<400> SEQUENCE: 88

Ala Arg Asp Ile Thr Gly Ser Gly Ser Tyr Gly Trp Phe Asp Pro
```

<210> SEQ ID NO 89
<211> LENGTH: 6
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to IMGT) LCDR1

<400> SEQUENCE: 89

Gln Ser Ile Ser Ser Tyr
1               5

<210> SEQ ID NO 90
<211> LENGTH: 3
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to IMGT) LCDR2

<400> SEQUENCE: 90

Val Ala Ser
1

<210> SEQ ID NO 91
<211> LENGTH: 9
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to IMGT) LCDR3

<400> SEQUENCE: 91

Gln Gln Ser Tyr Ser Asn Pro Ile Thr
1               5

<210> SEQ ID NO 92
<211> LENGTH: 122
<212> TYPE: PRT
<213> ORGANISM: Artificial Sequence
<220> FEATURE:
<223> OTHER INFORMATION: Amino acid sequence of the anti-PD-L1 antibody
      84G09 VH domain

<400> SEQUENCE: 92

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser
        115                 120

```
<210> SEQ ID NO 93
<211> LENGTH: 107
<212> TYPE: PRT
<213> ORGANISM: Artificial Sequence
<220> FEATURE:
<223> OTHER INFORMATION: Amino acid sequence of the anti-PD-L1 antibody
      84G09 VL domain

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys
            100                 105

<210> SEQ ID NO 94
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-9/84G09 with LALA mutation heavy chain

<400> SEQUENCE: 94

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 95
<211> LENGTH: 451
<212> TYPE: PRT
<213> ORGANISM: Artificial Sequence
<220> FEATURE:
<223> OTHER INFORMATION: Amino acid sequence of the anti-human
    LAG-3/PD-L1 mAb2 FS18-7-9/84G09 heavy chain

<400> SEQUENCE: 95

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 96
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-32/84G09 with LALA mutation heavy chain
```

<400> SEQUENCE: 96

```
Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Glu Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
            435                 440                 445

Ser Pro Gly
        450

<210> SEQ ID NO 97
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-32/84G09 heavy chain

<400> SEQUENCE: 97

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
            35                  40                  45

Ser Gly Ile Ser Trp Lys Ser Asn Ile Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
```

```
            305                 310                 315                 320
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Trp Asp Glu Pro Trp Gly Glu Asp Val
                355                 360                 365

Ser Leu Thr Cys Leu Val Lys Gly Phe Tyr Pro Ser Glu Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
                420                 425                 430

Met His Glu Ala Leu His Asn His Tyr Thr Gln Lys Ser Leu Ser Leu
                435                 440                 445

Ser Pro Gly
        450

<210> SEQ ID NO 98
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-33/84G09 with LALA mutation heavy chain

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Thr Pro Gly Lys Gly Leu Glu Trp Val
            35                  40                  45

Ser Gly Ile Ser Trp Lys Ser Asn Ile Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asp Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 99
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-33/84G09 heavy chain

<400> SEQUENCE: 99

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asp Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 100
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-36/84G09 with LALA mutation heavy chain

<400> SEQUENCE: 100

Glu Val Gln Leu Val Glu Ser Gly Gly Gly Leu Val Gln Pro Gly Arg

```
1               5                   10                  15
Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
            35                  40                  45

Ser Gly Ile Ser Trp Lys Ser Asn Ile Ile Gly Tyr Ala Asp Ser Val
            50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Leu Tyr Tyr Cys
            85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Tyr Phe Leu Tyr Ser Lys Leu Thr
                405                 410                 415

Val Pro Tyr Asp Arg Trp Val Trp Pro Asp Glu Phe Ser Cys Ser Val
                420                 425                 430
```

```
Met His Glu Ala Leu His Asn His Tyr Thr Gln Lys Ser Leu Ser Leu
        435                 440                 445

Ser Pro Gly
    450

<210> SEQ ID NO 101
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-36/84G09 heavy chain

<400> SEQUENCE: 101

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
```

```
                    325                 330                 335
Ile Glu Lys Thr Ile Ser Lys Ala Lys Gly Gln Pro Arg Glu Pro Gln
                340                 345                 350

Val Tyr Thr Leu Pro Pro Ser Trp Asp Glu Pro Trp Gly Glu Asp Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Tyr Phe Leu Tyr Ser Lys Leu Thr
                405                 410                 415

Val Pro Tyr Asp Arg Trp Val Trp Pro Asp Glu Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 102
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-58/84G09 with LALA mutation heavy chain

<400> SEQUENCE: 102

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Thr Pro Gly Lys Gly Leu Glu Trp Val
                35                  40                  45

Ser Gly Ile Ser Trp Lys Ser Asn Ile Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
        210                 215                 220
```

-continued

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
            355                 360                 365

Ser Leu Thr Cys Leu Val Lys Gly Phe Tyr Pro Ser Asp Ile Ala Val
370                 375                 380

Glu Trp Glu Ser Asn Gly Tyr Pro Glu Ile Glu Phe Lys Thr Thr Pro
385                 390                 395                 400

Pro Val Leu Asp Ser Asp Gly Ser Phe Phe Leu Tyr Ser Lys Leu Thr
            405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 103
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-58/84G09 heavy chain

<400> SEQUENCE: 103

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
    370                 375                 380

Glu Trp Glu Ser Asn Gly Tyr Pro Glu Ile Glu Phe Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 104
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-62/84G09 with LALA mutation heavy chain

<400> SEQUENCE: 104

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr

```
                    20                  25                  30
Ala Met His Trp Val Arg Gln Thr Pro Gly Lys Gly Leu Glu Trp Val
                35                  40                  45
Ser Gly Ile Ser Trp Lys Ser Asn Ile Ile Gly Tyr Ala Asp Ser Val
            50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                85                  90                  95
Ala Arg Asp Ile Thr Gly Ser Gly Ser Tyr Gly Trp Phe Asp Pro Trp
               100                 105                 110
Gly Gln Gly Thr Leu Val Thr Val Ser Ser Ala Ser Thr Lys Gly Pro
               115                 120                 125
Ser Val Phe Pro Leu Ala Pro Ser Ser Lys Ser Thr Ser Gly Gly Thr
           130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
               165                 170                 175
Ala Val Leu Gln Ser Ser Gly Leu Tyr Ser Leu Ser Ser Val Val Thr
               180                 185                 190
Val Pro Ser Ser Ser Leu Gly Thr Gln Thr Tyr Ile Cys Asn Val Asn
           195                 200                 205
His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Ala Ala
225                 230                 235                 240
Gly Gly Pro Ser Val Phe Leu Phe Pro Pro Lys Pro Lys Asp Thr Leu
               245                 250                 255
Met Ile Ser Arg Thr Pro Glu Val Thr Cys Val Val Val Asp Val Ser
           260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
               325                 330                 335
Ile Glu Lys Thr Ile Ser Lys Ala Lys Gly Gln Pro Arg Glu Pro Gln
               340                 345                 350
Val Tyr Thr Leu Pro Pro Ser Trp Asp Glu Pro Trp Gly Glu Asp Val
           355                 360                 365
Ser Leu Thr Cys Leu Val Lys Gly Phe Tyr Pro Ser Asp Ile Ala Val
        370                 375                 380
Glu Trp Glu Ser Asn Gly Ile Pro Glu Trp Asn Tyr Lys Thr Thr Pro
385                 390                 395                 400
Pro Val Leu Asp Ser Asp Gly Ser Phe Phe Leu Tyr Ser Lys Leu Thr
               405                 410                 415
Val Pro Tyr Asp Arg Trp Val Trp Pro Asp Glu Phe Ser Cys Ser Val
           420                 425                 430
Met His Glu Ala Leu His Asn His Tyr Thr Gln Lys Ser Leu Ser Leu
        435                 440                 445
```

```
Ser Pro Gly
    450

<210> SEQ ID NO 105
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-62/84G09 heavy chain

<400> SEQUENCE: 105

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
```

```
            340             345             350
Val Tyr Thr Leu Pro Pro Ser Trp Asp Glu Pro Trp Gly Glu Asp Val
        355             360             365

Ser Leu Thr Cys Leu Val Lys Gly Phe Tyr Pro Ser Asp Ile Ala Val
    370             375             380

Glu Trp Glu Ser Asn Gly Ile Pro Glu Trp Asn Tyr Lys Thr Thr Pro
385             390             395             400

Pro Val Leu Asp Ser Asp Gly Ser Phe Phe Leu Tyr Ser Lys Leu Thr
            405             410             415

Val Pro Tyr Asp Arg Trp Val Trp Pro Asp Glu Phe Ser Cys Ser Val
        420             425             430

Met His Glu Ala Leu His Asn His Tyr Thr Gln Lys Ser Leu Ser Leu
        435             440             445

Ser Pro Gly
    450

<210> SEQ ID NO 106
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-65/84G09 with LALA mutation heavy chain

<400> SEQUENCE: 106

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240
```

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Tyr Ala Glu Tyr Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 107
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-65/84G09 heavy chain

<400> SEQUENCE: 107

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140
```

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Val Val Thr
        180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
        370                 375                 380

Glu Trp Glu Ser Asn Gly Tyr Ala Glu Tyr Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 108
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-78/84G09 with LALA mutation heavy chain

<400> SEQUENCE: 108

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val

```
            35                  40                  45
Ser Gly Ile Ser Trp Lys Ser Asn Ile Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
        370                 375                 380

Glu Trp Glu Ser Asn Gly Tyr Lys Glu Asn Tyr Lys Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Pro Asp Glu Phe Cys Ser Val
            420                 425                 430

Met His Glu Ala Leu His Asn His Tyr Thr Gln Lys Ser Leu Ser Leu
        435                 440                 445

Ser Pro Gly
        450
```

<210> SEQ ID NO 109
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-78/84G09 heavy chain

<400> SEQUENCE: 109

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
```

```
                  355                 360                 365
Ser Leu Thr Cys Leu Val Lys Gly Phe Tyr Pro Ser Asp Ile Ala Val
    370                 375                 380

Glu Trp Glu Ser Asn Gly Tyr Lys Glu Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 110
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-88/84G09 with LALA mutation heavy chain

<400> SEQUENCE: 110

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255
```

Met Ile Ser Arg Thr Pro Glu Val Thr Cys Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
370                 375                 380

Glu Trp Glu Ser Asn Gly Val Pro Glu Leu Asn Val Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 111
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-88/84G09 heavy chain

<400> SEQUENCE: 111

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
        355                 360                 365

Ser Leu Thr Cys Leu Val Lys Gly Phe Tyr Pro Ser Asp Ile Ala Val
        370                 375                 380

Glu Trp Glu Ser Asn Gly Val Pro Glu Leu Asn Val Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 112
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-95/84G09 with LALA mutation heavy chain

<400> SEQUENCE: 112

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Ile Thr Gly Ser Gly Ser Tyr Gly Trp Phe Asp Pro Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Trp Asp Glu Pro Trp Gly Glu Asp Val
            355                 360                 365

Ser Leu Thr Cys Leu Val Lys Gly Phe Tyr Pro Ser Asp Ile Ala Val
            370                 375                 380

Glu Trp Glu Ser Asn Gly Tyr Gln Glu Asp Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
                420                 425                 430

Met His Glu Ala Leu His Asn His Tyr Thr Gln Lys Ser Leu Ser Leu
            435                 440                 445

Ser Pro Gly
    450

<210> SEQ ID NO 113
```

```
<211> LENGTH: 451
<212> TYPE: PRT
<213> ORGANISM: Artificial Sequence
<220> FEATURE:
<223> OTHER INFORMATION: Amino acid sequence of the anti-human
      LAG-3/PD-L1 mAb2 FS18-7-95/84G09 heavy chain

<400> SEQUENCE: 113
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Asp | Asp | Tyr |
| | | | 20 | | | | | 25 | | | | | 30 | | |
| Ala | Met | His | Trp | Val | Arg | Gln | Thr | Pro | Gly | Lys | Gly | Leu | Glu | Trp | Val |
| | | 35 | | | | | 40 | | | | | 45 | | | |
| Ser | Gly | Ile | Ser | Trp | Lys | Ser | Asn | Ile | Ile | Gly | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 | |
| Ala | Arg | Asp | Ile | Thr | Gly | Ser | Gly | Ser | Tyr | Gly | Trp | Phe | Asp | Pro | Trp |
| | | | 100 | | | | | 105 | | | | | 110 | | |
| Gly | Gln | Gly | Thr | Leu | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Ser | Ser | Lys | Ser | Thr | Ser | Gly | Gly | Thr |
| | 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |
| His | Lys | Pro | Ser | Asn | Thr | Lys | Val | Asp | Lys | Lys | Val | Glu | Pro | Lys | Ser |
| | 210 | | | | | 215 | | | | | 220 | | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Arg | Asp | Glu | Pro | Trp | Gly | Glu | Asp | Val |
| | | 355 | | | | | 360 | | | | | 365 | | | |
| Ser | Leu | Thr | Cys | Leu | Val | Lys | Gly | Phe | Tyr | Pro | Ser | Asp | Ile | Ala | Val |

```
            370                 375                 380
Glu Trp Glu Ser Asn Gly Tyr Gln Glu Asp Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Pro Tyr Asp Arg Trp Val Trp Pro Asp Glu Phe Ser Cys Ser Val
                420                 425                 430

Met His Glu Ala Leu His Asn His Tyr Thr Gln Lys Ser Leu Ser Leu
                435                 440                 445

Ser Pro Gly
        450

<210> SEQ ID NO 114
<211> LENGTH: 451
<212> TYPE: PRT
<213> ORGANISM: Artificial Sequence
<220> FEATURE:
<223> OTHER INFORMATION: Amino acid sequence of the anti-human PD-L1 mAb
      84G09 with LALA heavy chain

<400> SEQUENCE: 114

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Thr Pro Gly Lys Gly Leu Glu Trp Val
            35                  40                  45

Ser Gly Ile Ser Trp Lys Ser Asn Ile Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 115
<211> LENGTH: 451
<212> TYPE: PRT
<213> ORGANISM: Artificial Sequence
<220> FEATURE:
<223> OTHER INFORMATION: Amino acid sequence of the anti-human PD-L1 mAb
      84G09 heavy chain

<400> SEQUENCE: 115

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 116
<211> LENGTH: 214
<212> TYPE: PRT
<213> ORGANISM: Artificial Sequence
<220> FEATURE:
<223> OTHER INFORMATION: Amino acid sequence of the anti-human PD-L1 mAb
      84G09 light chain

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro

```
            65                 70                 75                 80
Glu Asp Phe Ala Thr Tyr Tyr Cys Gln Gln Ser Tyr Ser Asn Pro Ile
                     85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 117
<211> LENGTH: 447
<212> TYPE: PRT
<213> ORGANISM: Artificial Sequence
<220> FEATURE:
<223> OTHER INFORMATION: Amino acid sequence of the anti-mouse
      LAG-3/PD-L1 mAb2 FS18-7-108-29/S1 with LALA mutation heavy chain

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205
```

```
Asn Thr Lys Val Asp Lys Lys Val Glu Pro Lys Ser Cys Asp Lys Thr
210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Trp Asp Glu Pro Trp Gly Glu Asp Val Ser Leu Thr Cys
        355                 360                 365
Leu Val Lys Gly Phe Tyr Pro Ser Asp Ile Val Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Pro Phe Glu
                405                 410                 415
Arg Trp Met Trp Pro Asp Glu Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 118
<211> LENGTH: 447
<212> TYPE: PRT
<213> ORGANISM: Artificial Sequence
<220> FEATURE:
<223> OTHER INFORMATION: Amino acid sequence of the anti-mouse
      LAG-3/PD-L1 mAb2 FS18-7-108-29/S1 heavy chain

<400> SEQUENCE: 118

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ala Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Val Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 119
<211> LENGTH: 214
<212> TYPE: PRT
<213> ORGANISM: Artificial Sequence
<220> FEATURE:
<223> OTHER INFORMATION: Amino acid sequence of the anti-mouse PD-L1 mAb
      S1 light chain

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
```

```
                35                  40                  45
Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 120
<211> LENGTH: 447
<212> TYPE: PRT
<213> ORGANISM: Artificial Sequence
<220> FEATURE:
<223> OTHER INFORMATION: Amino acid sequence of the anti-mouse
      LAG-3/PD-L1 mAb2 FS18-7-108-35/S1 with LALA mutation heavy chain

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ser Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 121
<211> LENGTH: 447
<212> TYPE: PRT
<213> ORGANISM: Artificial Sequence
<220> FEATURE:
<223> OTHER INFORMATION: Amino acid sequence of the anti-mouse
      LAG-3/PD-L1 mAb2 FS18-7-108-35/S1 heavy chain

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

```
Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
            355                 360                 365

Leu Val Lys Gly Phe Tyr Pro Ser Asp Ile Ser Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 122
<211> LENGTH: 447
<212> TYPE: PRT
<213> ORGANISM: Artificial Sequence
<220> FEATURE:
<223> OTHER INFORMATION: Amino acid sequence of the control PD-L1 mAb S1
      with LALA mutation heavy chain

<400> SEQUENCE: 122

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
                35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
                100                 105                 110

Leu Val Thr Val Ser Ala Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430
```

Leu His Asn His Tyr Thr Gln Lys Ser Leu Ser Leu Ser Pro Gly
              435                 440                 445

<210> SEQ ID NO 123
<211> LENGTH: 447
<212> TYPE: PRT
<213> ORGANISM: Artificial Sequence
<220> FEATURE:
<223> OTHER INFORMATION: Amino acid sequence of the control PD-L1 mAb S1
      heavy chain

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu

```
            340                 345                 350
Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 124
<211> LENGTH: 449
<212> TYPE: PRT
<213> ORGANISM: Artificial Sequence
<220> FEATURE:
<223> OTHER INFORMATION: Amino acid sequence of the control anti-human
      LAG-3 mAb 25F7 heavy chain

<400> SEQUENCE: 124

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 125
<211> LENGTH: 214
<212> TYPE: PRT
<213> ORGANISM: Artificial Sequence
<220> FEATURE:
<223> OTHER INFORMATION: Amino acid sequence of the control anti-human
      LAG-3 mAb 25F7 light chain

<400> SEQUENCE: 125

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 126
<211> LENGTH: 525
<212> TYPE: PRT
<213> ORGANISM: Artificial Sequence
<220> FEATURE:
<223> OTHER INFORMATION: Amino acid sequence of human LAG-3

<400> SEQUENCE: 126

Met Trp Glu Ala Gln Phe Leu Gly Leu Leu Phe Leu Gln Pro Leu Trp
1               5                   10                  15
Val Ala Pro Val Lys Pro Leu Gln Pro Gly Ala Glu Val Pro Val Val
            20                  25                  30
Trp Ala Gln Glu Gly Ala Pro Ala Gln Leu Pro Cys Ser Pro Thr Ile
        35                  40                  45
Pro Leu Gln Asp Leu Ser Leu Leu Arg Arg Ala Gly Val Thr Trp Gln
    50                  55                  60
His Gln Pro Asp Ser Gly Pro Pro Ala Ala Ala Pro Gly His Pro Leu
65                  70                  75                  80
Ala Pro Gly Pro His Pro Ala Ala Pro Ser Ser Trp Gly Pro Arg Pro
                85                  90                  95
Arg Arg Tyr Thr Val Leu Ser Val Gly Pro Gly Gly Leu Arg Ser Gly
            100                 105                 110
Arg Leu Pro Leu Gln Pro Arg Val Gln Leu Asp Glu Arg Gly Arg Gln
        115                 120                 125
Arg Gly Asp Phe Ser Leu Trp Leu Arg Pro Ala Arg Arg Ala Asp Ala
    130                 135                 140
Gly Glu Tyr Arg Ala Ala Val His Leu Arg Asp Arg Ala Leu Ser Cys
145                 150                 155                 160
Arg Leu Arg Leu Arg Leu Gly Gln Ala Ser Met Thr Ala Ser Pro Pro
                165                 170                 175
Gly Ser Leu Arg Ala Ser Asp Trp Val Ile Leu Asn Cys Ser Phe Ser
            180                 185                 190
Arg Pro Asp Arg Pro Ala Ser Val His Trp Phe Arg Asn Arg Gly Gln
        195                 200                 205
Gly Arg Val Pro Val Arg Glu Ser Pro His His Leu Ala Glu Ser
    210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                245                 250                 255
Leu Thr Val Leu Gly Leu Glu Pro Pro Thr Pro Leu Thr Val Tyr Ala
            260                 265                 270
Gly Ala Gly Ser Arg Val Gly Leu Pro Cys Arg Leu Pro Ala Gly Val
        275                 280                 285
Gly Thr Arg Ser Phe Leu Thr Ala Lys Trp Thr Pro Pro Gly Gly Gly
    290                 295                 300
```

```
Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
            325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
            405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 127
<211> LENGTH: 521
<212> TYPE: PRT
<213> ORGANISM: Artificial Sequence
<220> FEATURE:
<223> OTHER INFORMATION: Amino acid sequence of mouse LAG-3

<400> SEQUENCE: 127

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
            85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140
```

```
Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
            165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
            195                 200                 205

Asn Ser Pro Arg His Phe Leu Ala Glu Thr Phe Leu Leu Leu Pro Gln
            210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
            245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
            275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
            325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
            355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
            405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu
            435                 440                 445

Gly Ala Leu Ser Leu Phe Leu Leu Val Ala Gly Ala Phe Gly Phe His
450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
            485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
            515                 520

<210> SEQ ID NO 128
<211> LENGTH: 533
<212> TYPE: PRT
<213> ORGANISM: Artificial Sequence
<220> FEATURE:
<223> OTHER INFORMATION: Amino acid sequence of cynomolgus LAG-3
```

<400> SEQUENCE: 128

| | | | | | | | | | | | | | | |
|---|---|---|---|---|---|---|---|---|---|---|---|---|---|---|
|Met|Trp|Glu|Ala|Gln|Phe|Leu|Gly|Leu|Leu|Phe|Leu|Gln|Pro|Leu|Trp|
|1| | | |5| | | | |10| | | | |15| |

Val Ala Pro Val Lys Pro Pro Gln Pro Gly Ala Glu Ile Ser Val Val
              20              25              30

Trp Ala Gln Glu Gly Ala Pro Ala Gln Leu Pro Cys Ser Pro Thr Ile
              35              40              45

Pro Leu Gln Asp Leu Ser Leu Leu Arg Arg Ala Gly Val Thr Trp Gln
50                     55              60

His Gln Pro Asp Ser Gly Pro Ala Ala Pro Gly His Pro Pro
65                    70                 75              80

Val Pro Gly His Arg Pro Ala Ala Pro Tyr Ser Trp Gly Pro Arg Pro
              85              90              95

Arg Arg Tyr Thr Val Leu Ser Val Gly Pro Gly Gly Leu Arg Ser Gly
            100             105            110

Arg Leu Pro Leu Gln Pro Arg Val Gln Leu Asp Glu Arg Gly Arg Gln
              115            120            125

Arg Gly Asp Phe Ser Leu Trp Leu Arg Pro Ala Arg Arg Ala Asp Ala
130                   135              140

Gly Glu Tyr Arg Ala Thr Val His Leu Arg Asp Arg Ala Leu Ser Cys
145                  150            155            160

Arg Leu Arg Leu Arg Val Gly Gln Ala Ser Met Thr Ala Ser Pro Pro
              165            170            175

Gly Ser Leu Arg Thr Ser Asp Trp Val Ile Leu Asn Cys Ser Phe Ser
            180             185            190

Arg Pro Asp Arg Pro Ala Ser Val His Trp Phe Arg Ser Arg Gly Gln
              195            200            205

Gly Arg Val Pro Val Gln Gly Ser Pro His His Leu Ala Glu Ser
        210            215              220

Phe Leu Phe Leu Pro His Val Gly Pro Met Asp Ser Gly Leu Trp Gly
225                   230            235            240

Cys Ile Leu Thr Tyr Arg Asp Gly Phe Asn Val Ser Ile Met Tyr Asn
              245            250            255

Leu Thr Val Leu Gly Leu Glu Pro Ala Thr Pro Leu Thr Val Tyr Ala
            260             265            270

Gly Ala Gly Ser Arg Val Glu Leu Pro Cys Arg Leu Pro Pro Ala Val
          275             280            285

Gly Thr Gln Ser Phe Leu Thr Ala Lys Trp Ala Pro Pro Gly Gly Gly
        290            295            300

Pro Asp Leu Leu Val Ala Gly Asp Asn Gly Asp Phe Thr Leu Arg Leu
305                  310            315            320

Glu Asp Val Ser Gln Ala Gln Ala Gly Thr Tyr Ile Cys His Ile Arg
              325            330            335

Leu Gln Gly Gln Gln Leu Asn Ala Thr Val Thr Leu Ala Ile Ile Thr
            340             345            350

Val Thr Pro Lys Ser Phe Gly Ser Pro Gly Ser Leu Gly Lys Leu Leu
              355            360            365

Cys Glu Val Thr Pro Ala Ser Gly Gln Glu His Phe Val Trp Ser Pro
        370            375            380

Leu Asn Thr Pro Ser Gln Arg Ser Phe Ser Gly Pro Trp Leu Glu Ala
385                   390            395            400

Gln Glu Ala Gln Leu Leu Ser Gln Pro Trp Gln Cys Gln Leu His Gln

```
                    405                 410                 415
Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
        435                 440                 445

His Leu Pro Leu Phe Leu Ile Leu Gly Val Leu Phe Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Leu Glu Pro Glu Pro
        500                 505                 510

Glu Leu Glu Arg Glu Leu Gly Pro Glu Pro Glu Pro Gly Pro Glu Pro
    515                 520                 525

Glu Pro Glu Gln Leu
    530
```

<210> SEQ ID NO 129
<211> LENGTH: 290
<212> TYPE: PRT
<213> ORGANISM: Artificial Sequence
<220> FEATURE:
<223> OTHER INFORMATION: Amino acid sequence of human PD-L1

<400> SEQUENCE: 129

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
```

```
                    225                 230                 235                 240

Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
                    260                 265                 270

Gly Ile Gln Asp Thr Asn Ser Lys Lys Gln Ser Asp Thr His Leu Glu
                275                 280                 285

Glu Thr
    290

<210> SEQ ID NO 130
<211> LENGTH: 290
<212> TYPE: PRT
<213> ORGANISM: Artificial Sequence
<220> FEATURE:
<223> OTHER INFORMATION: Amino acid sequence of murine PD-L1

<400> SEQUENCE: 130

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
```

<210> SEQ ID NO 131
<211> LENGTH: 290
<212> TYPE: PRT
<213> ORGANISM: Artificial Sequence
<220> FEATURE:
<223> OTHER INFORMATION: Amino acid sequence of cynomolgus PD-L1

<400> SEQUENCE: 131

```
Met Arg Ile Phe Ala Val Phe Ile Phe Thr Ile Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Thr Ser Leu Ile Val Tyr Trp Glu Met Glu Asp Lys Asn Ile
    50                  55                  60

Ile Gln Phe Val His Gly Glu Glu Asp Leu Lys Val Gln His Ser Asn
65                  70                  75                  80

Tyr Arg Gln Arg Ala Gln Leu Leu Lys Asp Gln Leu Ser Leu Gly Asn
                85                  90                  95

Ala Ala Leu Arg Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
        195                 200                 205

Cys Ile Phe Arg Arg Leu Asp Pro Glu Glu Asn His Thr Ala Glu Leu
    210                 215                 220

Val Ile Pro Glu Leu Pro Leu Ala Leu Pro Pro Asn Glu Arg Thr His
225                 230                 235                 240

Leu Val Ile Leu Gly Ala Ile Phe Leu Leu Gly Val Ala Leu Thr
                245                 250                 255

Phe Ile Phe Tyr Leu Arg Lys Gly Arg Met Met Asp Met Lys Lys Cys
            260                 265                 270

Gly Ile Arg Val Thr Asn Ser Lys Lys Gln Arg Asp Thr Gln Leu Glu
        275                 280                 285

Glu Thr
    290
```

<210> SEQ ID NO 132
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/FITC mAb2 FS18-7-108-29/4420 comprising LALA
      mutation

```
<400> SEQUENCE: 132

Glu Val Lys Leu Asp Glu Thr Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65              70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145             150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225             230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305             310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Val Val Glu Trp Glu Ser
    370                 375                 380

Asn Gly Gln Pro Glu Asn Asn Tyr Lys Thr Thr Pro Pro Val Leu Asp
385             390                 395                 400

Ser Asp Gly Ser Phe Phe Leu Tyr Ser Lys Leu Thr Val Pro Phe Glu
                405                 410                 415
```

```
Arg Trp Met Trp Pro Asp Glu Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 133
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/FITC mAb2 FS18-7-108-35/4420 comprising LALA
      mutation

<400> SEQUENCE: 133

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Trp Asp Glu Pro Trp Gly Glu Asp Val Ser Leu Thr Cys
        355                 360                 365

Leu Val Lys Gly Phe Tyr Pro Ser Asp Ile Ser Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 134
<211> LENGTH: 447
<212> TYPE: PRT
<213> ORGANISM: Artificial Sequence
<220> FEATURE:
<223> OTHER INFORMATION: Amino acid sequence of the heavy chain of
      anti-mouse LAG-3/FITC mAb2 FS18-7-108-29/4420

<400> SEQUENCE: 134

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

-continued

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Trp Asp Glu Pro Trp Gly Glu Asp Val Ser Leu Thr Cys
                355                 360                 365

Leu Val Lys Gly Phe Tyr Pro Ser Asp Ile Val Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Pro Phe Glu
                405                 410                 415

Arg Trp Met Trp Pro Asp Glu Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 135
<211> LENGTH: 107
<212> TYPE: PRT
<213> ORGANISM: Artificial Sequence
<220> FEATURE:
<223> OTHER INFORMATION: Amino acid sequence of Fcab FS18-7-9 CH3 domain
      comprising C-terminal lysine

<400> SEQUENCE: 135

Gly Gln Pro Arg Glu Pro Gln Val Tyr Thr Leu Pro Pro Ser Trp Asp
1               5                   10                  15

Glu Pro Trp Gly Glu Asp Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Pro Tyr Asp Arg Trp Val Trp Pro
65                  70                  75                  80

Asp Glu Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 136
<211> LENGTH: 5
<212> TYPE: PRT
<213> ORGANISM: Artificial Sequence
<220> FEATURE:
<223> OTHER INFORMATION: Amino acid sequences of the CDRs of anti-PD-L1
``` antibody 84G09 (according to Kabat) HCDR1

<400> SEQUENCE: 136

Asp Tyr Ala Met His
1               5

<210> SEQ ID NO 137
<211> LENGTH: 17
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to Kabat) HCDR2

<400> SEQUENCE: 137

Gly Ile Ser Trp Lys Ser Asn Ile Ile Gly Tyr Ala Asp Ser Val Lys
1               5                   10                  15

Gly

<210> SEQ ID NO 138
<211> LENGTH: 13
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to Kabat) HCDR3

<400> SEQUENCE: 138

Asp Ile Thr Gly Ser Gly Ser Tyr Gly Trp Phe Asp Pro
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to Kabat) LCDR1

<400> SEQUENCE: 139

Arg Ala Ser Gln Ser Ile Ser Ser Tyr Leu Asn
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to Kabat) LCDR2

<400> SEQUENCE: 140

Val Ala Ser Ser Leu Gln Ser
1               5

<210> SEQ ID NO 141
<211> LENGTH: 9
<212> TYPE: PRT
<213> ORGANISM: Artificial Sequence
<220> FEATURE:
<223> OTHER INFORMATION: Amino acid sequences of the CDRs of anti-PD-L1
      antibody 84G09 (according to Kabat) LCDR3

<400> SEQUENCE: 141

Gln Gln Ser Tyr Ser Asn Pro Ile Thr
1               5

<210> SEQ ID NO 142
<211> LENGTH: 318
<212> TYPE: DNA
<213> ORGANISM: Artificial Sequence
<220> FEATURE:
<223> OTHER INFORMATION: CHO codon optimised nucleotide sequence of Fcab
      FS18-7-9 CH3 domain

<400> SEQUENCE: 142

```
ggccagcccc gggaacccca ggtgtacaca ctgcctccat cctgggatga gccctggggc    60
gaggatgtgt ctctgacctg tctcgtgaaa ggcttctacc cctccgatat cgccgtggaa   120
tgggagagca acggccagcc cgagaacaac tacaagacca ccccccctgt gctggactcc   180
gacggctcat tcttcctgta cagcaagctg acagtgccct acgacagatg ggtgtggccc   240
gacgagttct cctgctccgt gatgcacgag gccctgcaca accactacac ccagaagtcc   300
ctgtccctga gccccggc                                                  318
```